United States Patent
Kledal et al.

(10) Patent No.: US 8,592,554 B2
(45) Date of Patent: Nov. 26, 2013

(54) IMMUNOTOXINS FOR THE TREATMENT OF DISEASES RELATED TO CMV INFECTION

(75) Inventors: Thomas Nitschke Kledal, Soro (DK); Mette M. R. Roed, Soborg (DK)

(73) Assignee: Inagen ApS, Soro (DK)

( * ) Notice: Subject to any disclaimer, the term of this patent is extended or adjusted under 35 U.S.C. 154(b) by 1039 days.

(21) Appl. No.: 12/306,395

(22) PCT Filed: Jul. 3, 2007

(86) PCT No.: PCT/DK2007/050082
§ 371 (c)(1),
(2), (4) Date: Oct. 20, 2009

(87) PCT Pub. No.: WO2008/003327
PCT Pub. Date: Jan. 10, 2008

(65) Prior Publication Data
US 2010/0048470 A1    Feb. 25, 2010

(30) Foreign Application Priority Data
Jul. 3, 2006 (DK) .................................. 2006 00900

(51) Int. Cl.
*C07K 14/52* (2006.01)
*C12N 15/19* (2006.01)

(52) U.S. Cl.
USPC ..... 530/350; 530/387.9; 435/243; 435/320.1; 435/339; 435/252.34

(58) Field of Classification Search
None
See application file for complete search history.

(56) References Cited

U.S. PATENT DOCUMENTS

| | | | |
|---|---|---|---|
| 4,554,101 A | 11/1985 | Hopp | |
| 6,420,121 B1* | 7/2002 | Nelson et al. | 435/7.1 |
| 7,585,502 B2* | 9/2009 | Hardiman et al. | 424/130.1 |
| 2002/0192212 A1* | 12/2002 | Imai et al. | 424/140.1 |
| 2004/0033209 A1 | 2/2004 | Mack et al. | |

FOREIGN PATENT DOCUMENTS

| | | | | |
|---|---|---|---|---|
| WO | 9911655 | 3/1999 | | |
| WO | 0004926 | 2/2000 | | |
| WO | 0170173 | 9/2001 | | |
| WO | WO/2006/045233 | * 5/2006 | ............. | A61K 51/08 |

OTHER PUBLICATIONS

Combadiere et al. (The Journal of Biological Chemistry, 1998, vol. 273, p. 23799-23804).*
B. Barnett et al., "Selective cytotoxicity towards cytomegalovirus-infected cells by immunotoxins consisting of gelonin linked to anti-cytomegalovirus antibody", Antiviral Res., 28: 93-100 (1995).
B. Barnett et al., "Selective Cytotoxicity of Ricin A Chain Immunotoxins towards Murine Cytomegalovirus-Infected Cells", Antimicrobial Agents and Chemotherapy, 40(2): 470-472 (1996).
P.S. Beisser et al., "Viral Chemokine Receptors and Chemokines in Human Cytomegalovirus Trafficking and Interaction with the Immune System", Current Topics in Microbiology and Immunology, 269: 203-204 (2002).
H. Bruhl et al., "Depletion of CCR5-Expressing Cells with Bispecific Antibodies and Chemokine Toxins: A New Strategy in the Treatment of Chronic Inflammatory Diseases and HIV", J. Immun., 166(4): 2420-2426 (2001).
D. He et al., "Arg9-peptide facilitates the internalization of an anti-CEA immunotoxin and potentiates its specific cytotoxicity to target cells", Int. J. Biochem. Cell Biol., 37(1): 192-205 (2005).
T. Kledal et al., "Selective recognition of the membrane-bound CX3C chemokine, fractalkine, by the human cytomegalovirus-encoded broad-spectrum receptor US28", FEBS Letters 441: 209-214 (1998).
J. Kyte et al., "A Simple Method for Displaying the Hydropathic Character of a Protein", J. Mol. Biol., 157: 105-132 (1982).
L. Mizoue et al., "Molecular Determinants of Receptor Binding and Signaling by the CX3C Chemokine Fractalkine", J Biol. Chem., 276(36): 33906-33914 (2001).

* cited by examiner

*Primary Examiner* — Agnieszka Boesen
(74) *Attorney, Agent, or Firm* — Patrick J. Hagan; Dann, Dorfman, Herrell and Skillman, P.C.

(57) ABSTRACT

The present invention relates to the field of cytomegalovirus (CMV) infection. In particular the present invention relates to highly specific immunotoxins useful in treating diseases related to CMV infection. CMV encodes chemokine receptors that undergo constitutive internalization. Thus CMV infected cells can be targeted specifically with immunotoxins with high affinity to CMV encoded constitutively internalizing receptors. This will ensure efficient uptake of the immunotoxin by the CMV infected cell, and thereby ensure the death of the infected cell with a minimum of unwanted toxicity and side effects. Furthermore, the invention relates to a way of inhibiting CMV replication and/or growth by using immunotoxins by targeting constitutively internalizing CMV encoded receptors.

15 Claims, No Drawings

IMMUNOTOXINS FOR THE TREATMENT OF DISEASES RELATED TO CMV INFECTION

FIELD OF INVENTION

The present invention relates to immunotoxins useful in treating diseases related to CMV infection. The invention also relates to use of the immunotoxin as a medicament, pharmaceutical compositions comprising the immunotoxin and a kit for treatment or prevention of CMV infection comprising the immunotoxin.

BACKGROUND

Cytomegalovirus

Cytomegalovirus (CMV) is an important human pathogen and a major opportunist, which emerges to cause disease in the immuno-compromised such as AIDS patients, neonates, and individuals who have been given immunosuppressive drugs as part of a transplantation regimen. In these individuals, the consequences of CMV in acute or re-emerging infections can be dire, including retinitis, encephalitis, and pneumocystis, among other pathologies. Furthermore, in immuno-competent hosts, CMV establishes a persistent lifelong infection through which it has been linked to a variety of inflammatory conditions including coronary artery occlusion following heart transplant and atherectomy and restenosis following angioplasty. CMV interacts with leukocytes during acute infection of the host as well as during lifelong latency. As such, leukocytes are important players in CMV-induced diseases and have been implicated in the acute phase of infection as vehicles for dissemination of virus and as sites of residence during lifelong latency.

CMV infection affects approximately 30 to 60 percent of the estimated 29,000 patients receiving bone marrow or solid organ transplantations in the US annually, causing transplant rejection, serious illness and even death if untreated. Expensive antiviral drug therapy is used to control the disease, but does not eliminate the infection. These treatments cost per patient between $30.000 to $50.000 USD a year. CMV infection causes severe consequences in about 3,600 infants and death in about 400 each year in the U.S. CMV infection also affects HIV/AIDS patients, with an estimated 40% of all AIDS patients requiring treatment against CMV infection. There currently remains no effective cure for CMV infection. Viral suppressants do exist, however, carry strong side effects and serve only to control infection.

The most common drugs for the treatment of CMV infection in transplantation patients and HIV/AIDS patients are the generic drugs Ganciclovir and Acyclovir, originally developed for herpes simplex virus (HSV). Ganciclovir and Acyclovir have a suppressing effect on CMV as well as on HSV. Vistide from Gilead is a newer compound that is expected to grow and take over the market with Roche's Valcyte at the expense of the older generic drugs.

None of the existing drugs, patented or generic, can eradicate the infection, merely halting the CMV disease progression in immuno-compromised or immuno-suppressed patients. In recent clinical studies, Foscavir and Ganciclovir were compared on their ability to treat immuno-compromised patients. The results showed a 30% better suppression of the infection using Foscavir. However 40% of the patients on Foscavir later switched to Ganciclovir because of intolerable nausea. These results show that there is room for improvement both in efficacy and in toxicity levels.

Immunotoxins

An immunotoxin is a ligand combined with a toxin, which can be used to kill cells expressing receptors for the ligand. Immunotoxin treatment is also known as ligand-targeted therapeutics. Thus, the immunotoxins contain a targeting moiety (a ligand) for delivery and a toxic moiety for cytotoxicity. The ligands currently used are monoclonal antibodies, cytokines/growth factors and soluble receptors. An advantage with immunotoxins over e.g. traditional chemotherapy drugs is, that the cells need not be dividing to be killed. Furthermore, if the immunotoxin is efficiently internalized, side effects will not occur in antigen negative cells.

In general, however, immunotoxins have not shown impressive levels of efficacy. A common problem is that they are not sufficiently specific for the diseased cells, and furthermore, often are incapable of efficiently entering the diseased cells to exert its cytotoxic effects. Immunotoxins also result in higher levels of systemic toxicity than other therapies, presumably because of non-specific uptake of the immunotoxin.

Currently, new approaches to immunotoxins are being explored to overcome problems of toxicity, immunogenicity, and heterogeneity of antigen expression. These approaches include the use of genetic engineering to fuse the translocation and catalytic domains of toxins to human single chain antibodies and to use phage display to select high affinity, tumour-selective ligands. Use of bivalent constructs can also increase the affinity and potency. Other approaches, centres around the selection of ligands that target tumour vascular endothelium and the targeting of oncogene products or differentiation antigens. In spite of that research on immunotoxins has been ongoing in the last two decades, no immunotoxin against virus related diseases is available on the market.

Immunotoxins tend to be more useful in haematological malignancies, which are characterized by a high percentage of malignant cells that express the target antigen in contrast to solid tumours, which are characterized by a mixed cell population, and cells that are often not easily accessible for the immunotoxin. In the case of targeting tumour cells, monoclonal antibodies that also target normal cells are typically used because unique tumour associated antigens have not been identified on most tumour cells. Even though the tumour cells express higher levels of the selected antigen, and tumour cells are preferentially killed, the treatment is still often associated with significant side effects. Another drawback has been the mouse origin of the monoclonal antibodies, which are immunogenic in humans. This problem has been largely solved by the use of human antibodies and also by using recombinant human growth factors, which are not immunogenic in humans.

Immunotoxin Internalization

Most immunotoxins are developed against cells that have undergone malignant transformation and as a part of this transformation therefore overexpress a certain antigen or a group of certain antigens. Even though these antigens are overexpressed on the transformed cells, they are rarely specific for the transformed cells, but are often also expressed on normal cells. Thus, only a few cellular antigens are over expressed on transformed cells. Therefore, to avoid undesired toxicity by killing normal cells expressing the target antigen, drug developers are restricted to target very few candidate disease antigens, and drug developers have therefore traditionally been restricted to select a target antigen solely based on the cell type distribution. Consequently, many immunotoxins have not been able to efficiently enter the target cells, even though they bind the target antigen with high affinity, resulting in inadequate potency.

One attempt to solve the problem of getting the immunotoxin efficiently into the target cell has been made by He D. et al, 2005. They used arginine-containing membrane translocation signals (MTS) (e.g. Tat and VP22) as carriers for transporting an arginine (Arg9-peptide) containing immunotoxin, PE35/CEA(Fv)/KDEL into carciniembryonic antigen (CEA) expressing target cells. The authors suggests, that incorporation of the Arg9 peptide (a 9-mer arginine peptide) into the immunotoxin facilitates the receptor-mediated endocytosis of the PE35/CEA(Fv)/KDEL immunotoxin. Unfortunately, the introduction of a MTS signal in the immunotoxin result in loss of specificity towards cells expressing the target antigen. Therefore this approach seems not to be the solution to the problem of how to get the immunotoxin into the target cells.

Immunotoxins consisting of a cytokine/growth factor and a toxin (a cytokine-based immunotoxins) has the advantage that it can be effectively internalized after cytokine mediated receptor activation followed by receptor internalization. However, cytokine based immunotoxins suffers from two major problems. 1) Cytokine-induced receptor internalization requires that the ligand retain agonistic properties, which may have unwanted stimulatory effects on the target cells and other cells bearing the receptor. 2) Cytokine-based immunotoxins interacts with cytokine receptors on normal cells and thereby kill normal cells in addition to the diseased target cells. Thus a successful cytokine based immunotoxin need 1) to be able to stimulate internalization without retaining agonistic properties that may induce unwanted stimulatory effects, and 2) to interact and be internalized in diseased cells only and not by healthy cells bearing the same cytokine receptor.

Immunotoxins for Anti-Viral Therapy
HIV

Immunotoxins have been evaluated for therapy of HIV infection. For example, immunotoxins have targeted to CD4, with some success. Also soluble CD4 has been conjugated to toxins, and the resulting immunotoxin inhibits synthesis of viral proteins in infected cells and spread of virus in vitro. Immunotoxins have also been targeted to the HIV envelope protein gp160 and it's components gp120 and gp41. However these attempts have had little effect, partly because of HIV antigenic variation and partly because of anti-epitope antibodies present in the serum of infected individuals.

CMV

Prior attempts to treat CMV using immunotoxin strategies have not been successful.

An academic research group has prepared and tested immunotoxins targeting CMV-infected cells (Barnett et al. 1995, Smee at al. 1995, Barnet et al, 1996). Barnett et al. (1995) described the generation of an immunotoxin specific for cells infected with human CMV, and an immunotoxin specific for cells infected with mouse CMV. Both immunotoxins were polyclonal, i.e. the antibodies were not directed against a specific well defined target antigen. Furthermore, the anti serum (anti MCMV and HCMV) were only purified by protein A affinity, thus the purified polyclonal antisera contains a non-defined pool of antibodies, against CMV antigens (MCMV or HCMV) and against other non-defined antigens. The authors state that "The virus specific antibody in these preparations accounted for less than a few percent of the total IgG." The polyclonal antibody pool (antisera) were coupled to the toxin gelonin. The effect of the anti human CMV immunotoxin were measured by the ability of the immunotoxin to inhibit s35-metheonine incorporation into proteins as a measure of the immunotoxin ability to inhibit ribosome activity. The authors show no data on the ability of the anti human CMV immunotoxin to inhibit the growth or replication of human CMV in infected cells. More over the authors show, that the anti human CMV immunotoxin only inhibits 35S-methionine incorporation by approximately 15%. In contrast, the authors show that the anti mouse CMV immunotoxin can inhibit the incorporation of S35-metheonine >90%. Additionally, the authors state that addition of the anti mouse CMV immunotoxin to mouse cells (mouse mammary tumor cell line, C127I) infected with mouse CMV at an MOI of 0.001 inhibited the virus yield at 7 days post infection with approximately 2 log (100 fold) at 20 µg immunotoxin/ml.

Three papers describe the use of monoclonal antibodies against mouse cytomegalovirus (Smee et al. 1995a, Smee et al. 1995b, Barnett et al. 1996). The antibodies were generated from mouse CMV infected BALB/c mice. Treatment of MCMV infected cells with the monoclonal antibody D5.F10.B8 (not coupled to any toxin) caused a 3-3.5 log 10 decrease in virus titer, but there was no dose response effect among the various concentrations tested (1.25, 2.5, 5, 10 and 20 µg/ml) (Smee et. al. 1995a). However the authors show a synergistic inhibition of virus yield using a combination of high concentrations of monoclonal antibody in combination with either high concentrations of ganciclovir or high concentrations of (S)-1-[3-hydroxy-(2-phosphonylmethoxy)-propyl]cytosine (HPMPC). In vivo, treatment with the monoclonal antibody alone or in combination with either 25 or 50 mg/kg/day ganciclovir has no or only minor effect in MCMV induced mortality in SCID mice.

Coupling of the neutralizing monoclonal antibody D5.F10.B8 or of the non-neutralizing monoclonal antibody C34.18.F6 to recin A chain generated two antibody based immunotoxins against mouse CMV. It should be noted that even thought the antibodies are monoclonal, the antigens are not defined. Treatment of MCMV infected cells with the monoclonal immunotoxins caused a 2-3 log 10 decrease in virus titers. Additionally, the authors show a synergistic inhibition of virus yield using a combination of high concentrations of monoclonal antibody in combination with either high concentrations of ganciclovir or high concentrations of (S)-1-[3-hydroxy-(2-phosphonylmethoxy)-propyl]cytosine (HPMPC). In vivo, treatment with the immunotoxins alone had no effect on MCMV induced mortality in SCID mice. Combination therapy with either the D5.F10.B8 or the C34.18.F6 based immunotoxins with 50 mg/kg/day ganciclovir appeared to suggest a mild synergy in delaying MCMV induced mortality in SCID mice from 27.3±2.5 (ganciclovir alone) to 29.3±1.1 days (ganciclovir+C34 immunotoxin) and 30.4±3.1 days (ganciclovir+D5 immunotoxin) (Smee et al. 1995b). The authors explain the pour effect of the immunotoxins with lack of knowledge on the actual concentrations of immunotoxin in the animals treated, and lack of knowledge on whether the immunotoxins reached the site of viral replication within the animal. Furthermore the authors do not show any data on the actual target antigen, whether the antigen is expressed in the infected animals, the kinetics of the immunotoxin in the animal, the affinity of the immunotoxins to the infected cells or whether the antibodies are internalized into the infected cells. Also, the authors show no difference in the effect on viral infection between the unconjugated monoclonal antibodies or the toxin conjugated antibodies.

SUMMARY OF THE INVENTION

By designing immunotoxins with high affinity towards constitutively internalizing CMV encoded receptors, efficient uptake of the immunotoxin by the infected cell, and thereby the death of the infected cell is ensured. Since the internalization of the immunotoxin is considered the rate-limiting step in immunotoxin-mediated cytotoxicity, targeting constitutively internalizing receptors will solve a central problem in use of immunotoxin based drugs. Thus, the invention concerns immunotoxins that target constitutively internalizing receptors, which ensure that the immunotoxin will be transported into the target cell, where it can exert its function, i.e. kill the cell. Furthermore, the immunotoxins of the invention target receptors only present on CMV-infected cells and consequently the immunotoxins can be used in the treatment or prevention of CMV-infection.

In one aspect, the invention relates to an immunotoxin comprising (a) a ligand that binds a constitutively internalizing receptor encoded by human CMV and expressed on the CMV infected cell and (b) a toxin that is cytotoxic to the CMV infected cell, wherein the immunotoxin is not SEQ ID NO:1. In a second aspect, the invention relates to use of an immunotoxin according to the invention as a medicament, and to use of an immunotoxin according to the invention for the manufacture of a medicament for the treatment or prevention of a CMV infection. The invention relates also to a pharmaceutical composition comprising an immunotoxin according to the invention or any physiological acceptable salt thereof. Furthermore, the invention relates to a nucleic acid sequence and an expression vector comprising a sequence encoding an immunotoxin according to the invention. Moreover, the invention relates to a kit for treatment or prevention of CMV infection comprising (a) an effective amount of an immunotoxin according to the invention and (b) a therapeutic selected from the group of antiviral therapeutics, immuno-suppressive therapeutics for simultaneous, separate or sequential administration.

DETAILED DESCRIPTION OF THE INVENTION

Definitions

Unless otherwise defined herein or below in the remainder of the specification, all technical and scientific terms used herein have the same meaning as commonly understood by those of ordinary skill in the art to which the invention belongs.

An "immunotoxin" is a bifunctional molecule comprising targeting moiety for delivery (a ligand) and a toxic moiety (toxin) for cytotoxicity. The immunotoxin can be used to kill cells expressing receptors for the ligand.

A "ligand" is defined as any amino acid, peptide, protein, nucleotide, any antibody or part thereof or any non-peptide compound or nano particle, which possesses a specific binding affinity to a receptor or an antigen, e.g. originating from a virus A "toxin" is defined as any substance, being a protein or non-peptide, which is cytotoxic or cytostatic or that induce apoptosis or necrosis or that directly inhibits the replication, growth or dissemination of the pathogen, or that makes the infected cell vulnerable to the infected host immune response.

A "chemokine" is a chemotactic cytokine and includes subfamilies "CC-chemokine", "XC-chemokine", "CXC-chemokine", "CX3C-chemokine". In general a chemokine is a low molecular weight protein that regulates cell migration. Many chemokines also posses the capabilities to induce maturation, activation, proliferation, and differentiation of cells of the immune system.

"CX3CL1" is a chemokine, which is a member of the CX3C chemokine family. CX3CL1 has the amino acid sequence listed in SEQ ID NO:2 and is also named fractalkine and neurotactin.

The term "chemokine domain of CX3CL1" is defined as a polypeptide comprising the amino acid sequence from position 25 to position 100 of SEQ ID NO: 2.

An "antibody" refers to a protein comprising one or more polypeptides substantially or partially encoded by immunoglobulin genes or fragments of immunoglobulin genes. An antibody of the invention is an antibody against a CMV encoded constitutively internalizing receptor.

A "receptor" e.g., a "chemokine receptor" is a receptor, which is activated in cells by a chemokine, e.g., binds a chemokine and initiates intracellular signalling.

"Constitutively internalization" refers to any antigen that is expressed at the plasma membrane and without prior stimulation internalized to the cell cytoplasma or an intracellular compartment from the cell plasma membrane. The antigen internalization may be modulated by a ligand, and the internalized antigen may recycle to the plasma membrane or may be degraded after internalization.

The term "a constitutively active G protein coupled" is defined as a G protein coupled receptor that mediates a signal without activation by a receptor ligand (agonist).

The term "US28" is a G protein coupled receptor encoded by human cytomegalovirus open reading frame US28. US28 is a constitutively internalizing receptor. Thus chemokines or other compounds that binds US28 are internalized into the cell that express the receptor.

"CMV" refers to "cytomegalovirus".

Human CMV also named "human herpesvirus 5" refers to a CMV that is capable of infecting humans.

"CMV diseases" are diseases that are caused or associated with the presence of CMV in the diseased individual or evident from serological investigations of the diseased individual.

CMV is causing acute as well as chronic diseases. The acute diseases, which most often are associated with a high level of viral replication and characterized by affecting multiple organs are mononucleosis like syndromes, perinatal infections in premature infants, CMV syndrome in allograft recipients and disseminated infections in immunocompromised patients such as AIDS patients. The chronic infections, which most often is associated with a low level of viral replication are congenital infections, vascular diseases in transplant patients, vascular diseases in the normal host and inflammatory diseases, especially in the gastrointestinal tract.

A "parent polypeptide" is intended to indicate the polypeptide sequence to be modified (mutated i.e. by deletion, insertion, and/or substitution, conjugated, etc.) in accordance with the present invention. The parent polypeptide sequence may be that of a naturally occurring fraktalkine (such as a mammalian fraktalkine, e.g., a human fraktalkine identified herein as SEQ ID NO:2, or it may be a variant thereof.

A "polypeptide sequence" (e.g., a protein, polypeptide, peptide, etc.) is a polymer of amino acids comprising naturally occurring amino acids or artificial amino acid analogues, or a character string representing an amino acid polymer, depending on context. Given the degeneracy of the genetic code, one or more nucleic acids, or the complementary nucleic acids thereof, that encode a specific polypeptide sequence can be determined from the polypeptide sequence.

A "variant" is a polypeptide comprising a sequence, which differs (by deletion of an amino acid, insertion of an amino acid, and/or substitution of an amino acid for a different amino acid) in one or more amino acid positions from that of a parent polypeptide sequence. The variant sequence may be a non-naturally occurring sequence, i.e., a sequence not found in nature. Preferably, a "variant" retains the same function as the parent polypeptide.

The terminology used for identifying amino acid positions and amino acid substitutions is illustrated as follows: K31 indicates position number 31 occupied by a Lysine (Lys) residue in a reference amino acid sequence, e.g. SEQ ID NO:2. K31A indicates that the Lysine residue of position 31 has been substituted with an Alanine (Ala) residue.

"Naturally occurring" as applied to an object refers to the fact that the object can be found in nature as distinct from being artificially produced by man. For example, a polypeptide or polynucleotide sequence that is present in an organism (including viruses, bacteria, protozoa, insects, plants or mammalian tissue) that can be isolated from a source in nature and which has not been intentionally modified by man in the laboratory is naturally occurring.

"Non-naturally occurring" as applied to an object means that the object is not naturally-occurring, i.e. the object cannot be found in nature as distinct from being artificially produced by man.

The term "pharmaceutical composition" means a composition suitable for pharmaceutical use in an individual. A pharmaceutical composition generally comprises an effective amount of an active agent and a carrier, including, e.g., a pharmaceutically acceptable carrier.

The term "effective amount" means a dosage or amount sufficient to produce a desired result. The desired result may comprise an objective or subjective improvement in the recipient of the dosage or amount.

A "prophylactic treatment" is a treatment administered to a individual who does not display signs or symptoms of a disease, pathology, or medical disorder, or displays only early signs or symptoms of a disease, pathology, or disorder, such that treatment is administered for the purpose of diminishing, preventing, or decreasing the risk of developing the disease, pathology, or medical disorder. A prophylactic treatment functions as a preventative treatment against a disease or disorder.

A "therapeutic treatment" is a treatment administered to an individual who displays symptoms or signs of pathology, disease, or disorder, in which treatment is administered to the individual for the purpose of diminishing or eliminating those signs or symptoms of pathology, disease, or disorder.

A "nucleotide acid sequence" (e.g., a nucleic acid, polynucleotide, oligonucleotide, etc.) is a polymer of nucleotides comprising nucleotides A, C, T, U, G, or other naturally occurring nucleotides or artificial nucleotide analogues, or a character string representing a nucleic acid, depending on context. Either the given nucleic acid or the complementary nucleic acid can be determined from any specified polynucleotide sequence. Unless otherwise indicated, a particular nucleic acid sequence also implicitly encompasses conservatively modified variants thereof (e.g., degenerate codon substitutions) and complementary sequences and as well as the sequence explicitly indicated. Specifically, degenerate codon substitutions may be achieved by generating sequences in which the third position of one or more selected (or all) codons is substituted with mixed-base and/or deoxyinosine residues (Batzer et al. (1991) Nucleic Acid Res 19:5081; Ohtsuka et al. (1985) J Biol Chem 260:2605-2608; Cassol et al. (1992); Rossolini et al. (1994) Mol Cell Probes 8:91-98). The term nucleic acid is used interchangeably with gene, cDNA, and mRNA encoded by a gene.

"Nucleic acid derived from a gene" refers to a nucleic acid for whose synthesis the gene, or a subsequence thereof, has ultimately served as a template. Thus, an mRNA, a cDNA reverse transcribed from an mRNA, an RNA transcribed from that cDNA, a DNA amplified from the cDNA, an RNA transcribed from the amplified DNA, etc., are all derived from the gene and detection of such derived products is indicative of the presence and/or abundance of the original gene and/or gene transcript in a sample.

"Operably linked" refers to the covalent joining of two or more nucleotide sequences, by means of enzymatic ligation or otherwise, in a configuration relative to one another such that the normal function of the sequences can be performed. For example, the nucleotide sequence encoding a presequence or secretory leader is operably linked to a nucleotide sequence for a polypeptide if it is expressed as a preprotein that participates in the secretion of the polypeptide: a promoter or enhancer is operably linked to a coding sequence if it affects the transcription of the sequence; a ribosome binding site is operably linked to a coding sequence if it is positioned so as to facilitate translation. Generally, "operably linked" means that the nucleotide sequences being linked are contiguous and, in the case of a secretory leader, contiguous and in reading phase. Linking is accomplished by ligation at convenient restriction sites. If such sites do not exist, then synthetic oligonucleotide adaptors or linkers are used, in conjunction with standard recombinant DNA methods.

The term "control sequences" is defined herein to include all components, which are necessary or advantageous for the expression of a polypeptide of the present invention. Each control sequence may be native or foreign to the nucleotide sequence encoding the polypeptide. Such control sequences include, but are not limited to, a leader, polyadenylation sequence, propeptide sequence, promoter, signal peptide sequence, and transcription terminator. At a minimum, the control sequences include a promoter, and transcriptional and translational stop signals. The control sequences may be provided with linkers for the purpose of introducing specific restriction sites facilitating ligation of the control sequences with the coding region of the nucleotide sequence encoding a polypeptide.

In the present context, the term "expression vector" covers a DNA molecule, linear or circular, that comprises a segment encoding a polypeptide, and which is operably linked to additional segments that provide for its transcription.

The term "host cell", as used herein, includes any cell type, which is susceptible to transformation with a nucleic acid construct.

The term "recombinant" when used with reference, e.g., to a cell, virus, nucleotide, vector, protein, or polypeptide typically indicates that the cell, virus, nucleotide, or vector has been modified by the introduction of a heterologous (or foreign) nucleic acid or the alteration of a native nucleic acid, or that the protein or polypeptide has been modified by the introduction of a heterologous amino acid, or that the cell is derived from a cell so modified. Recombinant cells express nucleic acid sequences (e.g., genes) that are not found in the native (non-recombinant) form of the cell or express native nucleic acid sequences (e.g., genes) that would be abnormally expressed under-expressed, or not expressed at all.

The term "identical" or "identity," in the context of two or more nucleic acid or polypeptide sequences, refers to two or more sequences or subsequences that are the same or have a specified percentage of amino acid residues or nucleotides that are the same, when compared and aligned for maximum correspondence, as measured using one of the following sequence comparison algorithms or by visual inspection.

The term "sequence identity" or "percent identity" ("% identity") means that two polynucleotide or polypeptide sequences are identical (i.e., on a nucleotide-by-nucleotide basis or amino acid-by-amino acid basis, respectively) over a window of comparison. The percent sequence identity is calculated by comparing two optimally aligned polynucleotide or polypeptide sequences over the window of comparison, determining the number of positions at which the identical residues occur in both sequences to yield the number of matched positions, dividing the number of matched positions by the total number of positions in the window of comparison (i.e., the window size), and multiplying the result by 100 to yield the percentage of sequence identity (or percentage of sequence similarity). Thus, for example, with regard to polypeptide sequences, the term sequence identity means that two polypeptide sequences are identical (on an amino acid-by-amino acid basis) over a window of comparison, and a percentage of amino acid residue sequence identity (or percentage of amino acid residue sequence similarity), can be calculated. For sequence comparison, typically one sequence acts as a reference sequence to which test sequences are compared. When using a sequence comparison algorithm, test and reference sequences are input into a computer, subsequence coordinates are designated, if necessary, and sequence algorithm program parameters are designated. The sequence comparison algorithm then calculates the percent sequence identity for the test sequence(s) relative to the reference sequence, based on the designated program parameters. Maximum correspondence can be determined by using one of the sequence algorithms described herein (or other algorithms available to those of ordinary skill in the art) or by visual inspection.

Alignment and comparison of relatively short amino acid sequences (less than about 30 residues) is typically straightforward. Comparison of longer sequences can require more sophisticated methods to achieve optimal alignment of two sequences. Optimal alignment of sequences for aligning a comparison window can be conducted by the local homology algorithm of Smith and Waterman (1981) Adv Appl Math 2:482, by the homology alignment algorithm of Needleman and Wunsch (1970) J Mol Biol 48:443, by the search for similarity method of Pearson and Lipman (1988) Proc Natl Acad Sci USA 85:2444, by computerized implementations of these algorithms (GAP, BESTFIT, FASTA, and TFASTA in the Wisconsin Genetics Software Package Release 7.0, Genetics Computer Group, 575 Science Dr., Madison, Wis.), or by inspection, with the best alignment (i.e., resulting in the highest percentage of sequence similarity over the comparison window) generated by the various methods being selected.

A preferred example of an algorithm that is suitable for determining percent sequence identity (percent identity) and sequence similarity is the FASTA algorithm, which is described in Pearson, W.R. & Lipman, D. J. (1988) Proc Natl Acad Sci USA 85:2444. See also, W. R. Pearson (1996) Methods Enzymology 266:227-258. Preferred parameters used in a FASTA alignment of DNA sequences to calculate percent identity are optimized, BL50 Matrix 15: −5, k-tuple=2; joining penalty=40, optimization=28; gap penalty −12, gap length penalty=−2; and width=16.

Other preferred examples of algorithms that are suitable for determining percent sequence identity and sequence similarity are the BLAST and BLAST 2.0 algorithms, which are described in Altschul et al. (1997) Nuc Acids Res 25:3389-3402 and Altschul et al. (1990) J Mol Biol 215:403-410, respectively. BLAST and BLAST 2.0 are used, with the parameters described herein, to determine percent sequence identity for the nucleic acids and proteins of the invention. Software for performing BLAST analyses is publicly available through the National Center for Biotechnology Information (http://www.ncbi.nlm.nih.gov/). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always>0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, M=5, N=−4 and a comparison of both strands. For amino acid sequences, the BLASTP program (e.g., BLASTP 2.0.14; Jun. 29, 2000) uses as defaults a wordlength of 3, and expectation (E) of 10, and the BLOSUM62 scoring matrix (see, Henikoff & Henikoff (1989) Proc Natl Acad Sci USA 89:10915) uses alignments (B) of 50, expectation (E) of 10, M=5, N=−4, and a comparison of both strands. Again, as with other suitable algorithms, the stringency of comparison can be increased until the program identifies only sequences that are more closely related to those in the sequence listings herein (i.e., SEQ ID NOS:1-22), rather than sequences that are more closely related to other similar sequences such as, e.g., similar molecules found in, e.g., GenBank or Geneseq. In other words, the stringency of comparison of the algorithms can be increased so that all known prior art molecules found in, e.g., GenBank or Geneseq, are excluded.

The BLAST algorithm also performs a statistical analysis of the similarity or identity between two sequences (see, e.g., Karlin & Altschul (1993) Proc Natl Acad Sci USA 90:5873-5787). One measure of similarity provided by this algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.2, more preferably less than about 0.01, and most preferably less than about 0.001.

Another preferred example of a useful algorithm is PILEUP. PILEUP creates a multiple sequence alignment from a group of related sequences using progressive, pairwise alignments to show relationship and percent sequence identity or percent sequence similarity. It also plots a tree or dendogram showing the clustering relationships used to create the alignment. PILEUP uses a simplification of the progressive alignment method of Feng & Doolittle (1987) J. Mol. Evol. 35:351-360. The method used is similar to the method described by Higgins & Sharp (1989) CABIOS 5:151-153. The program can align up to 300 sequences, each of a maximum length of 5,000 nucleotides or amino acids. The multiple alignment procedure begins with the pairwise alignment of the two most similar sequences, producing a cluster of two aligned sequences. This cluster is then aligned to the next most related sequence or cluster of aligned sequences. Two clusters of sequences are aligned by a simple extension of the pairwise alignment of two individual sequences. The final alignment is achieved by a series of progressive, pairwise alignments. The program is run by designating specific sequences and their amino acid or nucleotide coordinates for regions of sequence comparison and by designating the program parameters. Using PILEUP, a reference sequence is compared to other test sequences to determine the percent sequence identity (or percent sequence similarity) relationship using the following parameters: default gap weight (3.00), default gap length weight (0.10), and weighted end gaps. PILEUP can be obtained from the GCG sequence analysis software package, e.g., version 7.0 (Devereaux et al. (1984) Nuc Acids Res 12:387-395).

Another preferred example of an algorithm that is suitable for DNA and amino acid sequence alignments is CLUSTALW (Thompson, J. D. et al. (1994) Nuc Acids Res 22:4673-4680). CLUSTALW performs multiple pairwise comparisons between groups of sequences and assembles them into a multiple alignment based on homology. Default Gap open and Gap extension penalties are 10 and 0.05 respectively. For amino acid alignments, the BLOSUM62 matrix can be used as a protein weight matrix (Henikoff and Henikoff (1992) Proc Natl Acad Sci USA 89:10915-10919). Another example of an algorithm suitable for multiple DNA and amino acid sequence alignments is the Jotun Hein method, Hein (1990), from within the MegaLine™ DNASTAR package (MegaLine™ Version 4.03, manufactured by DNASTAR, Inc.) used according to the manufacturer's instructions and default values specified in the program.

It will be understood by one of ordinary skill in the art, that the above discussion of search and alignment algorithms also applies to identification and evaluation of polynucleotide sequences, with the substitution of query sequences comprising nucleotide sequences, and where appropriate, selection of nucleic acid databases.

The phrase "substantially identical" or "substantial identity" in the context of two nucleic acids or polypeptides, refers to two or more sequences or subsequences that have at least about 60%, 70%, 75%, preferably 80% or 85%, more preferably 90%, 91%, 92%, 93%, 94%, 95%, 96%, 97%, 98%, 99%, 99.5%, or greater nucleotide or amino acid residue percent identity, respectively, when compared and aligned for maximum correspondence, as measured using one of the following sequence comparison algorithms or by visual inspection. In certain aspects, the substantial identity exists over a region of amino acid sequences of at least about 10 residues in length, such as, at least about 20, 30, 40, 50, 60, 76, 100, 125, 150, 200, 250, 300, 350, 400, 450, 500, 550, 600 or 650 amino acid residues. In certain aspects, the substantial identity exists over a region of amino acid sequences of at least about 50 residues in length, such as, at least about 60, 76, 100, 125, 150, 200, 250, 300, 350, 400, 450, 500, 550, 600 or 650 amino acid residues. In certain aspects, substantial identity exists over a region of nucleic acid sequences of at least about 150 nucleic acid residues, such as at least about 180, 228, 300, 375, 600, 750, 900, 1050, 1200, 1350, 1500, 1650, 1800 or 1950 nucleic acid residues. In some aspects, the amino acid or nucleic acid sequences are substantially identical over the entire length of the polypeptide sequence or the corresponding coding region.

As applied to polypeptides and peptides, the term "substantial identity" typically means that two polypeptide or peptide sequences, when optimally aligned, such as by the programs BLAST, GAP or BESTFIT using default gap weights (described in detail below) or by visual inspection, share at least about 60% or 70%, often at least 75%, such as at least about 80%, 85%, 90%, 91%, 92%, 93%, 94%, 95%, 96%, 97%, 98%, 99%, or 99.5% or more percent amino acid residue sequence identity or sequence similarity. Similarly, as applied in the context of two nucleic acids, the term substantial identity or substantial similarity means that the two nucleic acid sequences, when optimally aligned, such as by the programs BLAST, GAP or BESTFIT using default gap weights (described in detail below) or by visual inspection, share at least about 60 percent, 70 percent, or 80 percent sequence identity or sequence similarity, preferably at least about 90 percent amino acid residue sequence identity or sequence similarity, more preferably at least about 95 percent sequence identity or sequence similarity, or more (including, e.g., about 90, 91, 92, 93, 94, 95, 96, 97, 98, 98.5, 99, 99.5, or more percent nucleotide sequence identity or sequence similarity)

The following SEQ ID numbers are referred to in the description:

| | |
|---|---|
| SEQ ID NO: 1: | Immunotoxin comprising Rantes and PE38KDEL |
| SEQ ID NO: 2 | CX3CL1 (fractalkine) |
| SEQ ID NO: 3: | US28 receptor |
| SEQ ID NO: 4 | US27 receptor |
| SEQ ID NO: 5 | UL33 receptor |
| SEQ ID NO: 6 | UL78 receptor |
| SEQ ID NO: 7 | vCCL2 chemokine |
| SEQ ID NO: 8 | Exotoxin A |
| SEQ ID NO: 9 | PE38KDEL |
| SEQ ID NO: 10 | Immunotoxin comprising of Fractalkine pos. 25-397 of SEQ ID NO: 2 and PE38KDEL SEQ ID NO: 9 |
| SEQ ID NO: 11 | Immunotoxin comprising the chemokine part of fraktalkine pos. 25-100 of SEQ ID NO: 2 and PE38KDEL SEQ ID NO: 9 |

The present invention relates to highly specific immunotoxins towards CMV infected cells useful in treating or preventing CMV diseases. The immunotoxins of the invention target constitutively internalizing receptors encoded by CMV and expressed on the surface of the CMV infected cell. Upon binding to the constitutively internalizing receptor the immunotoxin is internalized into the CMV infected cell and subsequently exerts it cytotoxic effect leading to killing of the cell.

CMV encodes several receptors expressed on the surface of the CMV infected cell, among these are chemokine receptors that undergo constitutively internalization, such as US28, US27, UL33 and UL78. A number of high affinity ligands towards US28, are constituents of the infected individuals immune system, the chemokine system. These host immune molecules, the chemokines, can be used as ligands of the immunotoxins of the invention.

The use of chemokine-based immunotoxins has the advantage that they can be effectively internalized after chemokine-mediated receptor activation followed by receptor internalization. However, chemokine-induced receptor internalization requires that the ligand retain agonistic properties, which may have unwanted stimulatory effects on the target cells and interacts with chemokine receptors on normal cells and thereby kill normal cells in addition to the diseased target cells. By designing an immunotoxin with high specificity to receptors encoded by CMV and thus only expressed on CMV infected cells specificity against the target cell of interest is ensured. By further designing an immunotoxin to bind a CMV encoded antigen that undergo constitutively internalization, an efficient uptake of the immunotoxin by the CMV infected cell is ensured, irrespective of the properties of the ligand. Normally, a receptor expressed on the surface of a cell undergoes internalisation into the cell when the receptor is activated by an agonist. However, constitutively internalizing receptors constantly undergo internalisation into the cell without activation by agonists. Thus, by designing an immunotoxin specific towards a constitutively internalizing receptor on the CMV infected cell, an efficient uptake of the immunotoxin into the cell is obtained, and the infected cells can thus be targeted specifically by the immunotoxin without unwanted toxicity and side effects.

Thus, in the broadest aspect the invention relates to an immunotoxin comprising (a) a ligand that binds a constitutively internalizing receptor encoded by CMV and expressed on the CMV infected cell and (b) a toxin that is cytotoxic to the CMV infected cell, wherein the immunotoxin is not SEQ ID NO:1.

Thus, in all embodiments of the present invention, the immunotoxin is not SEQ ID NO:1, i.e. SEQ ID NO:1 is excluded from the scope of this invention.

SEQ ID NO: 1 has been described by Bruhl et al, 2001. It is a fusion protein of the chemokine RANTES and a truncated version of PSEUDOMONAS: exotoxin A. They used SEQ ID NO 1 to target cells expressing the CCR5 receptor. More specifically, they showed that the immunotoxin completely destroyed CCR5(+) Chinese hamster ovary cells at a concentration of 10 nM, whereas no cytotoxic effect was detectable against CCR5(−) Chinese hamster ovary cells. The fusion protein binds to CCR5 and down-modulates the receptor from the cell surface. The chemokine Rantes is also a ligand of US28, but the authors made no suggestions to use the immunotoxin against CMV infected cells.

In the following the ligand of the immunotoxin of the invention is described.

Ligands of the Invention

Ligands of the present invention are polypeptides that bind to the receptors of the invention. The receptors of the invention are CMV encoded constitutively internalizing receptors that are expressed on the surface of the CMV infected cell. The receptors of the invention are described in more details further below.

In one embodiment of the present invention, the ligand is selected from the group consisting of chemokines or variants thereof and antibodies or fragments thereof.

In another embodiment of the present invention, the ligand is a chemokine or a variant thereof.

Chemokines are a large and diverse superfamily of proteins. The superfamily is subdivided into four branches, based upon whether the first two cysteines in the classical chemokine motif are adjacent (the C-C branch comprising the CC-chemokines) or spaced by an intervening residue (the C-X-C branch comprising the CXC-chemokines), or into a branch which lacks one of the two first cysteines in the corresponding motif (the X-C branch comprising the XC-chemokines) or finally into a branch where the first two cysteines are spaced by three intervening residues (the C-X-X-X-C branch comprising the CX$_3$C-chemokines). Chemokines exert their functions through interaction with 7 trans membrane (7TM), G protein-coupled receptors (GPCRs), chemokine receptors. Besides controlling leukocyte migration, chemokines regulate immune system development, control leukocyte homeostasis and inflammation and control activation and differentiation of lymphoid cells. Thus, chemokines are thought to be central in the host immune response to infectious pathogens. Indeed, the significance of controlling the host chemokine system during viral infections is highlighted by the fact that e.g. CMV encodes several proteins known to interfere with the host (e.g. human or mouse) chemokine system.

In one embodiment of the present invention, the ligand is selected from the group consisting of chemokines or variants or fragments thereof originating from human, mouse, rat, rabbit, fowl, pig, horse, rhesus monkey, orang-utan, cow, dog, or virus.

In another embodiment, the ligand is a chemokine selected from the group consisting of CC-chemokines, XC-chemokines, CXC-chemokines and CX$_3$C-chemokines or variants thereof.

In another embodiment the ligand is a chemokine selected from the group consisting of CC-chemokines and CX3C-chemokines or variants thereof.

In still another embodiment, the ligand is a CC-chemokine selected from the group consisting of CCL1, CCL2, CCL3, CCL4, CCL5, CCL6, CCL7, CCL8, CCL9, CCL10, CCL11, CCL12, CCL13, CCL14, CCL15, CCL16, CCL17, CCL18, CCL19, CCL20, CCL21, CCL22, CCL23, CCL24, CCL25, CCL26, CCL27 and CCL28 or variants thereof.

In another embodiment, the ligand is a CC-chemokine selected from the group consisting of CCL2, CCL3, CCL4, CCL5 CCL7, CCL8, CCL11, CCL13, CCL14, CCL16 and CCL22 or variants thereof.

In another embodiment, the ligand is a CC-chemokine selected from the group consisting of, CCL2, CCL3, CCL4, CCL5 and CCL7 or variants thereof.

In another embodiment, the ligand is a CC-chemokine selected from the group consisting of CCL2, CCL3, CCL4 and CCL7 or a variant thereof.

In another embodiment, the ligand is the KSHV encoded CC-chemokines vCCL1 or vCCL2 or a variant thereof.

In another embodiment, the ligand is the KSHV encoded CC-chemokine vCCL2 or a variant thereof.

In a preferred embodiment, the ligand is a CC-chemokine originating from human or mouse.

In another embodiment, the ligand is a CX$_3$C chemokine or a variant thereof.

In another embodiment, the ligand is a variant which has at least 67% amino acid sequence identity to human CX3CL1 (SEQ ID NO:2), such as e.g. 70%, or such as e.g. 75%, or such as e.g. 80%, or such as e.g. 85%, or such as e.g. 90%, or such as e.g. 95%, or such as e.g. 96%, or such as e.g. 97%, or such as e.g. 98%, or such as e.g. 99%, such as e.g. 70%, or such as e.g. 71%, or such as e.g. 72%, or such as e.g. 73%, or such as e.g. 74%, or such as e.g. 75%, or such as e.g. 76%, or such as e.g. 77%, or such as e.g. 78%, or such as e.g. 79%, or such as e.g. 80%, or such as e.g. 81%, or such as e.g. 82%, or such as e.g. 83%, or such as e.g. 84%, or such as e.g. 85%, or such as e.g. 86%, or such as e.g. 87%, or such as e.g. 88%, or such as e.g. 89%, or such as e.g. 90%, or such as e.g. 91%, or such as e.g. 92%, or such as e.g. 93%, or such as e.g. 94%, or such as e.g. 95%, or such as e.g. 96%, or such as e.g. 97%, or such as e.g. 98%, or such as e.g. 99%.

In one aspect, the present invention provides fraktalkine variants having at least about 50%, 60%, 70%, 75%, 80%, 85%, 90%, 91%, 92%, 93%, 94%, 95%, 96%, 97%, 98%, 99%, 99.5% or more percent sequence identity to SEQ ID NO:2, or a fragment thereof.

This invention also encompasses proteins or peptides having substantial amino acid sequence similarity with an amino acid sequence of a CX3CL1 (SEQ ID NO:2). Natural variants include individual, polymorphic, allelic, strain, or species variants.

Naturally species variants of CX3CL1 include:

| Species | Genbank accession number |
|---|---|
| Human | AAH01163 |
| Mouse | AAH54838 |
| RAT | AAH70938 |
| Macaca mulatta (rhesus monkey) | AAN76089 |
| Gallus Gallus | AAH54838 |
| Bos taurus (cow) | XP_585262 |
| Canis familiaris (dog) | XP_851606 |
| Pongo pygmaeus (orang-utan) | CAH91687 |
| Pongo pygmaeus (orang-utan) | CAH90903 |

In another preferred embodiment of the present invention, the ligand is a variant which has at least 67% amino acid sequence identity to the chemokine domain of human CX3CL1 (residues 25-100 of SEQ ID NO:2), such as e.g. 70%, or such as e.g. 75%, or such as e.g. 80%, or such as e.g. 85%, or such as e.g. 90%, or such as e.g. 95%, or such as e.g. 96%, or such as e.g. 97%, or such as e.g. 98%, or such as e.g. 99%, such as e.g. 70%, or such as e.g. 71%, or such as e.g. 72%, or such as e.g. 73%, or such as e.g. 74%, or such as e.g. 75%, or such as e.g. 76%, or such as e.g. 77%, or such as e.g. 78%, or such as e.g. 79%, or such as e.g. 80%, or such as e.g. 81%, or such as e.g. 82%, or such as e.g. 83%, or such as e.g. 84%, or such as e.g. 85%, or such as e.g. 86%, or such as e.g. 87%, or such as e.g. 88%, or such as e.g. 89%, or such as e.g. 90%, or such as e.g. 91%, or such as e.g. 92%, or such as e.g. 93%, or such as e.g. 94%, or such as e.g. 95%, or such as e.g. 96%, or such as e.g. 97%, or such as e.g. 98%, or such as e.g. 99%.

Preferably, the ligand of the immunotoxin binds to the US28 receptor with a Kd of $10^{-8}$ M or less. Even more preferred is a Kd of less than $10^{-9}$ M, such as $10^{-10}$ M, $10^{-11}$ M or $10^{-12}$ M Preferably, the immunotoxin has low affinity for endogenous receptors of the parental ligand. Thus, in a preferred embodiment, the ligand binds to the CX3CR1 receptor with a Kd of $10^{-6}$ M or more. More preferably, the ligand binds to the CX3CR1 receptor with a kd of more than $10^{-5}$ M or $10^{-4}$ M. Specificity towards the US28 receptor can be achieved by appropriate mutations of the parental ligand.

Preferably, the ligand of the immunotoxin selected from the group consisting of the following variants: A variant mutated in position 31 of SEQ ID NO:2, a variant mutated in position 38 of SEQ ID NO:2, a variant mutated in position 42 of SEQ ID NO:2, a variant mutated in position 60 of SEQ ID NO:2, a variant mutated in position 61 of SEQ ID NO:2, a variant mutated in position 68 of SEQ ID NO:2, a variant mutated in position 71 of SEQ ID NO:2, a variant mutated in position 72 of SEQ ID NO:2 and a variant mutated in position 73 of SEQ ID NO:2.

More preferably, the ligand part of the immunotoxin is the selected from the following group of variants of SEQ ID NO:2: A variant K31A mutated in position 31 from a Lysine to an Alanine, a variant K31E mutated in position 31 from a Lysine to an Glutamate, a variant K38A mutated in position 38 from a Lysine to an Alanine, a variant K38E mutated in position 38 from a Lysine to a Glutamate, a variant K42A mutated in position 42 from a Lysine to an Alanine, a variant K42E mutated in position 42 from a Lysine to a Glutamate, a variant K60A mutated in position 60 from a Lysine to a Alanine, a variant K60E mutated in position 60 from a Lysine to a Glutamate, a variant R61A mutated in position 61 from an Arginine to a Alanine, a variant R61E mutated in position 61 from an Arginine to a Glutamate, a variant R68A mutated in position 68 from an Arginine to a Alanine, a variant R68E mutated in position 68 from an Arginine to a Glutamate, a variant R71A mutated in position 71 from an Arginine to a Alanine, a variant R71E mutated in position 71 from an Arginine to a Glutamate, a variant R71Q mutated in position 71 from an Arginine to a Glutamine, a variant L72A mutated in position 72 from a Leucine to a Alanine, a variant F73A mutated in position 73 from a Phenylalanine to a Alanine, a variant F73L mutated in position 73 from a Phenylalanine to a Leucine.

In another embodiment, the ligand comprises the chemokine domain of human CX3CL1 (residues 25-100 of SEQ ID NO:2) wherein one or more amino acid residues in position 33, 34 and 35 (of seq ID NO:2) have been mutated or deleted.

In a preferred embodiment, position 33 of SEQ ID NO:2 have been mutated from aa to aa1, aa2, aa3, aa4 or aa5 or has been deleted.

In a preferred embodiment, position 34 of SEQ ID NO:2 have been mutated from aa to aa1, aa2, aa3, aa4 or aa5 or has been deleted.

In a preferred embodiment, position 35 of SEQ ID NO:2 have been mutated from aa to aa1, aa2, aa3, aa4 or aa5 or has been deleted.

Mutation of residues 33, 34 and 35 is desirable to give the immunotoxin selectivity, binding to CMV encoded receptors without binding to endogenous chemokine receptors.

The ligand of the invention may also be a virus encoded chemokine. One such preferred chemokine is the Kaposis Sarcoma associated herpesvirus (KSHV) encoded CC-chemokine vCCL2 (SEQ ID NO:7) or a variants thereof.

Chimeras

The present invention also provides ligands that are recombinant polypeptides or proteins comprising segments from different chemokines, e.g. CC-chemokines, XC-chemokines, CXC-chemokines and $CX_3C$-chemokines. Thus, the invention relates to a ligand which is a heterologous fusion protein comprising two or more segments from a CC-chemokine, a XC-chemokine, a CXC-chemokine or a CX3C-chemokine, such as e.g. CX3CL1 (fractalkine) or the chemokine domain of fractalkine. The chimeric polypeptides of the invention exhibiting new combinations of specificities, such as receptor specificities, will result from the functional linkage of protein-binding specificities and other functional domains. Thus, the ligand of the invention may be a chimera between two or more different chemokines, wherein the chemokines are selected from the group consisting of CC-chemokines, XC-chemokines, CXC-chemokines and $CX_3C$-chemokines.

More specifically, the ligand may be a chimera between two or more different chemokines, wherein the chemokines are CC-chemokines selected from the group consisting of CCL1, CCL2, CCL3, CCL4, CCL5, CCL6, CCL7, CCL8, CCL9, CCL10, CCL11, CCL12, CCL13, CCL14, CCL15, CCL16, CCL17, CCL18, CCL19, CCL20, CCL21, CCL22, CCL23, CCL24, CCL25, CCL26, CCL27, CCL28 and vCCL1 or vCCL2 or variants or truncated forms thereof.

The ligand may also be a chimera between one or more CC-chemokines or variants thereof and one or more CX3C-chemokines or variants thereof. In this embodiment, the CC-chemokines may be selected from the group consisting of CCL1, CCL2, CCL3, CCL4, CCL5, CCL6, CCL7, CCL8, CCL9, CCL10, CCL11, CCL12, CCL13, CCL14, CCL15, CCL16, CCL17, CCL18, CCL19, CCL20, CCL21, CCL22, CCL23, CCL24, CCL25, CCL26, CCL27, CCL28 and vCCL2 or variants thereof, and the CX3C-chemokines may be selected from the group consisting of CX3CL1 (SEQ ID NO:2) or variants thereof and the chemokine domain of CX3CL1 (residues 25-100 of SEQ ID NO:2) or variants thereof.

In a preferred embodiment, the ligand is a chimera between vCCL2 (SEQ ID NO:7) and CX3CL1 (SEQ ID NO:2).

More specifically, the ligand may be a chimera between a series of amino acids, such as e.g. 2 (LG) or such as e.g. 3 or such as e.g. 4 or such as e.g. 5 or such as e.g. 6 or such as e.g. 7 or such as e.g. 8 or such as e.g. 9 or such as e.g. 10 or such as e.g. 11 or such as e.g. 12 encoding the N-terminal part of vCCL2 (residues 1-5 or 1-9 or 1-12 of SEQ ID NO:7) replacing the N-terminal part of CX3CL1 (residues 25-31 or 25-36 of SEQ ID NO:2)

Antibodies of the Invention

As outlined above, immunotoxins contain a targeting moiety (a ligand) for delivery and a toxic moiety for cytotoxicity. The targeting moiety can be either receptor ligands such as e.g. cytokines or growth factors, soluble receptors and antibodies, such as e.g. polyclonal or monoclonal antibodies. Thus, in one embodiment of the present invention, the ligand of the immunotoxin of the invention is an antibody or a variant thereof. The antibodies of the invention may be polyclonal or monoclonal. The antibody of the invention or fragment thereof can be selected from the group consisting of an antibody against US28, an antibody against US27, an antibody against UL33 and an antibody against UL78. In a preferred embodiment of the invention, the ligand is an antibody against US28.

As is known by the person skilled in the art, specific and high-affinity antibodies can be generated by a number of techniques known in the art. The antibodies may be polyclonal or monoclonal. Monoclonal antibodies may be generated using hybridoma technology. Preferred antibodies are humanized antibodies or human antibodies against US28, US27, UL33 or UL78.

The term antibody is used to mean whole antibodies and binding fragments thereof. The recognized immunoglobulin genes include the kappa, lambda, alpha, gamma, delta, epsilon and mu constant region genes, as well as myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively. A typical immunoglobulin (e.g., antibody) structural unit comprises a tetramer. Each tetramer is composed of two identical pairs of polypeptide chains, each pair having one “light” (about 25 KDa) and one “heavy” chain (about 50-70 KDa). The N-terminus of each chain defines a variable region of about 100 to 110 or more amino acids primarily responsible for antigen recognition. The terms variable light chain (VL) and variable heavy chain (VH) refer to these light and heavy chains, respectively.

Antibodies exist as intact immunoglobulins or as a number of well characterized fragments produced by digestion with various peptidases. Thus, for example, pepsin digests an antibody below the disulfide linkages in the hinge region to produce F(ab)'2, a dimer of Fab which itself is a light chain joined to VH-CH1 by a disulfide bond. The F(ab)'2 may be reduced under mild conditions to break the disulfide linkage in the hinge region thereby converting the $(Fab')_2$ dimer into an Fab' monomer. The Fab' monomer is essentially an Fab with part of the hinge region. The Fc portion of the antibody molecule corresponds largely to the constant region of the immunoglobulin heavy chain, and is responsible for the antibody’s effector function (see, Fundamental Immunology, W. E. Paul, ed., Raven Press, N.Y. (1993), for a more detailed description of other antibody fragments). While various antibody fragments are defined in terms of the digestion of an intact antibody, one of skill will appreciate that such Fab' fragments may be synthesized de novo either chemically or by utilizing recombinant DNA methodology. Thus, the term antibody, as used herein also includes antibody fragments either produced by the modification of whole antibodies or synthesized de novo using recombinant DNA methodologies.

Antibodies also include single-armed composite monoclonal antibodies, single chain antibodies, including single chain Fv (sFv) antibodies in which a variable heavy and a variable light chain are joined together (directly or through a peptide linker) to form a continuous polypeptide, as well as diabodies, tribodies, and tetrabodies (Pack et al. (1995) J Mol Biol 246:28; Biotechnol 11:1271; and Biochemistry 31:1579). The antibodies are, e.g., polyclonal, monoclonal, chimeric, humanized, single chain, Fab fragments, fragments produced by an Fab expression library, or the like.

Affinity

In one embodiment, the ligand of the invention binds to the receptor of the invention, e.g. US28, US27, UL33 or UL78 with a specific binding affinity of at least $10^{-6}$ M, such as e.g. $10^{-7}$ M, or such as e.g. $10^{-8}$ M, or such as e.g. $10^{-9}$ M, or such as e.g. $10^{-10}$ M, or such as e.g. $10^{-11}$ M, or such as $10^{-12}$ M.

A “specific binding affinity” between two molecules, e.g., a ligand and a receptor, means a preferential binding of one molecule for another in a mixture of molecules. The binding of the molecules is typically considered specific if the binding affinity is about $1\times10^4$ $M^{-1}$ to about $1\times10^9$ $M^{-1}$ or greater (i.e., $K_D$ Of about $10^{-4}$ to $10^{-9}$ M or less). Binding affinity of a ligand and a receptor may be measured by standard techniques known to those of skill in the art. Non-limiting examples of well-known techniques for measuring binding affinities include Biacore® technology (Biacore AB, Sweden), isothermal titration microcalorimetry (MicroCal LLC, Northampton, Mass. USA), ELISA, and FACS. For example, FACS or other sorting methods may be used to select for populations of molecules (such as for example, cell surface-displayed ligands) which specifically bind to the associated binding pair member (such as a receptor, e.g., a soluble receptor). Ligand-receptor complexes may be detected and sorted e.g., by fluorescence (e.g., by reacting the complex with a fluorescent antibody that recognizes the complex). Molecules of interest which bind an associated binding pair member (e.g., receptor) are pooled and re-sorted in the presence of lower concentrations of receptor. By performing multiple rounds sorting in the presence of decreasing concentrations of receptor (an exemplary concentration range being on the order of $10^{-6}$ M down to $10^{-9}$ M, i.e., 1 micromolar (μM) down to 1 nanomolar (nM), or less, depending on the nature of the ligand-receptor interaction), populations of the molecule of interest exhibiting specific binding affinity for the receptor may be isolated.

A polypeptide, nucleic acid, or other component is “isolated” when it is partially or completely separated from components with which it is normally associated (other peptides, polypeptides, proteins (including complexes, e.g., polymerases and ribosomes which may accompany a native sequence), nucleic acids, cells, synthetic reagents, cellular contaminants, cellular components, etc.), e.g., such as from other components with which it is normally associated in the cell from which it was originally derived. A polypeptide, nucleic acid, or other component is isolated when it is partially or completely recovered or separated from other components of its natural environment such that it is the predominant species present in a composition, mixture, or collection of components (i.e., on a molar basis it is more abundant than any other individual species in the composition). In some instances, the preparation consists of more than about 60%, 70% or 75%, typically more than about 80%, or preferably more than about 90% of the isolated species.

Toxin of the Invention

The toxic moiety of an immunotoxin mediates the killing of the target cell. Most commonly, the toxin is derived from either bacteria (e.g. *Pseudomonas* exotoxin (PE) (SEQ ID NO: 8) or diphtheria toxin (DT), or plants (e.g. recin or abrin). Both toxin types kill the cells by inhibiting protein synthesis. PE and DT inactivate the elongation factor 2 (EF2) and recin and abrin inactivate the EF2 binding site on the 28S ribosomal subunit.

Any cytotoxic toxin may be useful in the present invention. However, considerations factors such as immunogenicity, feasibility of production, side effects etc. may be taken into account. In one embodiment of the present invention, preferred toxins are selected from the group consisting of gelonin, bouganin, saporin, ricin, ricin A chain, bryodin, diphtheria, restrictocin, diphtheria toxin, *Pseudomonas* exotoxin A and variants thereof.

In a preferred embodiment, the toxin is *Pseudomonas* exotoxin A or a variant thereof.

In yet a preferred embodiment, the toxin of the immunotoxin of the invention is a recombinant toxin comprising a 38-kDa mutant form of PE called PE38 KDEL (SEQ ID NO: 9). Naturally, PE is a 66-kDa protein composed of three domains: a binding domain, a translocation domain, and an ADP-ribosylating domain. Recombinant immunotoxins are made by deleting the cell-binding domain of PE and replacing it with another targeting moiety, in our case the ligand of the invention e.g. a chemokine derivative with high affinity for constitutively internalizing CMV GPCRs.

Thus, the pseudomonas exotoxin PE38 consist of the translocation domain (domain II, amino acid sequence consisting of positions 253-364 of SEQ ID NO:8), a portion of domain 1b (amino acid sequence consisting of positions 381-399 of SEQ ID NO:8) and the ADP-ribosylation domain (domain III, amino acids 400-612) according to Genbank accession no. K01397.

An immunotoxin comprising *Pseudomonas* exotoxin A may be prepared using the methods outlined in the appended examples. These methods may be adapted for the preparation of other immunotoxin. In these, a translational fusion is made between the ligand and the toxin part of the immunotoxin.

A preferred immunotoxin of the invention is SEQ ID NO:10.

Also preferred is an immunotoxin comprising SEQ ID NO:11.

Variants

The invention also encompasses variants and fragments of the preferred polypeptides of the invention. More specifically, the invention encompasses variants of the immunotoxins of the invention, variants of the ligand part of the immunotoxins of the invention and variants of the toxin part of the immunotoxins of the invention. In one particular embodiment, the variant is a fragment of a preferred polypeptide of the invention.

Variants may be naturally occurring or artificially created, e.g. by genetic engineering. Furthermore, variants may be functional variants in which case the functionality is defined with regards to the function of the preferred polypeptides of the invention. Thus, a functional variant of a ligand is a variant, which can bind to the receptors of the invention. A particular preferred functional variant of a ligand is a variant that can bind to the CMV encoded constitutively internalizing receptor, such as a human CMV encoded chemokine receptor, such as e.g. the US28, US27, UL33 or UL78 receptor.

Modification and changes may be made in the structure of the polypeptides of the present invention and DNA segments which encode them and still obtain a functional variant that encodes a protein or peptide with desirable characteristics. The following is a discussion based upon changing the amino acids of a protein to create a functional variant, or even an improved, second-generation molecule. The amino acid changes may be achieved by changing the codons of the DNA sequence, according to the genetic code.

Since it is the interactive capacity and nature of a protein that defines that protein's biological functional activity, certain amino acid sequence substitutions can be made in a protein sequence, and, of course, its underlying DNA coding sequence, and nevertheless obtain a protein with like properties. It is thus contemplated by the inventors that various changes may be made in the polypeptides the invention or corresponding DNA sequences which encode said peptides, without appreciable loss of their biological utility or activity.

In making such changes, the hydropathic index of amino acids may be considered. The importance of the hydropathic amino acid index in conferring interactive biologic function on a protein is generally understood in the art (Kyte and Doolittle, 1982). It is accepted that the relative hydropathic character of the amino acid contributes to the secondary structure of the resultant protein, which in turn defines the interaction of the protein with other molecules, for example, enzymes, substrates, receptors, DNA, antibodies, antigens, and the like. Each amino acid has been assigned a hydropathic index on the basis of their hydrophobicity and charge characteristics (Kyte and Doolittle, 1982), these are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

It is known in the art that certain amino acids may be substituted by other amino acids having a similar hydropathic index or score and still result in a protein with similar biological activity, ie. still obtain a biological functionally equivalent protein. In making such changes, the substitution of amino acids whose hydropathic indices are within ±2 is preferred, those, which are within ±1, are particularly preferred, and those within ±0.5 are even more particularly preferred. It is also understood in the art that the substitution of like amino acids can be made effectively on the basis of hydrophilicity. U.S. Pat. No. 4,554,101, incorporated herein by reference, states that the greatest local average hydrophilicity of a protein, as governed by the hydrophilicity of its adjacent amino acids, correlates with a biological property of the protein.

As detailed in U.S. Pat. No. 4,554,101, the following hydrophilicity values have been assigned to amino acid residues: arginine (+3.0); lysine (+3.0); aspartate (+3.0±1); glutamate (+3.0±1); serine (+0.3); asparagine (+0.2); glutamine (+0.2); glycine (0); threonine (−0.4); proline (−0.5±1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4). It is understood that an amino acid can be substituted for another having a similar hydrophilicity value and still obtain a biologically equivalent, and in particular, an immunologically equivalent protein. In such changes, the substitution of amino acids whose hydrophilicity values are within ±2 is preferred, those which are within +1 are particularly preferred, and those within ±0.5 are even more particularly preferred.

As outlined above, amino acid substitutions are generally therefore based on the relative similarity of the amino acid side-chain substituents, for example, their hydrophobicity, hydrophilicity, charge, size, and the like. Exemplary substitutions which take several of the foregoing characteristics into consideration are well known to those of skill in the art and include: arginine and lysine; glutamate and aspartate; serine and threonine; glutamine and asparagine; and valine, leucine and isoleucine.

Variants may be described by their sequence similarity or sequence identity to a predetermined sequence. In a preferred embodiment, the predetermined sequence is the sequence of the polypeptides of the invention.

To determine the percent sequence identity of two amino acid sequences or of two nucleic acids, the sequences are aligned for optimal comparison purposes (e.g., gaps can be introduced in the sequence of a first amino acid or nucleic acid sequence for optimal alignment with a second amino or nucleic acid sequence). The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position. The percent identity between the two sequences is a function of the number of identical positions shared by the sequences. In one embodiment the two sequences are the same length.

A degree of "sequence identity" of amino acid sequences is a function of the number of identical amino acids at positions shared by the amino acid sequences. A degree of "sequence similarity" of amino acid sequences is a function of the number of amino acids, i.e. structurally related, at positions shared by the amino acid sequences. Sequence identity is determined by sequence comparison algorithms as described above or by visual inspection.

Preferably, residue positions in variants of the present invention differ by conservative amino acid substitutions as compared to the preferred polypeptides of the invention.

Conservative amino acid substitution as used herein relates to the substitution of one amino acid (within a predetermined group of amino acids) for another amino acid (within the same group), wherein the amino acids exhibit similar or substantially similar characteristics.

Within the meaning of the term "conservative amino acid substitution" as applied herein, one amino acid may be substituted for another within the groups of amino acids indicated herein below:
  Amino acids having polar side chains (Asp, Glu, Lys, Arg, His, Asn, Gln, Ser, Thr, Tyr, and Cys)
  Amino acids having non-polar side chains (Gly, Ala, Val, Leu, Ile, Phe, Trp, Pro, and Met)
  Amino acids having aliphatic side chains (Gly, Ala Val, Leu, Ile)
  Amino acids having cyclic side chains (Phe, Tyr, Trp, His, Pro)
  Amino acids having aromatic side chains (Phe, Tyr, Trp)
  Amino acids having acidic side chains (Asp, Glu)
  Amino acids having basic side chains (Lys, Arg, His)
  Amino acids having amide side chains (Asn, Gln)
  Amino acids having hydroxy side chains (Ser, Thr)
  Amino acids having sulphor-containing side chains (Cys, Met),
  Neutral, weakly hydrophobic amino acids (Pro, Ala, Gly, Ser, Thr)
  Hydrophilic, acidic amino acids (Gln, Asn, Glu, Asp), and
  Hydrophobic amino acids (Leu, Ile, Val)

Preferred conservative amino acids substitution groups are: valine-leucine-isoleucine, phenylalanine-tyrosine, lysine-arginine, alanine-valine, and asparagine-glutamine.

In one embodiment of the invention, a variant includes non-natural amino acids such D-amino acids, beta-amino or L-amino acids with non-natural side groups. Such non-natural amino acids may be desirable to optimize the binding of the variant to its receptor, increase toxicity, decrease side effects, optimize the pharmacokinetics of the variant etc.

Accordingly, a variant or a fragment thereof according to the invention may comprise, within the same variant of the sequence or fragments thereof, or among different variants of the sequence or fragments thereof, at least one substitution, such as a plurality of substitutions introduced independently of one another.

It is clear from the above outline that the same variant or fragment thereof may comprise more than one conservative amino acid substitution from more than one group of conservative amino acids as defined herein above.

A functional variant as used in the present invention is according to one preferred embodiment established by means of reference to the corresponding functionality of a predetermined polypeptide of the invention.

In one embodiment of the invention, all functional variants of SEQ ID NO:2 (CX3CL1) are included within the scope of this invention, regardless of the degree of identity or similarity that they show to SEQ ID NO:2. The reason for this is that some regions of SEQ ID NO:2 are most likely readily mutatable, or capable of being completely deleted, without any significant effect on the binding activity of the resulting fragment.

A functional variant obtained by substitution may well exhibit some form or degree of activity, and yet have less sequence identity, if residues containing functionally similar amino acid side chains are substituted. Functionally similar in this respect refers to dominant characteristics of the side chains such as hydrophobic, basic, neutral or acidic, or the presence or absence of steric bulk. Accordingly, in one embodiment of the invention, the degree of sequence identity is not a principal measure of a variant being a functional variant of a preferred polypeptide according to the present invention.

Whether a variant is a functional variant can be determined by assays. E.g. a functionality of a ligand may be determined by a functional parameter such as ability to bind a predetermined receptor of the invention. Receptor binding can be determined by competition binding assay, saturation binding assay, fluorescence polarization assay, biacore assay and surface plasmon resonance based assay such outlined in the appended examples.

Functionality of immunotoxin variants may be determined in a biological assay, e.g. based on toxicity to a CMV infected cell such as outlined in the appended examples.

The function of a functional variant thus depends on the context.

The Receptor

The CMV genome comprises several genes (e.g. US28, US27, UL33 and UL78) encoding 7 transmembrane receptors, at least US28 being a functional chemokine receptors. These receptors are expressed on the surface of the CMV infected cell and become capable of responding to chemokines in the environment. Because the virus on its own is inherently non-motile, and because chemokines and their receptors encoded by human cells are known to regulate the migration of leukocytes and other cells through the body, CMV encoded chemokine receptors are thought to be encoded by the virus to facilitate the dissemination of CMV through the body during and after infection.

As the CMV encoded chemokines receptors are expressed on the CMV infected cells, these receptors are useful as a target for immunotoxins against CMV infected cells.

By immunogold electron microscopy US28 is seen mostly to localize to multivesicular endosomes. A minor portion of the protein (at most 20%) is also expressed at the cell surface. Antibody-feeding experiments indicate that cell surface US28 undergoes constitutive ligand-independent endocytosis. Further biochemical analysis with the use of iodinated ligands show that US28 was rapidly internalized.

When expressed in the absence of other HCMV proteins, tagged US28 molecules are located mostly intracellularly. The localization of US28 significantly overlaps with markers for early endosomes and late endosomes/lysosomes, suggesting that this viral protein is located at least in part in the endocytic pathway. By electron microscopy of immunogold labeled US28-GFP in ultrathin frozen sections, the protein is seen to be associated with multivesicular bodies that have the characteristics of late endosomes and can be labeled with antibodies to the late endosome markers CD63 and lyso bisphosphatidic acid. Labeling of US28-GFP is seen on both the limiting membrane of these structures and on the internal vesicles. In addition, US28-GFP is located to some extent at the plasma membrane and in small tubules and vesicles that could correspond to early endosomes.

It is found that this cell surface US28 undergoes rapid constitutive endocytosis and recycling. The rate of internalization is 7% of the cell surface pool per minute, and after 60 min up to 90% of the initial surface pool is intracellular. These internalization properties are similar to those of activated chemokine receptors. It has previously been demonstrated that both phorbol esters and SDF-1 induce endocytosis of the cellular chemokine receptor CXCR4. The kinetics of US28 endocytosis is similar to those seen for SDF-1-induced internalization of CXCR4 and significantly faster than phorbol ester-induced uptake. The rapid endocytosis of US28 is not affected by the ligand RANTES or by binding of the bivalent tracer antibody Q4120, which has the potential to cross-link US28 receptors. The fact that cells maintain a constant level of US28 at the cell surface, while constitutive endocytosis occurs, suggests that internalized US28 is recycled. Cycloheximide treatment does not significantly deplete cell surface US28. Moreover, recycling is demonstrated directly in antibody-feeding experiments. Interestingly, antibody molecules internalized on CD4-US28 can be seen in multivesicular endosomes by immunolabeling cryosections of antibody-treated CD4-US28 cells suggesting that the multivesicular body pool of US28 may be part of the recycling itinerary. In this respect the recycling pathway of US28 may be similar to that described for the lysosomal tetraspanin CD63, which is also found on the internal membranes of multivesicular bodies but is able to recycle via the plasma membrane. It has been shown that US28 internalizes extracellular chemokines, suggesting that this viral chemokine receptor may be able to sequester CC and CX3C-chemokines from the environment of HCMV-infected cells. Constitutive endocytosis will probably occur for any ligand that binds US28. Once internalized, the ligand may dissociate from the receptor in early or late endosomes and eventually be degraded.

CMV harbors in its genome several genes encoding constitutively internalizing GPCRs, such as e.g. US28, US27, UL33 and UL78. Thus, in one embodiment of the present invention, the receptor which is the target of the immunotoxin of the invention is selected from the group consisting of human CMV proteins US28 (SEQ ID NO:3), US27 (SEQ ID NO:4), UL33 (SEQ ID NO:5) and UL28 (SEQ ID NO:6) or naturally occurring variants thereof.

US28 is an open reading frame (ORF) which encodes a protein that acts as a functional receptor for certain human and viral chemokines. Upon infection of a cell by CMV, US28 is expressed on the surface of the infected cell and becomes capable of responding to chemokines in the environment. The US28 receptor has been shown to bind a variety of human, murine, and virus-encoded CC chemokines in a variety of assay formats. In addition, the CX3C chemokine, Fractalkine (also termed CX3CL1), binds with a very high affinity (KI50 pM) to US28. Fractalkine is expressed on certain endothelial cell surfaces and on populations of dendritic cells (DC), and may thus define a portal through which CMV infected cells go from the circulation to the tissue space, as well as find residence in the DC. In a preferred embodiment, the receptor is US28 or naturally occurring variants thereof.

US28 is a constitutively internalizing receptor. Thus chemokines or other compounds that binds US28 are internalized into the cell that express the receptor. Likewise, an immunotoxin that binds to US28 will be transported in the CMV infected cell, where the toxin can exert its cytotoxic function.

Several studies have shown, that US28 can signal in response to ligand binding. Other studies have shown that US28 is constitutively active. In the present context the term "a constitutively active G protein coupled" relates to a G protein coupled receptor that mediates a signal without activation by a receptor ligand (agonist). An active GPCR bind to at least one active G protein. A G protein is active when it is bound to GTP. Hydrolysis of GTP to GDP regenerates the resting state of the G protein.

The gene encoding the US28 protein is localized to human cytomegalovirus open reading frame (ORF) US28 according to common annotation of the human cytomegalovirus (CMV) genome also known as Human herpesvirus 5 (HHV5) (laboratory strain AD169), complete genome Genbank accession NC_001347.

The sequence of human CMV varies from isolate to isolate, thus there exist multiple genomic variants of US28. Likewise for US27, UL33 and UL78 and it is to be understood that the terms US28, US27, UL33 and UL78, when used in the present invention, include all naturally occurring variants of the CMV encoded proteins.

The following list provides accession number to 94 US28 amino acid sequences available in Genbank.
T09353
G protein-coupled receptor—human cytomegalovirus (isolate VHL/E)
gi|7441615|pir||T09353[7441615]
P69333
G-protein coupled receptor homolog US28 (HHRF3)
gi|59800435|sp|P69333|US28_HCMVT[59800435]
P69332
G-protein coupled receptor homolog US28 (HHRF3)
gi|59800434|sp|P69332|US28_HCMVA[59800434]
NP_783808
US28 [Human herpesvirus 5 strain AD169]
gi|28373231|ref|NP_783808.1|[28373231]
YP_081612
US28 [Human herpesvirus 5 strain Merlin]
gi|52139337|ref|YP_081612.1|[52139337]
AAR31716
US28 [Human herpesvirus 5]
gi|39842172|gb|AAR31716.1|[39842172]
AAS49025
US28 [Human herpesvirus 5]

gi|44903346|gb|AAS49025.1|[44903346]
AAO22978
US28 protein [Human herpesvirus 5]
gi|27805022|gb|AAO22978.1|[27805022]
AAO22977
US28 protein [Human herpesvirus 5]
gi|27805020|gb|AAO22977.1|[27805020]
AAO22976
US28 protein [Human herpesvirus 5]
gi|27805018|gb|AAO22976.1|[27805018]
AAO22975
US28 protein [Human herpesvirus 5]
gi|27805016|gb|AAO22975.1|[27805016]
AAO22974
US28 protein [Human herpesvirus 5]
gi|27805014|gb|AAO22974.1|[27805014]
AAO22973
US28 protein [Human herpesvirus 5]
gi|27805012|gb|AAO22973.1|[27805012]
AAO22972
US28 protein [Human herpesvirus 5]
gi|27805010|gb|AAO22972.1|[27805010]
AAO22971
US28 protein [Human herpesvirus 5]
gi|27805008|gb|AAO22971.1|[27805008]
AAO22970
US28 protein [Human herpesvirus 5]
gi|27805006|gb|AAO22970.1|[27805006]
AAO22969
US28 protein [Human herpesvirus 5]
gi|27805004|gb|AAO22969.1|[27805004]
AAO22968
US28 protein [Human herpesvirus 5]
gi|27805002|gb|AAO22968.1|[27805002]
AAO22967
US28 protein [Human herpesvirus 5]
gi|27805000|gb|AAO22967.1|[27805000]
AAO22966
US28 protein [Human herpesvirus 5]
gi|27804998|gb|AAO22966.1|[27804998]
AAO22965
US28 protein [Human herpesvirus 5]
gi|27804996|gb|AAO22965.1|[27804996]
AAO22964
US28 protein [Human herpesvirus 5]
gi|27804994|gb|AAO22964.1|[27804994]
AAO22963
US28 protein [Human herpesvirus 5]
gi|27804992|gb|AAO22963.1|[27804992]
AAO22962
US28 protein [Human herpesvirus 5]
gi|27804990|gb|AAO22962.1|[27804990]
AAO22961
US28 protein [Human herpesvirus 5]
gi|27804988|gb|AAO22961.1|[27804988]
AAO22960
US28 protein [Human herpesvirus 5]
gi|27804986|gb|AAO22960.1|[27804986]
AAO22959
US28 protein [Human herpesvirus 5]
gi|27804984|gb|AAO22959.1|[27804984]
AAO22958
US28 protein [Human herpesvirus 5]
gi|27804982|gb|AAO22958.1|[27804982]
AAO22957
US28 protein [Human herpesvirus 5]
gi|27804980|gb|AAO22957.1|[27804980]
AAO22956
US28 protein [Human herpesvirus 5]
gi|27804978|gb|AAO22956.1|[27804978]
AAO22955
US28 protein [Human herpesvirus 5]
gi|27804976|gb|AAO22955.1|[27804976]
AAO22954
US28 protein [Human herpesvirus 5]
gi|27804974|gb|AAO22954.1|[27804974]
AAN37944
US28 [Human herpesvirus 5]
gi|23507087|gb|AAN37944.1|[23507087]
AAN37943
US28 [Human herpesvirus 5]
gi|23507085|gb|AAN37943.1|[23507085]
AAN37942
US28 [Human herpesvirus 5]
gi|23507083|gb|AAN37942.1|[23507083]
CAD37475
unnamed protein product [Human herpesvirus 5]
gi|21690728|emb|CAD37475.1|[21690728]
CAD37474
unnamed protein product [Human herpesvirus 5]
gi|21690726|emb|CAD37474.1|[21690726]
AAK58045
glycoprotein coupled receptor [human herpesvirus 5]
gi|14269387|gb|AAK58045.1|AF378924_1|[14269387]
AAK58044
glycoprotein coupled receptor [human herpesvirus 5]
gi|14269385|gb|AAK58044.1|AF378923_1|[14269385]
AAK58043
glycoprotein coupled receptor [human herpesvirus 5]
gi|14269383|gb|AAK58043.1|AF378922_1|[14269383]
AAK58042
glycoprotein coupled receptor [human herpesvirus 5]
gi|14269381|gb|AAK58042.1|AF378921_1|[14269381]
AAK58041
glycoprotein coupled receptor [human herpesvirus 5]
gi|14269379|gb|AAK58041.1|AF378920_1|[14269379]
AAK58040
glycoprotein coupled receptor [human herpesvirus 5]
gi|14269377|gb|AAK58040.1|AF378919_1|[14269377]
AAK58039
glycoprotein coupled receptor [human herpesvirus 5]
gi|4269375|gb|AAK58039.1|AF378918_1|[14269375]
AAK58038
glycoprotein coupled receptor [human herpesvirus 5]
gi|4269373|gb|AAK58038.1|AF378917_1|[14269373]
AAK58037
glycoprotein coupled receptor [human herpesvirus 5]
gi|4269371|gb|AAK58037.1|AF378916_1|[14269371]
AAK58036
glycoprotein coupled receptor [human herpesvirus 5]
gi|4269369|gb|AAK58036.1|AF378915_1|[14269369]
AAK58035
glycoprotein coupled receptor [human herpesvirus 5]
gi|14269367|gb|AAK58035.1|AF378914_1|[14269367]
AAK58034
glycoprotein coupled receptor [human herpesvirus 5]
gi|14269365|gb|AAK58034.1|AF378913_1|[14269365]
AAK58033
glycoprotein coupled receptor [human herpesvirus 5]
gi|14269363|gb|AAK58033.1|AF378912_1|[14269363]
AAK58032
glycoprotein coupled receptor [human herpesvirus 5]
gi|14269361|gb|AAK58032.1|AF378911_1|[14269361]
AAK58031 glycoprotein coupled receptor [human herpesvirus 5]
gi|14269359|gb|AAK58031.1|AF378910_1|[14269359]
AAK58030
glycoprotein coupled receptor [human herpesvirus 5]
gi|14269357|gb|AAK58030.1|AF378909_1|[14269357]
AAK54384
chemokine receptor US28 [human herpesvirus 5]
gi|14192717|gb|AAK54384.1|[14192717]
CAC38860
glycoprotein coupled receptor [Human herpesvirus 5]
gi|14140086|emb|CAC38860.1|[14140086]
CAC38859
glycoprotein coupled receptor [Human herpesvirus 5]
gi|14140084|emb|CAC38859.1|[14140084]
CAC38858
glycoprotein coupled receptor [Human herpesvirus 5]
gi|14140082|emb|CAC38858.1|[14140082]
CAC38857
glycoprotein coupled receptor [Human herpesvirus 5]
gi|14140080|emb|CAC38857.1|[14140080]
CAC38856
glycoprotein coupled receptor [Human herpesvirus 5]
gi|14140078|emb|CAC38856.1|[14140078]
CAC38855
glycoprotein coupled receptor [Human herpesvirus 5]
gi|14140076|emb|CAC38855.1|[14140076]
CAC38854
glycoprotein coupled receptor [Human herpesvirus 5]
gi|14140074|emb|CAC38854.1|[14140074]
CAC38853
glycoprotein coupled receptor [Human herpesvirus 5]
gi|14140072|emb|CAC38853.1|[14140072]
CAC38852
glycoprotein coupled receptor [Human herpesvirus 5]
gi|14140070|emb|CAC38852.1|[14140070]
CAC38851
glycoprotein coupled receptor [Human herpesvirus 5]
gi|4140068|emb|CAC38851.1|[14140068]
CAC38850
glycoprotein coupled receptor [Human herpesvirus 5]
gi|14140066|emb|CAC38850.1|[14140066]
CAC38849
glycoprotein coupled receptor [Human herpesvirus 5]
gi|14140064|emb|CAC38849.1|[14140064]
CAC38848
glycoprotein coupled receptor [Human herpesvirus 5]
gi|14140062|emb|CAC38848.1|[14140062]
CAC38847
glycoprotein coupled receptor [Human herpesvirus 5]
gi|14140060|emb|CAC38847.1|[14140060]
CAC38846
glycoprotein coupled receptor [Human herpesvirus 5]
gi|4140058|emb|CAC38846.1|[14140058]
CAC38845
glycoprotein coupled receptor [Human herpesvirus 5]
gi|14140056|emb|CAC38845.1|[14140056]
CAC38844
glycoprotein coupled receptor [Human herpesvirus 5]
gi|14140054|emb|CAC38844.1|[14140054]
CAC37929
chemokine receptor homologue [Human herpesvirus 5]
gi|13940276|emb|CAC37929.1|[13940276]
CAC37945
chemokine receptor homologue [Human herpesvirus 5]
gi/13940308|emb|CAC37945.1|[13940308]
CAC37944
chemokine receptor homologue [Human herpesvirus 5]
gi|13940306|emb|CAC37944.1|[13940306]
CAC37943
chemokine receptor homologue [Human herpesvirus 5]
gi|13940304|emb|CAC37943.1|[13940304]
CAC37942
chemokine receptor homologue [Human herpesvirus 5]
gi|13940302|emb|CAC37942.1|[13940302]
CAC37941
chemokine receptor homologue [Human herpesvirus 5]
gi|13940300|emb|CAC37941.1|[13940300]
CAC37940
chemokine receptor homologue [Human herpesvirus 5]
gi|13940298|emb|CAC37940.1|[13940298]
CAC37939
chemokine receptor homologue [Human herpesvirus 5]
gi|13940296|emb|CAC37939.1|[13940296]
CAC37938
chemokine receptor homologue [Human herpesvirus 5]
gi|13940294|emb|CAC37938.1|[13940294]
CAC37937
chemokine receptor homologue [Human herpesvirus 5]
gi|13940292|emb|CAC37937.1|[13940292]
CAC37936
chemokine receptor homologue [Human herpesvirus 5]
gi|13940290|emb|CAC37936.1|[13940290]
CAC37935
chemokine receptor homologue [Human herpesvirus 5]gi|13940288|emb|CAC37935.1|[13940288]
CAC37934
chemokine receptor homologue [Human herpesvirus 5]
gi|13940286|emb|CAC37934.1|[13940286]
CAC37933
chemokine receptor homologue [Human herpesvirus 5]
gi|13940284|emb|CAC37933.1|[13940284]
CAC37932
chemokine receptor homologue [Human herpesvirus 5]
gi|13940282|emb|CAC37932.1|[13940282]
CAC37931
chemokine receptor homologue [Human herpesvirus 5]
gi|13940280|emb|CAC37931.1|[13940280]
CAC37930
chemokine receptor homologue [Human herpesvirus 5]
gi|13940278|emb|CAC37930.1|[13940278]
AAF78286
G protein-coupled receptor [human herpesvirus 5]
gi|8671571|gb|AAF78286.1|AF073835_1|[8671571]
AAF78285
G protein-coupled receptor [human herpesvirus 5]
gi|8671569|gb|AAF78285.1|AF073834_1|[8671569]
AAF78284
G protein-coupled receptor [human herpesvirus 5]
gi|8671567|gb|AAF78284.1|AF073833_1|[8671567]
AAF78283
G protein-coupled receptor [human herpesvirus 5]
gi|8671565|gb|AAF78283.1|AF073832_1|[8671565]
AAF78282
G protein-coupled receptor [human herpesvirus 5]
gi|8671563|gb|AAF78282.1|AF073831_1|[8671563]
AAA98741
sequence differences confirmed in independent clones; variant of X17403 (AD169 strain), bases 219200 to 220263; G protein-coupled receptor gi|306304|gb|AAA98741.1|[306304]

Immunotoxins as Medicaments

Cytomegalovirus (CMV) is an important human pathogen, which emerges to cause disease in the immuno-compromised such as AIDS patients, neonates, and individuals who have been given immunosuppressive drugs as part of a transplantation regimen. In these individuals, the consequences of CMV in acute or re-emerging infections can be diare, including retinitis, encephalitis, and pneumocystis, among other pathologies. Furthermore, in immuno-competent hosts, CMV establishes a persistent lifelong infection through which it has been linked to a variety of inflammatory conditions including coronary artery occlusion following heart transplant and atherectomy and restenosis following angioplasty. CMV interacts with leukocytes during acute infection of the host as well as during lifelong latency. As such, leukocytes are important players in CMV-induced diseases and have been implicated in the acute phase of infection as vehicles for dissemination of virus and as sites of residence during lifelong latency.

Immunotoxins of the present invention are useful as medicaments, as they will target and kill CMV infected cells, i.e. they can be used to treat CMV infected individuals, such as e.g. AIDS patients, neonates, and individuals who have been given immunosuppressive drugs as part of a transplantation regimen and immuno-competent hosts.

In one embodiment the invention relates to use of an immunotoxin of the invention as a medicament. Hence, the immunotoxin of the invention relates to use for the manufacture of a medicament for the treatment or prevention of a CMV infection.

Immunotoxins of the invention may also be used for the establishment or progress of the CMV infection, or of any symptom of the CMV infection.

Immunotoxins of the invention may also be used for preventing the establishment or progress of the CMV infection, or of any symptom of the CMV infection in HIV infected patients, as it is well known that HIV infected patients are particular susceptible to CMV infection.

Further, CMV infections of the invention may be localised in a tissue selected from the group consisting of retina, heart, liver, lung, spleen or blood cells.

Preferred use of the immunotoxins further include treatments, wherein the individual for the treatment or prevention of the CMV infection is an immuno-compromised patient selected from the group consisting of HIV-patients, neonates and immunosuppressive patients, bona marrow transplant patients and solid organ transplants.

Further preferred use of the immunotoxins include treatments, wherein the individuals for the treatment or prevention of the CMV infection are patients suffering from coronary diseases.

Further preferred use of the immunotoxins includes treatments, wherein the individual for the treatment or prevention of the CMV infection is a fetus/neonate.

Pharmaceutical Composition of the Invention

The immunotoxins of the invention can be used for the treatment and diagnosis of diseases and disorders and/or pathological conditions, including preventive treatment, in an animal, in particular a mammal, but they are most preferably used for these purposes in humans. Moreover, the immunotoxins of the invention can be used also in healthy individuals and in healthy animals to change their physiological state.

In such treatment or diagnosis the immunotoxins of the invention is administered in form of a pharmaceutical composition further comprising a pharmaceutical acceptable carrier and, optionally, tabletting agents, wetting agents, binders and fillers, preservatives, such as antioxidants and anti-microbial agents, buffers and salts. Preferred carriers comprise injection media, particularly water. The compositions are administered by any conventional route including the oral, enteral, rectal and parenteral routes. Parenteral routes comprise intravenous, intramuscular, subcutaneous and peritoneal injection. The immunotoxins of the invention may also be administered by inhalation, as nasal spray, and topically on the skin. They may also be administered epidurally, intrathecally and intracerebroventricularly.

In particular the pharmaceutical composition containing a pharmacologically effective amount of an immunotoxin of the invention is administered to an animal, in particular a human, for alteration of physiological state, diagnosis, prevention or therapeutic treatment of CMV related diseases. Examples of such conditions include acute or re-emerging CMV infections which can cause diare, retinitis, encephalitis, and pneumocystis, among other pathologies.

Thus, in one embodiment the invention relates to a pharmaceutical composition comprising an immunotoxin according to the invention and any physiological acceptable salt thereof. In another embodiment, the invention relates to a pharmaceutical composition further comprising a pharmaceutical acceptable carrier.

The choice of pharmaceutically acceptable excipients in a composition for use according to the invention and the optimum concentration thereof cannot generally be predicted and must be determined on the basis of an experimental determination thereof. Also whether a pharmaceutically acceptable excipient is suitable for use in a pharmaceutical composition is generally dependent on which kind of dosage form is chosen. However, a person skilled in the art of pharmaceutical formulation can find guidance in e.g., "Remington: The science and practice of pharmacy" $20^{th}$ ed. Mack Publishing, Easton Pa., 2000 ISBN 0-912734-04-3.

A pharmaceutically acceptable excipient is a substance, which is substantially harmless to the individual to which the composition will be administered. Such an excipient normally fulfils the requirements given by the national drug agencies. Official pharmacopeias such as the British Pharmacopeia, the United States of America Pharmacopeia and the European Pharmacopeia set standards for well-known pharmaceutically acceptable excipients.

The pharmaceutical composition of the invention may be a parental, intravenous, oral, topical, trans-mucosal or transdermal composition.

In the following is given a review on relevant pharmaceutical compositions for use according to the invention. The review is based on the particular route of administration. However, it is appreciated that in those cases where a pharmaceutically acceptable excipient may be employed in different dosage forms or compositions, the application of a particular pharmaceutically acceptable excipient is not limited to a particular dosage form or of a particular function of the excipient.

Parenteral Compositions:

For systemic application, the compositions according to the invention may contain conventionally non-toxic pharmaceutically acceptable carriers and excipients according to the including microspheres and liposomes.

The compositions for use according to the invention include all kinds of solid, semisolid and fluid compositions. Compositions of particular relevance are e.g. solutions, suspensions, emulsions, gels, implantation tablets and implants.

The pharmaceutically acceptable excipients may include solvents, buffering agents, preservatives, humectants, chelating agents, antioxidants, stabilizers, emulsifying agents, suspending agents, gel-forming agents, diluents, disintegratig agents, binding agents, lubricants and wetting agents. For examples of the different agents see below.

Topical, trans-mucosal and trans-dermal compositions:

For application to the mucosa or the skin, the compositions for use according to the invention may contain conventionally non-toxic pharmaceutically acceptable carriers and excipients including microspheres and liposomes.

The compositions for use according to the invention include all kinds of solid, semi-solid and fluid compositions. Compositions of particular relevance are e.g. pastes, ointments, hydrophilic ointments, creams, gels, hydrogels, solutions, emulsions, suspensions, lotions, liniments, resoriblets, suppositories, enema, pessaries, moulded pessaries, vaginal capsules, vaginal tablets, shampoos, jellies, soaps, sticks, sprays, powders, films, foams, pads, sponges (e.g. collagen sponges), pads, dressings (such as, e.g., absorbent wound dressings), drenches, bandages, plasters and transdermal delivery systems.

The pharmaceutically acceptable excipients may include solvents, buffering agents, preservatives, humectants, chelating agents, antioxidants, stabilizers, emulsifying agents, suspending agents, gel-forming agents, ointment bases, suppository bases, penetration enhancers, perfumes, skin protective agents, diluents, disintegratig agents, binding agents, lubricants and wetting agents. For examples of the different agents see below.

Oral Compositions:

For application to the mucosa or the skin, the compositions for use according to the invention may contain conventionally non-toxic pharmaceutically acceptable carriers and excipients including microspheres and liposomes.

The composition for use according to the invention include all kinds of solid, semi-solid and fluid compositions. Compositions of particular relevance are e.g. solutions, suspensions, emulsions, uncoated tablets, modified-release tablets, gastro-resistant tablets, orodispersible tablets, effervescent tablets, chewable tablets, soft capsules, hard capsules, modified release capsules, gastro-resistant capsules, uncoated granules, effervescent granules, granules for the preparation of liquids for oral use, coated granules, gastro-resistant granules, modified-release granules, powders for oral administration and powders for the preparation of liquids for oral use.

The pharmaceutically acceptable excipients may include solvents, buffering agents, preservatives, humectants, chelating agents, antioxidants, stabilizers, emulsifying agents, suspending agents, gel-forming agents, diluents, disintegratig agents, binding agents, lubricants, coating agents and wetting agents. For examples of the different agents see below.

Examples of Various Agents:

Examples of solvents are but not limited to water, alcohols, vegetable or marine oils (e.g. edible oils like almond oil, castor oil, cacao butter, coconut oil, corn oil, cottonseed oil, linseed oil, olive oil, palm oil, peanut oil, poppyseed oil, rapeseed oil, sesame oil, soybean oil, sunflower oil, and teaseed oil), mineral oils, fatty oils, liquid paraffin, polyethylene glycols, propylene glycols, glycerol, liquid polyalkylsiloxanes, and mixtures thereof.

Examples of buffering agents are but not limited to citric acid, acetic acid, tartaric acid, lactic acid, hydrogenphosphoric acid, diethylamine etc.

Examples of preservatives for use in compositions are but not limited to parabens, such as methyl, ethyl, propyl p-hydroxybenzoate, butylparaben, isobutylparaben, isopropylparaben, potassium sorbate, sorbic acid, benzoic acid, methyl benzoate, phenoxyethanol, bronopol, bronidox, MDM hydantoin, iodopropynyl butylcarbamate, EDTA, benzalconium chloride, and benzylalcohol, or mixtures of preservatives.

Examples of humectants are but not limited to glycerin, propylene glycol, sorbitol, lactic acid, urea, and mixtures thereof.

Examples of chelating agents are but not limited to sodium EDTA and citric acid.

Examples of antioxidants are but not limited to butylated hydroxy anisole (BHA), ascorbic acid and derivatives thereof, tocopherol and derivatives thereof, cysteine, and mixtures thereof.

Examples of emulsifying agents are but not limited to naturally occurring gums, e.g. gum acacia or gum tragacanth; naturally occurring phosphatides, e.g. soybean lecithin; sorbitan monooleate derivatives; wool fats; wool alcohols; sorbitan esters; monoglycerides; fatty alcohols; fatty acid esters (e.g. triglycerides of fatty acids); and mixtures thereof.

Examples of suspending agents are but not limited to celluloses and cellulose derivatives such as, e.g., carboxymethyl cellulose, hydroxyethylcellulose, hydroxypropylcellulose, hydroxypropylmethylcellulose, carraghenan, acacia gum, arabic gum, tragacanth, and mixtures thereof.

Examples of gel bases and viscosity-increasing are but not limited to liquid paraffin, polyethylene, fatty oils, colloidal silica or aluminium, zinc soaps, glycerol, propylene glycol, tragacanth, carboxyvinyl polymers, magnesium-aluminium silicates, Carbopol®, hydrophilic polymers such as, e.g. starch or cellulose derivatives such as, e.g., carboxymethylcellulose, hydroxyethylcellulose and other cellulose derivatives, water-swellable hydrocolloids, carragenans, hyaluronates (e.g. hyaluronate gel optionally containing sodium chloride), and alginates including propylene glycol aginate.

Examples of ointment bases are but not limited to beeswax, paraffin, cetanol, cetyl palmitate, vegetable oils, sorbitan esters of fatty acids (Span), polyethylene glycols, and condensation products between sorbitan esters of fatty acids and ethylene oxide, e.g. polyoxyethylene sorbitan monooleate (Tween).

Examples of hydrophobic ointment bases are but not limited to paraffins, vegetable oils, animal fats, synthetic glycerides, waxes, lanolin, and liquid polyalkylsiloxanes.

Examples of hydrophilic ointment bases are but not limited to solid macrogols (polyethylene glycols).

Examples of powder components are but not limited to alginate, collagen, lactose, powder which is able to form a gel when applied to a wound (absorbs liquid/wound exudate).

Examples of diluents and disintegrating agents are but not limited to lactose, saccharose, emdex, calcium phosphates, calcium carbonate, calcium sulphate, mannitol, starches and microcrystalline cellulose.

Examples of binding agents are but not limited to saccharose, sorbitol, gum acacia, sodium alginate, gelatine, starches, cellulose, sodium coboxymethylcellulose, methylcellulose, hydroxypropylcellulose, polyvinylpyrrolidone and polyetyleneglycol.

Examples of wetting agents are but not limited to sodium laurylsulphate and polysorbate 80.

Examples of lubricants are but not limited to talcum, magnesium stearate, calcium stearate, silicium oxide, precirol and polyethylenglycol.

Examples of coating agents are but not limited to hydroxypropylcellulose, hydroxypropylmethylcellulose, polyvinylpropylidone, ethylcellulose and polymethylacrylates.

Examples of suppository bases are but not limited to oleum cacao, adeps solidus and polyethylenglycols.

The pharmaceutical composition preferably comprises an effective dosage of an immunotoxin of the invention. The pharmaceutical composition may comprise a dosage of an immunotoxin from 10 μg to 30000 μg/day.

The immunotoxin of the invention is present in the medicament in an amount of 0.001-99%, typically 0.01-75%, more typically 0.1-20%, especially 1-10% by weight of the medicament.

A pharmaceutical composition of the invention may be administered as a single dosage, regular or continued administration.

At present, the most common drugs for the treatment of CMV infection in transplantation patients and HIV/AIDS patients are the generic drugs Ganciclovir and Acyclovir, originally developed for herpes simplex virus (HSV). Ganciclovir and Acyclovir have a suppressing effect on CMV as well as on HSV. Vistide from Gilead is a newer compound that is expected to grow and take over the market with Roche's Valcyte at the expense of the older generic drugs.

A pharmaceutical composition of the invention may be administered simultaneous, separate or sequential with one or more anti-viral therapeutics, such as e.g. Ganciclovir and Acyclovir, Vistide, Valcyte.

A pharmaceutical composition of the invention may be co-administered with anti-HIV therapeutics, such as e.g. protease inhibitors, fusion inhibitors, reverse transcriptase inhibitors and/or nucleoside analogs or HAART.

None of the existing drugs, patented or generic, can eradicate the infection, merely halting the CMV disease progression in immuno-compromised or immuno-suppressed patients. In recent clinical studies, Foscavir and Ganciclovir were compared on their ability to treat immuno-compromised patients. The results showed a 30% better suppression of the infection using Foscavir. However 40% of the patients on Foscavir later switched to Ganciclovir because of intolerable nausea. These results show that there is room for improvement both in efficacy and in toxicity levels.

A pharmaceutical composition of the invention may be administered simultaneous, separate or sequential with one or more immunosuppressive therapeutics, such as e.g. cyclosporin A, azathioprine, cyclophosphamide, corticosteroids (e.g. prednisone) methotrexate mycophenolate mofetil, tacrolimus, sirolimus and Basiliximab (Simulect), a chimeric (human/murine) monoclonal antibody Interleukin 2 receptor antagonists and anti-pan-T cell polyclonal and monoclonal antibody Further included in the invention is a kit for treatment or prevention of CMV infection comprising (a) an effective amount of an immunotoxin of the invention and (b) a therapeutic or a combination of therapeutics selected from the group of antiviral therapeutics, immuno-suppressive therapeutics for simultaneous, separate or sequential administration.

Nucleic Acids of the Invention

Furthermore, included in the invention is a nucleic acid sequence comprising a nucleic acid sequence encoding an immunotoxin of the invention. In a preferred embodiment, the nucleic acid sequence comprises a nucleic acid sequence encoding an immunotoxin selected from the group consisting of SEQ ID NO: 10 and SEQ ID NO:11.

Further included is an expression vector comprising a sequence encoding an immunotoxin of the invention.

In a preferred embodiment, the expression vector comprises a nucleic acid sequence encoding SEQ ID NO:10 or SEQ ID NO:11.

Also a host transfected with the aforementioned expression vector is part of the invention.

Methods of Producing Immunotoxins of the Invention

The immunotoxins described herein may be produced by any suitable method known in the art. Such methods include constructing a nucleic acid sequence encoding the immunotoxin and expressing the sequence in a suitable transformed or transfected host.

A nucleic acid sequence encoding the immunotoxins described herein may be constructed by isolating or synthesizing a nucleic acid sequence encoding the desired immunotoxin or a part or variant thereof. The nucleic acid sequence may be prepared by chemical synthesis, e.g. by using an oligonucleotide synthesizer, wherein oligonucleotides are designed based on the amino acid sequence of the desired immunotoxin, and preferably selecting those codons that are favored in the host cell in which the immunotoxin will be produced. For example, several small oligonucleotides coding for portions of the desired immunotoxin may be synthesized and assembled by PCR, ligation or ligation chain reaction (LCR). The individual oligonucleotides typically contain 5' or 3' overhangs for complementary assembly.

Once assembled the nucleic acid sequence encoding the desired immunotoxin is inserted into a recombinant vector and operably linked to control sequences necessary for expression of the immunotoxin in the desired transformed host cell.

It should of course be understood that not all vectors and expression control sequences function equally well to express the nucleic acid sequence encoding the immunotoxins described herein. Neither will all hosts function equally well with the same expression system. However, one of skill in the art may make a selection among these vectors, expression control sequences and hosts without undue experimentation. For example, in selecting a vector, the host must be considered because the vector must replicate in it or be able to integrate into the chromosome. The vector's copy number, the ability to control that copy number, and the expression of any other proteins encoded by the vector, such as antibiotic markers, should also be considered. In selecting an expression control sequence, a variety of factors should also be considered. These include, for example, the relative strength of the sequence, its controllability, and its compatibility with the nucleic acid sequence encoding the immunotoxin, particularly as regards potential secondary structures. Hosts should be selected by consideration of their compatibility with the chosen vector, the host sensitivity and tolerability of the product coded for by the nucleic acid sequence, their secretion characteristics, their ability to fold the immunotoxin correctly, and their fermentation or culture requirements.

The recombinant vector may be an autonomously replicating vector, i.e. a vector, which exists as an extrachromosomal entity, the replication of which is independent of chromosomal replication, e.g. a plasmid. Alternatively, the vector is one which, when introduced into a host cell, is integrated into the host cell genome and replicated together with the chromosome(s) into which it has been integrated.

The vector is preferably an expression vector, in which the nucleic acid sequence encoding the desired immunotoxin is operably linked to additional segments required for transcription of the nucleic acid sequence. The vector is typically derived from plasmid or viral DNA. A number of suitable expression vectors for expression in the host cells mentioned herein are commercially available or described in the literature. Useful expression vectors for eukaryotic hosts, include, for example, vectors comprising expression control sequences from SV40, bovine papilloma virus, adenovirus and cytomegalovirus. Specific vectors are, e.g., pcDNA3.1 (+)\Hyg (Invitrogen, Carlsbad, Calif., USA) and pCI-neo (Stratagene, La Jola, Calif., USA). Useful expression vectors for bacterial hosts include known bacterial plasmids, such as plasmids from *E. coli*, including pBR322, pET3a and pET12a (both from Novagen Inc., WI, USA), wider host range plasmids, such as RP4, phage DNAs, e.g., the numerous derivatives of phage lambda, e.g., NM989, and other DNA phages, such as M13 and filamentous single stranded DNA phages. Useful expression vectors for yeast cells include the 2, plasmid and derivatives thereof, the POT1 vector (U.S. Pat. No. 4,931,373), the pJSO37 vector described in (Okkels, Ann. New York Acad. Sci. 782, 202-207, 1996) and pPICZ A, B or C (Invitrogen). Useful vectors for insect cells include pVL941, pBG311 (Cate et al., "Isolation of the Bovine and Human Genes for Mullerian Inhibiting Substance And Expression of the Human Gene In Animal Cells", Cell, 45, pp. 685-98 (1986), pBluebac 4.5 and pMelbac (both available from Invitrogen).

Other vectors for use in this invention include those that allow the nucleic acid sequence encoding the immunotoxins described herein to be amplified in copy number. Such amplifiable vectors are well known in the art. They include, for example, vectors able to be amplified by DHFR amplification (see, e.g., Kaufman, U.S. Pat. No. 4,470,461, Kaufman and Sharp, "Construction Of A Modular Dihydrafolate Reductase cDNA Gene: Analysis Of Signals Utilized For Efficient Expression", Mol. Cell. Biol., 2, pp. 1304-19 (1982)) and glutamine synthetase ("GS") amplification (see, e.g., U.S. Pat. No. 5,122,464 and EP 338 841).

The recombinant vector may further comprise a DNA sequence enabling the vector to replicate in the host cell in question. An example of such a sequence (when the host cell is a mammalian cell) is the SV40 origin of replication. When the host cell is a yeast cell, suitable sequences enabling the vector to replicate are the yeast plasmid 2μ replication genes REP 1-3 and origin of replication.

The vector may also contain a selectable marker, e.g. a gene the product of which complements a defect in the host cell, such as the gene coding for dihydrofolate reductase (DHFR) or the *Schizosaccharomyces pombe* TPI gene (described by P. R. Russell, Gene 40, 1985, pp. 125-130), or one which confers resistance to a drug, e.g. ampicillin, kanamycin, tetracyclin, chloramphenicol, neomycin, hygromycin or methotrexate. For filamentous fungi, selectable markers include amdS, pyrG, arcB, niaD, sC.

A wide variety of expression control sequences may be used in the present invention. Such useful expression control sequences include the expression control sequences associated with structural genes of the foregoing expression vectors as well as any sequence known to control the expression of genes of prokaryotic or eukaryotic cells or their viruses, and various combinations thereof.

Examples of suitable control sequences for directing transcription in mammalian cells include the early and late promoters of SV40 and adenovirus, e.g. the adenovirus 2 major late promoter, the MT-1 (metallothionein gene) promoter, the human cytomegalovirus immediate-early gene promoter (CMV), the human elongation factor 1α (EF-1α) promoter, the *Drosophila* minimal heat shock protein 70 promoter, the Rous Sarcoma Virus (RSV) promoter, the human ubiquitin C (UbC) promoter, the human growth hormone terminator, SV40 or adenovirus Elb region polyadenylation signals and the Kozak consensus sequence (Kozak, M. *J Mol Biol* 1987 Aug. 20; 196(4):947-50).

In order to improve expression in mammalian cells a synthetic intron may be inserted in the 5' untranslated region of the nucleotide sequence encoding the immunotoxin. An example of a synthetic intron is the synthetic intron from the plasmid pCI-Neo (available from Promega Corporation, Wis., USA).

Examples of suitable control sequences for directing transcription in insect cells include the polyhedrin promoter, the P10 promoter, the *Autographa californica* polyhedrosis virus basic protein promoter, the baculovirus immediate early gene 1 promoter and the baculovirus 39K delayed-early gene promoter, and the SV40 polyadenylation sequence.

Examples of suitable control sequences for use in yeast host cells include the promoters of the yeast α-mating system, the yeast triose phosphate isomerase (TPI) promoter, promoters from yeast glycolytic genes or alcohol dehydrogenase genes, the ADH2-4-c promoter and the inducible GAL promoter.

Examples of suitable control sequences for use in filamentous fungal host cells include the ADH3 promoter and terminator, a promoter derived from the genes encoding *Aspergillus oryzae* TAKA amylase triose phosphate isomerase or alkaline protease, an *A. niger* α-amylase, *A. niger* or *A. nidulans* glucoamylase, *A. nidulans* acetamidase, *Rhizomucor miehei* aspartic proteinase or lipase, the TPI1 terminator and the ADH3 terminator.

Examples of suitable control sequences for use in bacterial host cells include promoters of the lac system, the trp system, the TAC or TRC system and the major promoter regions of phage lambda.

Any suitable host may be used to express the immunotoxins or parts thereof described herein, including bacteria, fungi (including yeasts), plant, insect, mammal, or other appropriate animal cells or cell lines, as well as transgenic animals or plants. In one embodiment, the host cell is a eukaryotic host cell, such as a mammalian host cell capable of glycosylation.

Examples of bacterial host cells include gram positive bacteria such as strains of *Bacillus*, e.g. *B. brevis* or *B. subtilis*, *Pseudomonas* or *Streptomyces*, or gram negative bacteria, such as strains of *E. coli*. The introduction of a vector into a bacterial host cell may, for instance, be effected by protoplast transformation (see, e.g., Chang and Cohen, 1979, *Molecular General Genetics* 168: 111-115), using competent cells (see, e.g., Young and Spizizen, 1961, *Journal of Bacteriology* 81: 823-829, or Dubnau and Davidoff-Abelson, 1971, *Journal of Molecular Biology* 56: 209-221), electroporation (see, e.g., Shigekawa and Dower, 1988, *Biotechniques* 6: 742-751), or conjugation (see, e.g., Koehler and Thorne, 1987, *Journal of Bacteriology* 169: 5771-5278).

Examples of suitable filamentous fungal host cells include strains of *Aspergillus*, e.g. *A. oryzae*, *A. niger*, or *A. nidulans*, *Fusarium* or *Trichoderma*. Fungal cells may be transformed by a process involving protoplast formation, transformation of the protoplasts, and regeneration of the cell wall in a manner known per se. Suitable procedures for transformation of *Aspergillus* host cells are described in EP 238 023 and U.S. Pat. No. 5,679,543. Suitable methods for transforming *Fusarium* species are described by Malardier et al., 1989, *Gene* 78: 147-156 and WO 96/00787. Yeast may be transformed using the procedures described by Becker and Guarente, In Abelson, J. N. and Simon, M. I., editors, *Guide to Yeast Genetics and Molecular Biology, Methods in Enzymology*, Volume 194, pp 182-187, Academic Press, Inc., New York; Ito et al., 1983, *Journal of Bacteriology* 153: 163; and Hinnen et al., 1978, *Proceedings of the National Academy of Sciences USA* 75: 1920.

Examples of suitable yeast host cells include strains of *Saccharomyces*, e.g. *S. cerevisiae*, *Schizosaccharomyces*, *Kluyveromyces*, *Pichia*, such as *P. pastoris* or *P. methanolica*, *Hansenula*, such as *H. Polymorpha* or *Yarrowia*. Methods for transforming yeast cells with heterologous DNA and producing heterologous polypeptides there from are disclosed by Clontech Laboratories, Inc, Palo Alto, Calif., USA (in the product protocol for the Yeastmaker™ Yeast Tranformation System Kit), and by Reeves et al., FEMS Microbiology Letters 99 (1992) 193-198, Manivasakam and Schiestl, Nucleic Acids Research, 1993, Vol. 21, No. 18, pp. 4414-4415 and Ganeva et al., FEMS Microbiology Letters 121 (1994) 159-164.

Examples of suitable insect host cells include a *Lepidoptora* cell line, such as *Spodoptera frugiperda* (Sf9 or Sf21) or *Trichoplusioa ni* cells (High Five) (U.S. Pat. No. 5,077,214). Transformation of insect cells and production of heterologous polypeptides therein may be performed as described by Invitrogen.

Examples of suitable mammalian host cells include Chinese hamster ovary (CHO) cell lines, (e.g. CHO-K1; ATCC CCL-61), Green Monkey cell lines (COS) (e.g. COS 1 (ATCC CRL-1650), COS 7 (ATCC CRL-1651)); mouse cells (e.g. NS/O), Baby Hamster Kidney (BHK) cell lines (e.g. ATCC CRL-1632 or ATCC CCL-10), and human cells (e.g. HEK 293 (ATCC CRL-1573)), as well as plant cells in tissue culture. Additional suitable cell lines are known in the art and available from public depositories such as the American Type Culture Collection, Rockville, Md. Also, the mammalian cell, such as a CHO cell, may be modified to express sialyltransferase, e.g. 1,6-sialyltransferase, e.g. as described in U.S. Pat. No. 5,047,335, in order to provide improved glycosylation of the receptor.

The present invention also includes a fusion protein comprising one or several copies of the sequence of an immunotoxin of the invention. Such a fusion protein is typically manufactured by use of an expression system by utilizing the proper DNA, according to the principles described above, and by application of procedures well known in the art.

The invention also includes a vector comprising a DNA which encodes a fusion protein comprising the amino acid sequence of one or several copies of the immunotoxin of the invention. According to the present invention DNA can be exchanged for a chemically altered non-natural DNA, said non-natural DNA being capable of essentially affording the same function as natural DNA with respect to peptide or protein synthesis. Moreover, the DNA according to the invention can also be exchanged for RNA. It is particularly advantageous to use RNA or a non-natural RNA when the non-natural DNA or RNA is administered to an animal, in particular a human, the reason being avoidance of RNA or non-natural DNA recombining with endogenous DNA of the animal or human, thus diminishing the risk of long term side effects.

In is also contemplated that the immunotoxin is not prepared as a translational fusion. Instead the ligand and toxin parts may be synthesized separately and subsequently fused by chemical means or protein ligation.

Further, is contemplated that the ligand and/or toxin may be a polypeptide produced in vitro by e.g. chemical synthesis Further, is contemplated that the ligand and/or toxin may not be a polypeptide and instead e.g. a synthetic molecule.

CMV as Marker for Progression to AIDS/Death

Before highly active antiretroviral therapy (HAART) became available, cytomegalovirus was a major cause of opportunistic infection in HIV-infected patients and was associated with accelerated progression to AIDS and death. A study has investigated whether cytomegalovirus viraemia remains a significant risk factor for progression of HIV disease and death in the era of HAART.

Methods 374 patients whose CD4-cell count had ever been below 100 per μL were enrolled in a prospective study. Serial blood samples were tested for cytomegalovirus by PCR. Rates of new cytomegalovirus disease, new AIDS-defining disorders, and death were calculated over a median follow-up of 37 months after stratification according to baseline and most recent cytomegalovirus PCR status at any point during follow-up.

Findings Of 2969 PCR assays, 375 (12.6%) were positive for cytomegalovirus DNA. 259 (69.3%) patients were persistently negative for cytomegalovirus by PCR; 15 were persistently positive; and 100 were intermittently positive and negative. In multivariate models, cytomegalovirus PCR-positive status as a time-updated covariate was significantly associated with increased relative rates of progression to a new AIDS defining disorder (2.22 [95% CI 1.27–3.88] p=0.005) and death (4.14 [1.97–8.70] p=0.0002).

Interpretation Detection of cytomegalovirus in blood by PCR continues to identify patients with a poor prognosis, even in the era of HAART. Randomised controlled clinical trials of drugs active against cytomegalovirus are needed to investigate whether this virus is a marker or a determinant of HIV disease progression.

Method of Treatment or Prophylaxis

The present invention also relates to a method of treatment or prophylaxis of a CMV infection comprising administering an effective amount of an immunotoxin of the invention to an individual in the need thereof. The individual is any person having a CMV infection or any person in the risk of getting a CMV infection. In one embodiment, the individual is an immuno-compromised patient selected from the group consisting of HIV-patients, neonates and immunosuppressive patients, bona marrow transplant patients and solid organ transplant patients. In another embodiment, the individual is a patient suffering from coronary diseases.

In yet another embodiment, the invention relates to method of treatment or prophylaxis of a CMV infection comprising administering an effective amount of an immunotoxin of the invention to an individual in the need thereof, wherein CMV infection is localised in a tissue selected from the group consisting of retina, heart, liver, lung, spleen and blood cells of the individual.

In a further embodiment, the invention relates to a method for preventing the establishment or progress of the CMV infection, or of any symptom of the CMV infection.

With respect to the above description of the various aspects of the present invention and of the specific embodiments of these aspects it should be understood that any feature and characteristic described or mentioned above in connection with one aspect and/or one embodiment of an aspect of the invention also apply by analogy to any or all other aspects and/or embodiments of the invention described.

EXAMPLES

Example 1

Construction of the Recombinant Immunotoxin, CX3CL1-PE38 KDEL in *E. coli*

Fractalkine cDNA was amplified from the CX3CL1 expression plasmid pLSM103 (kindly provided by Tracy Handel) and the exotoxin PE38 KDEL from pRB1399 (kindly provided by Ira Pastan). An NcoI site, a his6 tag and a factor Xa cleavage site was added to the N-terminal part of CX3CL1 and an overlap with the PE38 sequence was added to the C-terminal by standard PCR techniques. CX3CL1 was amplified with the primers CX3CL1 (6his,Xa) S (tag cca tgg atg cac cac cac cac cac cac atc gaa ggt cgt cag cac cac ggt gtg acg) and CX3CL1(PE38) AS (ctg ccg ccc tcg cca ttt cga gtt agg gca g).

The PCR reaction mix was:
0.4 µM of each primer
5 µl 10×pfu (stratagen) buffer
0.2 µM dNTP
5 µl DMSO
0.5 µl pfu
100 ng pLSM103
H2O to 50 µl
The PCR conditions was:
3 min 95 C
35 cycles of
30 sec 95 C
40 sec 60
1 min 72 C
10 min 72 C
Expected fragment length was 291 bp.

An overlap with CX3CL1 was added to the N-terminal of PE38 and the fragment was amplified with the primers PE38 (CX3CL1) S (cta act cga aat ggc gag ggc ggc agc ctg gc) and PE38 KDEL AS (tag gaa ttc tta gag ctc gtc ttt cgg cg).

The PCR reaction mix and the PCR conditions was as described above.

The fragments were purified from a 1% agarose gel using the promega wizard kit and ligated in a PCR reaction whit the CX3CL1 (6his,Xa) S and PE38 KDEL AS primers creating the CX3CL1-PE38 fusion protein immunotoxin (IMT) cDNA.

Concentrations and conditions were as above but with 1.25 µl PE38 fragment and 0.25 µl CX3CL1 fragment as template DNA.

The IMT fragment was purified from agarose gel as above and eluted in 40 µl water. (Fragment length 1306 bp)

The IMT and the bacterial expression vector pET24d (Novagen) were prepared for cohesive end ligation by NcoI and EcoRI restriction enzyme digestion.

40 µl of IMT or 2 µg pET24d vector+10 µl EcoRI buffer, 1 µl NcoI, 1 µl EcoRI, and water to 100 µl were mixed and incubated at 37 C for 90 min.

Both fragment were purified sequentially in 1 vol. phenol and 1 vol. chloroform and precipitated 2.5 vol. 96% ethanol/0.1 vol. 3 M NaAc pH 4.6. The fragments were re-suspended in 30 µl water for pET24d and 10 µl for IMT and used for cohesive end ligation.

Cohesive end Ligation of pET24d and IMT
1 µl NcoI/EcoRI digested pET24d and 5 µl NcoI/EcoRI digested IMT were mixed with water to 10 µl, 10 µl 2× quick ligase buffer and 1 µl quick T4 DNA ligase and incubated for 5 min at RT.

Cloning of the IMT Construct
30 µl competent F' cells (Invitrogen) were thawed on ice and 2 µl IMT was added and incubated for 15 min on ice.
The bacteria were heat shocked at 42 C in a water bath for 60 seconds followed by incubation on ice for 2 min.
450 µl SOC media was added and incubated at 37 C for 1 h.
125 µl bacteria suspension was plated on LB agar plates containing and 30 µg/ml kanamycin and incubated O/N at 37 C.

Bacteria colonies was picked and incubated in 5 ml LB+kananycin media ON 37 C To verify the presence of IMT in the F' cells plasmid DNA were purified using Qiagens plasmid mini prep purification kit and cut with EcoRI and NcoI.

The restriction digest mix was:
5 µl plasmid
2 µl EcoRI buffer
0.25 µl EcoRI
0.25 µl NcoI
12.5 µl water The reaction was left for 90 min at 37 C and 10 µl was analysed on an agarose gel and the presence of a fragment with the expected size (1306 bp) were detected.

2 ml F'IMT overnight culture was used to inoculate 100 ml LB media to make a plasmid DNA maxi-preparation. Plasmid was purified from 100 ml overnight culture using Qiagen's plasmid 'maxi prep' purification kit and the precipitated DNA was dissolved in 250 µl water. To verify the presence of IMT the plasmid is digested with both EcoRI and NcoI to give a fragment of 1306 bp and with XhoI to give a fragment 300 bp. Plasmid DNA concentration was determined to 0.22 µg/µl.

The restriction digest mix was: 11.5 µl Plasmid
1.5 µl EcoRI
1.5 µl NcoI
10 µl EcoRI buffer
75.5 µl water
or
11.5 µl plasmid
1 µl BSA
1.5 µl XhoI
10 µl NEB2
77 µl water Both reactions were incubated for 90 min at 37 C and analysed on an agarose gel. To confirm the IMT sequence the plasmid was sequenced using the vector specific primers T7 promoter primer and T7 terminator primer, which confirmed the correct sequence of IMT.

Transformation of the IMT construct into Origami 2 cells (Novagen)
50 µl chemically competent origami 2 cells were thawed on ice.
75 ng IMT construct was added and the reaction and incubated on ice for 5 min.
The mix was heated in a water bath for 30 sec at 42 C and cooled on ice for 15 min.
150 µl SOC was added and incubate for 1 h at 37 C.
75 µl IMT transformed origami 2 cells were added to agar plates containing tetracycline and kanamycin and incubated ON at 37 C.
One colony was cloned and expand Expression of the Recombinant Immunotoxin, CX3CL1-PE38 KDEL in $E.$ $coli$.
IMT expression in Origami 2 cells (Novagen)
30 ml LB media+30 µg/ml of kanamycin and 12.5 µg/ml of tetracycline were inoculated with IMT transformed origami 2 cells and incubated O/N at 37 C.
1.5 L (3×500 ml) LB media was inoculated with the O/N culture and incubated at 37 C until $OD_{600}$=0.6.
IMT expression was induced with 0.5 mM isopropyl b-D-1-thiogalactopyranoside (IPTG) for 2.5 h and cells were harvest by centrifugation (10000 g 15 min 4 C in a preweighed tube.

Lysis of $E.$ $Coli$, using the BugBuster Master Mix.
The pellet was resuspended in 5 ml BugBuster (Novagen) pr. gram wet pellet and incubated for 10-20 min or until extract were no longer viscous.
Insoluble cell debris was removed by centrifugation at 16000 g for 20 min at 4 C.
The supernatant, containing the soluble IMT protein, was transferred to a clean tube.

Purification of His tagged IMT in Ni-affinity column.
Imidazole was added to 20 mM final concentration, pH adjusted to 7.5 and the sample was filtered through a 0.22 µm filter.
The column was washed with wash buffer and the sample was added.

The column with the bound protein was washed with 5× column volumes wash buffer.

His-tagged IMT was eluted in elution buffer containing 250 mM imidazole.

Buffer exchange and concentration using the icon concentrator with a cut off at 20 KDa from pierce.

The IMT protein was loaded onto the icon tube and centrifuged at 3500×g until desired concentration/volume is obtained.

Factor Xa cleavage buffer was added to the original volume and centrifuged until the desired concentration is obtained. This step is repeated 3 times.

IMT protesase digest using Factor Xa

Factor Xa is added to the protein solution in a ratio of 1 unit factor Xa to 10 µg protein and incubated for 5 h at RT.

Factor Xa is removed using factor Xa capture kit (Novagen)

After factor Xa removal IMT is stored at −20 C.

Buffers.

Wash buffer: PBS+20 mM imidazole, pH 7.5

Elution buffer: PBS+100 mM, 250 mM or 500 mM Imidazole, pH 7.5

Factor Xa cleavage buffer: 5 mM CaCl, 100 mM NaCl, 50 mMtris-Cl, pH 8.0.

In Vitro Pharmacology and Cell Biology

Example 2

Analysis of the CX3CL1-PE38 KDEL

US28 Binding Affinity

COS-7 cells are transferred to 24 well culture plates 1 day after transfection. The number of cells seeded per well is such as to obtain 5-10% specific binding of the added radioactive ligand. Two days after transfection competition binding is performed on whole cells for 3 h at 4° C. using 12 µM of either $^{125}$I-MIP-1α, $^{125}$I-MIP-1β, $^{125}$I-RANTES, $^{125}$I-MCP-1, $^{125}$I-CX$_3$C or another high affinity US28 ligand plus variable amounts of unlabeled ligand to be tested in 0.5 ml of a 50 mM HEPES buffer, pH 7.4 supplemented with 1 mM CaCl$_2$, 5 mM MgCl$_2$ and 0.5% (w/v) bovine serum albumin. After incubation the cells are quickly washed four times in 4° C. binding buffer supplemented with 0.5 M NaCl to reduce unspecific binding and interference caused by ligand dimerization. Non-specific binding is determined as the binding in the presence of 0.1 µM unlabeled chemokine.

IC$_{50}$ values are determined by non-linear regression and K$_D$ and B$_{max}$ values are calculated from competition binding experiments using the equations K$_D$=IC$_{50}$−L and B$_{max}$=B$_0$ (1+(K$_D$/L)) using the Inplot 4.0 software (GraphPad Software, San Diego, Calif.).

Example 3

Analysis of the US28 Mediated CX3CL1-PE38 KDEL Internalization

Ligand/Immunotoxin-Feeding and Experiments

For ligand/immunotoxin-feeding experiments US28-expressing cells are grown on coverslips for 48 h. The cells are washed in binding medium (BM: RPMI-1640 without bicarbonate, containing 0.2% bovine serum albumin, 10 mM HEPES, and adjusted to pH 7.4) at room temperature. Subsequently, the cells are incubated in BM containing the ligand, either a modified chemokines ao the entire immunotoxin. After 1 h the coverslips is placed on ice and washed with cold BM. To remove cell surface-bound ligand, the cells are washed twice in BM adjusted to pH 3.0, followed by two 3-min incubations in the same medium, and returned to BM, pH 7.4. The cells are then fixed in PBS containing 3% paraformaldehyde for 10 min, stained with attained with an antibody against the ligand, with or without permeabilization with 0.05% saponin, and examined by confocal microscopy.

Endocytosis Assays

Endocytosis assays on adherent cells is performed essentially as described (Pelchen-Matthews et al., 1991↓). Briefly, cells are seeded in 16-mm wells in 24-well plates and grown for 2 d to a final density of ~2.5×10$^5$ cells per well. The cells are cooled on ice, washed with DMEM containing 4% FCS, and incubated for 2 h at 4° C. with 250 µl of either $^{125}$I-ligand or $^{125}$I-immunotoxin in DMEM. Subsequently, the cells are washed in DMEM to remove free ligand and then warmed by addition of 1 ml DMEM at 37° C. At selected times the cells are returned to 4° C. and washed with cold DMEM. For half of the wells, the cells are collected directly in 400 µl of 0.2 M NaOH and transferred to tubes for γ counting (total cell-associated activity). To determine the intracellular activity, the remaining wells are acid washed to remove cell surface ligand (acid-resistant activity). The cells are harvested in NaOH as above. The proportion of internalized activity for each time point is determined by dividing the acid-resistant activity by the total cell-associated activity Example 4

Depletion of US28 Positive Cells Measured by FACS-Analysis

Depletion of Cells with the Immunotoxin

US28 positive cells and control cells expressing an endogenous chemokines receptor not binding the immunotoxin are incubated were incubated with different concentrations of purified immunotoxin or medium as control for 24 h. Surviving cells are analyzed on a FACS and counted.

Cells expressing US28 or CXCR4 are grown to subconfluence on 24-well culture plates and incubated with different concentrations of purified immunotoxin or medium as control. After 40 h, the adherent and nonadherent cells were recovered and analyzed by FACS to measure the percentage of dead cells. We have previously established that dead (propidium iodide-positive) CHO cells can be identified by their light scatter properties.

In Vitro Virology

Example 6

CX3CL1-PE38 KDEL mediates inhibition of human CMV replication in human fibroblasts. Effect on wild type HCMV (strain AD169) and no effect on US28 knockout HCMV (strain AD169) as control.

Example 7

CX3CL1-PE38 KDEL mediated inhibition of mouse CMV replication in mouse fibroblasts. Effect on recombinant MCMV (strain smith) over-expressing US28 and no effect wild type MCMV (strain smith) as control.

In Vivo Virology

Example 8

Immunocompetent model: The effect of CX3CL1-PE38 KDEL on viral replication and dissemination in CX3CR1 knock out mice in both Balb/C and in C57/B6 background. Balb/C and B6 mice reveal a distinct viral susceptibility and disease progression. The effect of the CX3CL1-PE38 KDEL treatment is compared with either ganciclovir (GCV) or cidofovir (HPMPC). All drugs are administered intra peritoneal. Weight loss and viral titers in the peripheral lymph nodes, spleen and liver at days 3, 5 and 7 post infection and in the salivary gland at day 14 post infection are measured and scored to assess the effect of the treatments. Furthermore, viral replication and dissemination are studied by immunohistochemistry against MCMV IE1 of infected organs.

Example 9

Immunodeficient model: The effect of CX3CL1-PE38 KDEL on viral replication and disease progression in SCID (severe combined immuno deficiency) mice are studied. SCID mice succumb to CMV infection in a dose dependent manner, and is therefore the most sensitive model for measuring anti-CMV drug efficiency.

Example 11

Methods to Test the Affinity Moiety

Competitive binding experiments measure equilibrium binding of a single concentration of radioligand at various concentrations of an unlabeled competitor. Analyze these data to learn the affinity of the receptor for the competitor. An assay based on the competition between a labelled and an unlabelled ligand in the reaction with a receptor binding agent.

The receptor is made available for the ligand by expression in mammalian cells. The expression can be either stable or transient. Transient expression can be made by transfection of a relevant cell line with an expression construct encoding the receptor.

One day after transfection, the cells are transferred to relevant cell culture plates (e.g. 24 well plates, but dependent on the needed cell number). The number of cells seeded per well is determined to obtain 5-10% specific binding of the added radioactive ligand. Two days after transfection competition binding is performed on whole cells for 3 h at 4° C. using approximately 12 μM of radiolabeled ligand (e.g. $^{125}$I-MIP-1α, $^{125}$I-MIP-1β, $^{125}$I-RANTES, $^{125}$I-MCP-1 or $^{125}$I-$CX_3C$) plus variable amounts of unlabeled competitor ligand in binding buffer (0.5 ml of a 50 mM HEPES buffer, pH 7.4 supplemented with 1 mM $CaCl_2$, 5 mM $MgCl_2$ and 0.5% (w/v) bovine serum albumin). After incubation the cells are quickly washed four times in 4° C. binding buffer supplemented with 0.5 M NaCl to reduce unspecific binding and interference caused by ligand dimerization. Non-specific binding is determined as the binding in the presence of 0.1 μM unlabeled ligand (chemokine).

Saturation Binding Experiments

Saturation binding experiments measure equilibrium binding of various concentrations of the radioligand. Analyze the relationship between binding and ligand concentration to determine the number of sites, Bmax, and the ligand affinity, Kd Saturation radioligand binding experiments measure specific radioligand binding at equilibrium at various concentrations of the radioligand. Analyze these data to determine receptor number and affinity. Because this kind of experiment used to be analyzed with Scatchard plots (more accurately attributed to Rosenthal), they are sometimes called “Scatchard experiments”.

The analyses depend on the assumption that you have allowed the incubation to proceed to equilibrium. This can take anywhere from a few minutes to many hours, depending on the ligand, receptor, temperature, and other experimental conditions. The lowest concentration of radioligand will take the longest to equilibrate. When testing equilibration time, therefore, use a low concentration of radioligand (perhaps 10-20% of the KD).

REFERENCES

Barnett B B, Smee D F, Malek S M, Sidwell R W. Antimicrob Agents Chemother. 1996 February; 40(2):470-2.

Selective cytotoxicity of ricin A chain immunotoxins towards murine cytomegalovirus-infected cells.

Barnett B B, Smee D F, Malek S M, Sidwell R W. Antiviral Res. 1995 September; 28(1):93-100.

Selective cytotoxicity towards cytomegalovirus-infected cells by immunotoxins consisting of gelonin linked to anti-cytomegalovirus antibody.

Bruhl H, Cihak J, Stangassinger M, Schlondorff D, Mack M. J. Immunol. 2001 Feb. 15; 166(4):2420-6. Depletion of CCR5-expressing cells with bispecific antibodies and chemokine toxins: a new strategy in the treatment of chronic inflammatory diseases and HIV.

He D, Yang H, Lin Q, Huang, H, Int J Biochem Cell Biol. 2005 January; 37(1):192-205. Arg9-peptide facilitates the internalization of an anti-CEA immunotoxin and potentiates its specific cytotoxicity to target cells.

Kyte J, Doolittle, R F: J Mol. Biol. 1982 May 5; 157(1):105-32.

A simple method for displaying the hydropathic character of a protein.

U.S. Pat. No. 4,554,101 Nov. 19, 1985, Identification and preparation of epitopes on antigens and allergens on the basis of hydrophilicity Sequence List:

| | |
|---|---|
| SEQ ID NO: 1: | Protein sequence of immunotoxin comprising Rantes and PE38KDEL |
| SEQ ID NO: 2 | Protein sequence of $CX_3CL1$ (fractalkine) |
| SEQ ID NO: 3: | Protein sequence of US28 receptor |
| SEQ ID NO: 4 | Protein sequence of US27 receptor |
| SEQ ID NO: 5 | Protein sequence of UL33 receptor |
| SEQ ID NO: 6 | Protein sequence of UL78 receptor |
| SEQ ID NO: 7 | Protein sequence of vCCL2 chemokine |
| SEQ ID NO: 8 | Protein sequence of Exotoxin A |
| SEQ ID NO: 9 | Protein sequence of PE38KDEL |
| SEQ ID NO: 10 | Protein sequence of immunotoxin comprising of Fractalkine and PE38KDEL |
| SEQ ID NO: 11 | Protein sequence of immunotoxin comprising the chemokine part of fraktalkine pos. 25-100 of SEQ ID NO: 2 and PE38KDEL |
| SEQ ID NO: 12 | DNA sequence of immunotoxin comprising Rantes and PE38KDEL |
| SEQ ID NO: 13 | DNA sequence of $CX_3CL1$ (fractalkine) |
| SEQ ID NO: 14 | DNA sequence of US28 receptor |
| SEQ ID NO: 15 | DNA sequence of US27 receptor |
| SEQ ID NO: 16 | DNA sequence of UL33 receptor |
| SEQ ID NO: 17 | DNA sequence of UL78 receptor |
| SEQ ID NO: 18 | DNA sequence of vCCL2 chemokine |
| SEQ ID NO: 19 | DNA sequence of Exotoxin A |
| SEQ ID NO: 20 | DNA sequence of PE38KDEL |
| SEQ ID NO: 21 | DNA sequence of immunotoxin comprising of Fractalkine and PE38KDEL |
| SEQ ID NO: 22 | DNA sequence of immunotoxin comprising the chemokine part of fraktalkine pos. 25-100 of SEQ ID NO: 2 and PE38KDEL |

SEQ ID NO: 1
>RANTES-PE38KDEL fusion protein
SPYSSDTTPCCFAYIARPLPRAHIKEYFYTSGKCSNPAVVFVTRKNRQVCANPEKKWVREYINSLEMSEG

GSLAALTAHQACHLPLETFTRHRQPRGWEQLEQCGYPVQRLVALYLAARLSWNQVDQVIRNALASPGSGG

DLGEAIREQPEQARLALTLAAAESERFVRQGTGNDEAGAANADVVSLTCPVAAGECAGPADSGDALLERN

YPTGAEFLGDGGDVSFSTRGTQNWTVERLLQAHRQLEERGYVFVGYHGTFLEAAQSIVFGGVRARSQDLD

AIWRGFYIAGDPALAYGYAQDQEPDARGRIRNGALLRVYVPRSSLPGFYRTSLTLAAPEAAGEVERLIGH

PLPLRLDAITGPEEEGGRLETILGWPLAERTVVIPSAIPTDPRNVGGDLDPSSIPDKEQAISALPDYASQ

PGKPPKDEL

SEQ ID NO: 2

$CX_3CL1$
>gi|4506857|ref|NP_002987.1|chemokine (C—X3—C motif) ligand 1
[*Homo sapiens*]
MAPISLSWLLRLATFCHLTVLLAGQHHGVTKCNITCSKMTSKIPVALLIHYQQNQASCGKRAIILETRQH

RLFCADPKEQWVKDAMQHLDRQAAALTRNGGTFEKQIGEVKPRTTPAAGGMDESVVLEPEATGESSSLEP

TPSSQEAQRALGTSPELPTGVTGSSGTRLPPTPKAQDGGPVGTELFRVPPVSTAATWQSSAPHQPGPSLW

AEAKTSEAPSTQDPSTQASTASSPAPEENAPSEGQRVWGQGQSPRPENSLEREEMGPVPAHTDAFQDWGP

GSMAHVSVVPVSSEGTPSREPVASGSWTPKAEEPIHATMDPQRLGVLITPVPDAQAATRRQAVGLLAFLG

LLFCLGVAMFTYQSLQGCPRKMAGEMAEGLRYIPRSCGSNSYVLVPV

SEQ ID NO: 2a

>CX3CL1 chemokine part position 25-100 of SEQ ID NO: 2
QHHGVTKCNITCSKMTSKIPVALLIHYQQNQASCGKRAIILETRQHRLFCADPKEQWVKDAMQHLDRQAA

ALTRNG

SEQ ID NO: 3

US28 receptor
>gi|28373231|ref|NP_783808.1|US28 [Human herpesvirus 5 strain AD169]
MTPTTTTAELTTEFDYDEDATPCVFTDVLNQSKPVTLFLYGVVFLFGSIGNFLVIFTITWRRRIQCSGDV

YFINLAAADLLFVCTLPLWMQYLLDHNSLASVPCTLLTACFYVAMFASLCFITEIALDRYYAIVYMRYRP

VKQACLFSIFWWIFAVIIAIPHFMVVTKKDNQCMTDYDYLEVSYPIILNVELMLGAFVIPLSVISYCYYR

ISRIVAVSQSRHKGRIVRVLIAVVLVFIIFWLPYHLTLFVDTLKLLKWISSSCEFERSLKRALILTESLA

FCHCCLNPLLYVFVGTKFRQELHCLLAEFRQRLFSRDVSWYHSMSFSRRSSPSRRETSSDTLSDEVCRVS

QIIP

SEQ ID NO: 4

US27 receptor
>gi|9625863|ref|NP_040112.1|US27 [Human herpesvirus 5 strain AD169]
MTTSTNNQTLTQVSNMTNHTLNSTEIYQLFEYTRLGVWLMCIVGTFLNVLVITTILYYRRKKKSPSDTYI

CNLAVADLLIVVGLPFFLEYAKHHPKLSREVVCSGLNACFYICLFAGVCFLINLSMDRYCVIVWGVELNR

VRNNKRATCWVVIFWILAVLMGMPHYLMYSHTNNECVGEFANETSGWFPVFLNTKVNICGYLAPIALMAY

TYNRMVRFIINYVGKWHMQTLHVLLVVVVSFASFWFPFNLALFLESIRLLAGVYNDTLQNVIIFCLYVGQ

FLAYVRACLNPGIYILVGTQMRKDMWTTLRVFACCCVKQEIPYQDIDIELQKDIQRRAKHIKRTHYDRKN

APMESGEEEFLL

SEQ ID NO: 5

UL33 receptor
>gi|28373224|ref|NP_783781.1|GPCR; UL33 [Human herpesvirus 5 strain
AD169]
MDTIIHNSTRNNTPPHINDTCNMTGPLFAIRTTEAVLNTFIIFVGGPLNAIVLITQLLTNRVLGYSTPTI

YMTNLYSTNFLTLTVLPFIVLSNQWLLPAGVASCKFLSVIYYSSCTVGFATVALIAADRYRVLHKRTYAR

QSYRSTYMILLLTWLAGLIFSVPAAVYTTVVMHHDANDTNNTNGHATCVLYFVAEEVHTVLLSWKVLLTM

VWGAAPVIMMTWFYAFFYSTVQRTSQKQRSRTLTFVSVLLISFVALQTPYVSLMIFNSYATTAWPMQCEH

LTLRRTIGTLARVVPHLHCLINPILYALLGHDFLQRMRQCFRGQLLDRRAFLRSQQNQRATAETNLAAGN

NSQSVATSLDTNSKNYNQHAKRSVSFNFPSGTWKGGQKTASNDTSTKIPHRLSQSHHNLSGV

SEQ ID NO: 6
UL78 receptor
>gi|9625763|ref|NP_040012.1|UL78 [Human herpesvirus 5 strain AD169]
MSPSVEETTSVTESIMFAIVSFKHMGPFEGYSMSADRAASDLLIGMFGSVSLVNLLTIIGCLWVLRVTRP

PVSVMIFTWNLVLSQFFSILATMLSKGIMLRGALNLSLCRLVLFVDDVGLYSTALFFLFLILDRLSAISY

GRDLWHHETRENAGVALYAVAFAWVLSIVAAVPTAATGSLDYRWLGCQIPIQYAAVDLTIKMWFLLGAPM

IAVLANVVELAYSDRRDHVWSYVGRVCTFYVTCLMLFVPYYCFRVLRGVLQPASAAGTGFGIMDYVELAT

RTLLTMRLGILPLFIIAFFSREPTKDLDDSFDYLVERCQQSCHGHFVRRLVQALKRAMYSVELAVCYFST

SVRDVAEAVKKSSSRCYADATSAAVVVTTTTSEKATLVEHAEGMASEMCPGTTIDVSAESSSVLCTDGEN

TVASDATVTAL

SEQ ID NO: 7
vCCL2 chemokine
>gi|18845978|ref|NP_572064.1|ORF K4; macrophage inflammatory protein
vMIP-II
LGASWHRPDKCCLGYQKRPLPQVLLSSWYPTSQLCSKPGVIFLTKRGRQVCADKSKDWVKKLMQQLPVTAR SEQ ID NO: 8
Exotoxin A
>gi|151216|gb|AAB59097.1|exotoxin type A [Pseudomonas aeruginosa]
MHLIPHWIPLVASLGLLAGGSSASAAEEEAFDLWNECAKACVLDLKDGVRSSRMSVDPAIADTNGQGVLHY

SMVLEGGNDALKLAIDNALSITSDGLTIRLEGGVEPNKPVRYSYTRQARGSWSLNWLVPIGHEKPSNIKV

FIHELNAGNQLSHMSPIYTIEMGDELLAKLARDATFFVRAHESNEMQPTLAISHAGVSVVMAQTQPRREK

RWSEWASGKVLCLLDPLDGVYNYLAQQRCNLDDTWEGKIYRVLAGNPAKHDLDIKPTVISHRLHFPEGGS

LAALTAHQACHLPLETFTRHRQPRGWEQLEQCGYPVQRLVALYLAARLSWNQVDQVIRNALASPGSGGDL

GEAIREQPEQARLALTLAAAESERFVRQGTGNDEAGAANADVVSLTCPVAAGECAGPADSGDALLERNYP

TGAEFLGDGGDVSFSTRGTQNWTVERLLQAHRQLEERGYVFVGYHGTFLEAAQSIVFGGVRARSQDLDAI

WRGFYIAGDPALAYGYAQDQEPDARGRIRNGALLRVYVPRSSLPGFYRTSLTLAAPEAAGEVERLIGHPL

PLRLDAITGPEEEGGRLETILGWPLAERTVVIPSAIPTDPRNVGGDLDPSSIPDKEQAISALPDYASQPG

KPPREDLK

SEQ ID NO: 9
>PE38KDEL
EGGSLAALTAHQACHLPLETFTRHRQPRGWEQLEQCGYPVQRLVALYLAARLSWNQVDQVIRNALASPGS

GGDLGEAIREQPEQARLALTLAAAESERFVRQGTGNDEAGAANADVVSLTCPVAAGECAGPADSGDALLE

RNYPTGAEFLGDGGDVSFSTRGTQNWTVERLLQAHRQLEERGYVFVGYHGTFLEAAQSIVFGGVRARSQD

LDAIWRGFYIAGDPALAYGYAQDQEPDARGRIRNGALLRVYVPRSSLPGFYRTSLTLAAPEAAGEVERLI

GHPLPLRLDAITGPEEEGGRLETILGWPLAERTVVIPSAIPTDPRNVGGDLDPSSIPDKEQAISALPDYA

SQPGKPPKDEL

SEQ ID NO: 10
>CX3CL1 (full length, mature peptide)-PE38KDEL fusion protein
QHHGVTKCNITCSKMTSKIPVALLIHYQQNQASCGKRA

```
SLTCPVAAGECAGPADSGDALLERNYPTGAEFLGDGGDVSFSTRGTQNWTVERLLQAHRQLEERGYVFVG

YHGTFLEAAQSIVFGGVRARSQDLDAIWRGFYIAGDPALAYGYAQDQEPDARGRIRNGALLRVYVPRSSL

PGFYRTSLTLAAPEAAGEVERLIGHPLPLRLDAITGPEEEGGRLETILGWPLAERTVVIPSAIPTDPRNV

GGDLDPSSIPDKEQAISALPDYASQPGKPPKDEL
```

SEQ ID NO: 11
>CX3CL1(chemokines domain)-PE38KDEL fusion protein
```
QHHGVTKCNITCSKMTSKIPVALLIHYQQNQASCGKRAIILETRQHRLFCADPKEQWVKDAMQHLDRQAA

ALTRNGEGGSLAALTAHQACHLPLETFTRHRQPRGWEQLEQCGYPVQRLVALYLAARLSWNQVDQVIRNA

LASPGSGGDLGEAIREQPEQARLALTLAAAESERFVRQGTGNDEAGAANADVVSLTCPVAAGECAGPADS

GDALLERNYPTGAEFLGDGGDVSFSTRGTQNWTVERLLQAHRQLEERGYVFVGYHGTFLEAAQSIVFGGV

RARSQDLDAIWRGFYIAGDPALAYGYAQDQEPDARGRIRNGALLRVYVPRSSLPGFYRTSLTLAAPEAAG

EVERLIGHPLPLRLDAITGPEEEGGRLETILGWPLAERTVVIPSAIPTDPRNVGGDLDPSSIPDKEQAIS

ALPDYASQPGKPPKDEL
```

SEQ ID NO: 12
DNA sequence of aminoacid sequence SEQ ID NO: 1
>RANTES-PE38KDEL
```
TCCCCATATTCCTCGGACACCACACCCTGCTGCTTTGCCTACATTGCCCGCCCACTGCCCCGTGCCCACA

TCAAGGAGTATTTCTACACCAGTGGCAAGTGCTCCAACCCAGCAGTCGTCTTTGTCACCCGAAAGAACCG

CCAAGTGTGTGCCAACCCAGAGAAGAAATGGGTTCGGGAGTACATCAACTCTTTGGAGATGAGCGAGGGC

GGCAGCCTGGCCGCGCTGACCGCGCACCAGGCTTGCCACCTGCCGCTGGAGACTTTCACCCGTCATCGCC

AGCCGCGCGGCTGGGAACAACTGGAGCAGTGCGGCTATCCGGTGCAGCGGCTGGTCGCCCTCTACCTGGC

GGCGCGGCTGTCGTGGAACCAGGTCGACCAGGTGATCCGCAACGCCCTGGCCAGCCCCGGCAGCGGCGGC

GACCTGGGCGAAGCGATCCGCGAGCAGCCGGAGCAGGCCCGTCTGGCCCTGACCCTGGCCGCCGCCGAGA

GCGAGCGCTTCGTCCGGCAGGGCACCGGCAACGACGAGGCCGGCGCGGCCAACGCCGACGTGGTGAGCCT

GACCTGCCCGGTCGCCGCCGGTGAATGCGCGGGCCCGGCGGACAGCGGCGACGCCCTGCTGGAGCGCAAC

TATCCCACTGGCGCGGAGTTCCTCGGCGACGGCGGCGACGTCAGCTTCAGCACCCGCGGCACGCAGAACT

GGACGGTGGAGCGGCTGCTCCAGGCGCACCGCCAACTGGAGGAGCGCGGCTATGTGTTCGTCGGCTACCA

CGGCACCTTCCTCGAAGCGGCGCAAAGCATCGTCTTCGGCGGGGTGCGCGCGCGCAGCCAGGACCTCGAC

GCGATCTGGCGCGGTTTCTATATCGCCGGCGATCCGGCGCTGGCCTACGGCTACGCCCAGGACCAGGAAC

CCGACGCACGCGGCCGGATCCGCAACGGTGCCCTGCTGCGGGTCTATGTGCCGCGCTCGAGCCTGCCGGG

CTTCTACCGCACCAGCCTGACCCTGGCCGCGCCGGAGGCGGCGGGCGAGGTCGAACGGCTGATCGGCCAT

CCGCTGCCGCTGCGCCTGGACGCCATCACCGGCCCCGAGGAGGAAGGCGGGCGCCTGGAGACCATTCTCG

GCTGGCCGCTGGCCGAGCGCACCGTGGTGATTCCCTCGGCGATCCCCACCGACCCGCGCAACGTCGGCGG

CGACCTCGACCCGTCCAGCATCCCCGACAAGGAACAGGCGATCAGCGCCCTGCCGGACTACGCCAGCCAG

CCCGGCAAACCGCCGAAAGACGAGCTCTAA
```

SEQ ID NO: 13
DNA sequence of aminoacid sequence SEQ ID NO: 2
>CX3CL1(FL)-NM_002996
```
ATGGCTCCGATATCTCTGTCGTGGCTGCTCCGCTTGGCCACCTTCTGCCATCTGACTGTCCTGCTGGCTG

GACAGCACCACGGTGTGACGAAATGCAACATCACGTGCAGCAAGATGACATCAAAGATACCTGTAGCTTT

GCTCATCCACTATCAACAGAACCAGGCATCATGCGGCAAACGCGCAATCATCTTGGAGACGAGACAGCAC

AGGCTGTTCTGTGCCGACCCGAAGGAGCAATGGGTCAAGGACGCGATGCAGCATCTGGACCGCCAGGCTG

CTGCCCTAACTCGAAATGGCGGCACCTTCGAGAAGCAGATCGGCGAGGTGAAGCCCAGGACCACCCCTGC

CGCCGGGGGAATGGACGAGTCTGTGGTCCTGGAGCCCGAAGCCACAGGCGAAAGCAGTAGCCTGGAGCCG

ACTCCTTCTTCCCAGGAAGCACAGAGGGCCCTGGGGACCTCCCCAGAGCTGCCGACGGGCGTGACTGGTT
```

-continued

```
CCTCAGGGACCAGGCTCCCCCCGACGCCAAAGGCTCAGGATGGAGGGCCTGTGGGCACGGAGCTTTTCCG

AGTGCCTCCCGTCTCCACTGCCGCCACGTGGCAGAGTTCTGCTCCCCACCAACCTGGGCCCAGCCTCTGG

GCTGAGGCAAAGACCTCTGAGGCCCCGTCCACCCAGGACCCCTCCACCCAGGCCTCCACTGCGTCCTCCC

CAGCCCCAGAGGAGAATGCTCCGTCTGAAGGCCAGCGTGTGTGGGGTCAGGGACAGAGCCCCAGGCCAGA

GAACTCTCTGGAGCGGGAGGAGATGGGTCCCGTGCCAGCGCACACGGATGCCTTCCAGGACTGGGGCCT

GGCAGCATGGCCCACGTCTCTGTGGTCCCTGTCTCCTCAGAAGGGACCCCCAGCAGGGAGCCAGTGGCTT

CAGGCAGCTGGACCCCTAAGGCTGAGGAACCCATCCATGCCACCATGGACCCCCAGAGGCTGGGCGTCCT

TATCACTCCTGTCCCTGACGCCCAGGCTGCCACCCGGAGGCAGGCGGTGGGGCTGCTGGCCTTCCTTGGC

CTCCTCTTCTGCCTGGGGGTGGCCATGTTCACCTACCAGAGCCTCCAGGGCTGCCCTCGAAAGATGGCAG

GAGAGATGGCGGAGGGCCTTCGCTACATCCCCCGGAGCTGTGGTAGTAATTCATATGTCCTGGTGCCCGT

GTGA
```

SEQ ID NO: 14
DNA sequence of aminoacid sequence SEQ ID NO: 3
>gi|28373214: US28. 220132-221196 Human herpesvirus 5 (laboratory strain AD169)

```
ATGACACCGACGACGACGACCGCGGAACTCACGACGGAGTTTGACTACGATGAAGACGCGACTCCTTGTG

TTTTCACCGACGTGCTTAATCAGTCAAAGCCAGTTACGTTGTTTCTGTACGGCGTTGTCTTTCTCTTCGG

TTCCATCGGCAACTTCTTGGTGATCTTCACCATCACCTGGCGACGTCGGATTCAATGCTCCGGCGATGTT

TACTTTATCAACCTCGCGGCCGCCGATTTGCTTTTCGTTTGTACACTACCTCTGTGGATGCAATACCTCC

TAGATCACAACTCCCTAGCCAGCGTGCCGTGTACGTTACTCACTGCCTGTTTCTACGTGGCTATGTTTGC

CAGTTTGTGTTTTATCACGGAGATTGCACTCGATCGCTACTACGCTATTGTTTACATGAGATATCGGCCT

GTAAAACAGGCCTGCCTTTTCAGTATTTTTTGGTGGATCTTTGCCGTGATCATCGCCATTCCACACTTTA

TGGTGGTGACCAAAAAAGACAATCAATGTATGACCGACTACGACTACTTAGAGGTCAGTTACCCGATCAT

CCTCAACGTAGAACTCATGCTTGGTGCTTTCGTGATCCCGCTCAGTGTTATCAGCTACTGCTACTACCGC

ATTTCCAGAATCGTTGCGGTGTCTCAGTCGCGCCACAAAGGTCGCATTGTACGGGTACTTATAGCGGTCG

TGCTTGTCTTTATCATCTTTTGGCTGCCGTACCACCTAACGCTGTTTGTGGACACGTTAAAACTCCTCAA

ATGGATCTCCAGCAGCTGCGAGTTCGAAAGATCGCTCAAACGTGCGCTCATCTTGACCGAGTCGCTCGCC

TTTTGTCACTGTTGTCTCAATCCGCTGCTGTACGTCTTCGTGGGCACCAAGTTTCGGCAAGAACTACACT

GTCTGCTGGCCGAGTTTCGCCAGCGACTCTTTTCCCGCGATGTATCCTGGTACCACAGCATGAGCTTTTC

GCGTCGGAGCTCGCCGAGTCGAAGAGAGACATCTTCCGACACGCTGTCCGACGAGGTGTGTCGCGTCTCA

CAAATTATACCGTAA
```

SEQ ID NO: 15
DNA sequence of aminoacid sequence SEQ ID NO: 4
>gi|28373214: US27. 218836-219924 Human herpesvirus 5 (laboratory strain AD169)

```
ATGACCACCTCTACAAATAATCAAACCTTAACGCAGGTGAGCAACATGACAAACCACACCTTAAACAGCA

CCGAAATTTATCAGTTGTTCGAGTACACTCGGTTGGGGGTATGGTTGATGTGCATCGTGGGCACGTTTCT

GAACGTGCTGGTGATTACCACCATCCTGTACTACCGTCGTAAGAAAAAATCTCCGAGCGATACCTACATC

TGCAACCTGGCTGTAGCCGATCTGTTGATTGTCGTCGGCCTGCCGTTTTTTCTAGAATATGCCAAGCATC

ACCCTAAACTCAGCCGAGAGGTGGTTTGTTCGGGACTCAACGCTTGTTTCTACATCTGTCTTTTTGCCGG

CGTTTGTTTTCTCATCAACCTGTCGATGGATCGCTACGCGTCATCGTTTGGGGTGTAGAATTGAACCGC

GTGCGAAATAACAAGCGGGCCACCTGTTGGGTGGTGATTTTTTGGATACTAGCCGTGCTCATGGGGATGC

CACATTACCTGATGTACAGCCATACCAACAACGAGTGTGTTGGTGAATTCGCTAACGAGACGTCGGGTTG

GTTCCCCGTGTTTTTGAACACCAAAGTTAACATTTGCGGCTACCTGGCGCCCATCGCGCTGATGGCGTAC
```

-continued

ACGTACAACCGTATGGTGCGGTTTATCATTAACTACGTTGGTAAATGGCACATGCAGACGCTCCACGTTC

TTTTGGTTGTGGTTGTGTCTTTTGCCAGCTTTTGGTTTCCTTTCAACCTGGCGCTATTTTTAGAATCCAT

CCGTCTTCTGGCGGGAGTGTACAATGACACACTTCAAAACGTTATTATCTTCTGTCTATACGTCGGTCAG

TTTTTGGCCTACGTTCGCGCTTGTCTGAATCCTGGGATCTACATCCTAGTAGGCACTCAAATGAGGAAGG

ACATGTGGACAACCCTAAGGGTATTCGCCTGTTGCTGCGTGAAGCAGGAGATACCTTACCAGGACATTGA

TATTGAGCTACAAAAGGACATACAAAGAAGGGCCAAACACACCAAACGTACCCATTATGACAGAAAAAAT

GCACCTATGGAGTCCGGGGAGGAGGAATTTCTGTTGTAA

SEQ ID NO: 16
DNA sequence of aminoacid sequence SEQ ID NO: 5
>gi|28373214: UL33. 43066-44425 Human herpesvirus 5 (laboratory strain AD169)
ATGGACACCATCATCCACAACTCGGTGAGCGCCCCACCTAGAGGGAGGGGGGGTAGTTTAATAGCGGAGG

CGGATACGCGGTTTTCTTTTAAGCGCCGCTGACTTGTTTCTTCTGTTTTTTCGCCCCGTGTGCTGTTCCG

CCCAGACCCGCAACAACACTCCTCCGCACATCAATGACACTTGCAACATGACAGGGCCGCTATTCGCCAT

TCGAACCACCGAAGCCGTACTCAACACATTCATCATCTTCGTGGGCGGTCCACTTAACGCCATAGTGTTG

ATCACGCAGCTGCTCACGAATCGCGTGCTTGGCTATTCGACGCCCACCATTTACATGACCAACCTCTACT

CTACTAATTTTCTCACGCTTACTGTGCTACCCTTTATCGTACTCAGCAACCAGTGGCTGTTGCCGGCCGG

CGTGGCCTCGTGTAAATTTCTATCGGTGATCTACTACTCAAGCTGCACAGTGGGCTTTGCCACCGTAGCT

CTGATCGCCGCCGATCGTTATCGCGTCCTTCATAAACGAACATACGCACGCCAATCATACCGTTCAACCT

ATATGATTTTGCTATTGACATGGCTCGCTGGACTAATTTTTTCCGTGCCCGCAGCTGTTTACACCACGGT

GGTGATGCATCACGATGCCAACGATACCAATAATACTAATGGGCACGCCACCTGTGTACTGTACTTCGTA

GCTGAAGAAGTGCACACAGTGCTGCTTTCGTGGAAAGTGCTGCTGACGATGGTATGGGGTGCCGCACCCG

TGATAATGATGACGTGGTTCTACGCATTCTTCTACTCAACCGTACAGCGCACGTCACAGAAACAAAGGAG

TCGTACCTTAACCTTTGTTAGCGTGCTACTCATCTCCTTCGTGGCGCTACAAACTCCCTACGTCTCTCTC

ATGATCTTCAACAGTTATGCCACAACCGCCTGGCCCATGCAGTGTGAACACCTCACACTGCGACGCACCA

TTGGCACGCTGGCGCGTGTGGTGCCCCACCTACACTGCCTCATTAATCCCATCCTGTACGCGCTGCTGGG

TCATGATTTTCTGCAACGCATGCGGCAGTGTTTCCGCGGTCAGTTGCTGGACCGCCGCGCTTTCCTGAGA

TCGCAGCAGAATCAGCGAGCTACAGCGGAGACAAATCTAGCGGCTGGCAACAATTCACAATCAGTGGCTA

CGTCATTAGACACCAATAGCAAAAACTACAATCAGCACGCCAAACGCAGCGTGTCTTTCAATTTTCCCAG

CGGTACGTGGAAAGGCGGCCAGAAAACCGCGTCCAACGACACATCCACAAAAATCCCCCATCGACTCTCA

CAATCGCATCATAACCTCAGCGGGGTATGA

SEQ ID NO: 17
DNA sequence of aminoacid sequence SEQ ID NO: 6
>gi|28373214: UL78. 113855-115150 Human herpesvirus 5 (laboratory strain AD169)
ATGTCCCCTTCTGTGGAGGAGACTACCTCAGTCACCGAGTCCATCATGTTCGCTATTGTGAGTTTCAAAC

ACATGGGCCCGTTCGAAGGCTACTCTATGTCGGCCGATCGCGCCGCCTCGGATCTACTCATCGGCATGTT

CGGCTCCGTTAGCCTGGTCAACCTGCTGACTATCATCGGTTGCCTCTGGGTGTTGCGTGTTACGCGGCCG

CCCGTGTCCGTGATGATTTTTACTTGGAATCTGGTACTTAGTCAGTTTTTTTCCATCCTGGCCACCATGT

TGTCCAAGGGTATCATGCTGCGTGGCGCTCTAAATCTCAGCCTCTGTCGCTTAGTGCTCTTTGTCGACGA

CGTGGGCCTATATTCGACGGCGTTGTTTTTCCTCTTTCTGATACTGGATCGTCTGTCGGCCATATCTTAC

GGCCGTGATCTCTGGCATCATGAGACGCGCGAAAACGCCGGCGTGGCGCTCTACGCGGTCGCCTTTGCCT

GGGTTCTTTCCATCGTAGCCGCTGTGCCCACCGCCGCTACGGGTTCACTGGACTACCGTTGGCTAGGCTG

TCAGATCCCTATACAGTATGCCGCGGTGGACCTCACCATCAAGATGTGGTTTTTGCTGGGGGCGCCCATG

ATCGCCGTACTGGCTAACGTGGTAGAGTTGGCCTACAGCGATCGGCGCGACCACGTCTGGTCCTACGTGG

```
GTCGTGTCTGCACCTTCTACGTGACGTGTCTCATGCTGTTTGTGCCCTACTACTGCTTCAGAGTCCTACG

CGGTGTACTGCAGCCCGCTAGCGCGGCCGGCACCGGTTTCGGCATTATGGATTACGTGGAATTGGCTACG

CGTACCCTTCTCACCATGCGTCTTGGCATTCTGCCGCTCTTTATCATTGCGTTCTTCTCCCGCGAGCCCA

CCAAGGATCTGGATGACTCCTTTGATTATCTGGTCGAGAGATGTCAGCAAAGCTGCCACGGTCATTTCGT

ACGTCGGTTGGTGCAGGCGTTGAAGCGGGCTATGTATAGCGTGGAGCTGGCCGTGTGTTACTTTTCTACG

TCCGTCCGAGACGTCGCCGAGGCGGTGAAAAAGTCCTCCAGCCGTTGTTACGCCGACGCGACGTCGGCGG

CCGTTGTGGTAACGACAACCACGTCGGAGAAAGCCACGTTGGTGGAGCACGCGGAAGGCATGGCTTCCGA

AATGTGTCCTGGGACTACGATCGATGTTTCGGCCGAAAGTTCCTCCGTCCTCTGCACCGACGGCGAAAAC

ACCGTCGCGTCGGACGCGACGGTGACGGCATTATGA
```

SEQ ID NO: 18
DNA sequence of aminoacid sequence SEQ ID NO: 7
>gi|18845965: vMIP2/vCCl2. c21832-21548 Human herpesvirus 8, genome
```
ATGGACACCAAGGGCATCCTGCTCGTCGCTGTGCTGACTGCCCTTGCTTTGTTTGCAATCTGGGGACACGC

TGGGAGCGTCCTGGCATAGACCGGACAAGTGCTGTCTCGGTTACCAGAAAAGACCATTACCACAGGTGCT

TCTGTCCAGCTGGTACCCCACCTCCCAACTGTGCAGCAAGCCGGGTGTGATATTTTTGACAAAGCGTGGT

CGCCAGGTGTGTGCCGACAAATCGAAAGACTGGGTGAAGAAGCTGATGCAGCAATTACCAGTCACTGCTC

GCTGA
```

SEQ ID NO: 19
DNA sequence of aminoacid sequence SEQ ID NO: 8
>gi|151215|gb|K01397.1|PSEETA Pseudomonas aeruginosa exotoxin type A,
compl. cds
```
ATGCACCTGATACCCCATTGGATCCCCCTGGTCGCCAGCCTCGGCCTGCTCGCCGGCGGCTCGTCCGCGT

CCGCCGCCGAGGAAGCCTTCGACCTCTGGAACGAATGCGCCAAAGCCTGCGTGCTCGACCTCAAGGACGG

CGTGCGTTCCAGCCGCATGAGCGTCGACCCGGCCATCGCCGACACCAACGGCCAGGGCGTGCTGCACTAC

TCCATGGTCCTGGAGGGCGGCAACGACGCGCTCAAGCTGGCCATCGACAACGCCCTCAGCATCACCAGCG

ACGGCCTGACCATCCGCCTCGAAGGCGGCGTCGAGCCGAACAAGCCGGTGCGCTACAGCTACACGCGCCA

GGCGCGCGGCAGTTGGTCGCTGAACTGGCTGGTACCGATCGGCCACGAGAAGCCCTCGAACATCAAGGTG

TTCATCCACGAACTGAACGCCGGCAACCAGCTCAGCCACATGTCGCCGATCTACACCATCGAGATGGGCG

ACGAGTTGCTGGCGAAGCTGGCGCGCGATGCCACCTTCTTCGTCAGGGCGCACGAGAGCAACGAGATGCA

GCCGACGCTCGCCATCAGCCATGCCGGGGTCAGCGTGGTCATGGCCCAGACCCAGCCGCGCCGGGAAAAG

CGCTGGAGCGAATGGGCCAGCGGCAAGGTGTTGTGCCTGCTCGACCCGCTGGACGGGGTCTACAACTACC

TCGCCCAGCAACGCTGCAACCTCGACGATACCTGGGAAGGCAAGATCTACCGGGTGCTCGCCGGCAACCC

GGCGAAGCATGACCTGGACATCAAACCCACGGTCATCAGTCATCGCCTGCACTTTCCCGAGGGCGGCAGC

CTGGCCGCGCTGACCGCGCACCAGGCTTGCCACCTGCCGCTGGAGACTTTCACCCGTCATCGCCAGCCGC

GCGGCTGGGAACAACTGGAGCAGTGCGGCTATCCGGTGCAGCGGCTGGTCGCCCTCTACCTGGCGGCGCG

GCTGTCGTGGAACCAGGTCGACCAGGTGATCCGCAACGCCCTGGCCAGCCCCGGCAGCGGCGGCGACCTG

GGCGAAGCGATCCGCGAGCAGCCGGAGCAGGCCCGTCTGGCCCTGACCCTGGCCGCCGCCGAGAGCGAGC

GCTTCGTCCGGCAGGGCACCGGCAACGACGAGGCCGGCGCGGCCAACGCCGACGTGGTGAGCCTGACCTG

CCCGGTCGCCGCCGGTGAATGCGCGGGCCCGGCGGACAGCGGCGACGCCCTGCTGGAGCGCAACTATCCC

ACTGGCGCGGAGTTCCTCGGCGACGGCGGCGACGTCAGCTTCAGCACCCGCGGCACGCAGAACTGGACGG

TGGAGCGGCTGCTCCAGGCGCACCGCCAACTGGAGGAGCGCGGCTATGTGTTCGTCGGCTACCACGGCAC

CTTCCTCGAAGCGGCGCAAAGCATCGTCTTCGGCGGGGTGCGCGCGCGCAGCCAGGACCTCGACGCGATC

TGGCGCGGTTTCTATATCGCCGGCGATCCGGCGCTGGCCTACGGCTACGCCCAGGACCAGGAACCCGACG

CACGCGGCCGGATCCGCAACGGTGCCCTGCTGCGGGTCTATGTGCCGCGCTCGAGCCTGCCGGGCTTCTA
```

-continued

CCGCACCAGCCTGACCCTGGCCGCGCCGGAGGCGGCGGGCGAGGTCGAACGGCTGATCGGCCATCCGCTG

CCGCTGCGCCTGGACGCCATCACCGGCCCCGAGGAGGAAGGCGGGCGCCTGGAGACCATTCTCGGCTGGC

CGCTGGCCGAGCGCACCGTGGTGATTCCCTCGGCGATCCCCACCGACCCGCGCAACGTCGGCGGCGACCT

CGACCCGTCCAGCATCCCCGACAAGGAACAGGCGATCAGCGCCCTGCCGGACTACGCCAGCCAGCCCGGC

AAACCGCCGCGCGAGGACCTGAAGTAA

SEQ ID NO: 20

DNA sequence of aminoacid sequence SEQ ID NO: 9
>Exotoxin A (version P38KDEL)
GAGGGCGGCAGCCTGGCCGCGCTGACCGCGCACCAGGCTTGCCACCTGCCGCTGGAGACTTTCACCCGTC

ATCGCCAGCCGCGCGGCTGGGAACAACTGGAGCAGTGCGGCTATCCGGTGCAGCGGCTGGTCGCCCTCTA

CCTGGCGGCGCGGCTGTCGTGGAACCAGGTCGACCAGGTGATCCGCAACGCCCTGGCCAGCCCCGGCAGC

GGCGGCGACCTGGGCGAAGCGATCCGCGAGCAGCCGGAGCAGGCCCGTCTGGCCCTGACCCTGGCCGCCG

CCGAGAGCGAGCGCTTCGTCCGGCAGGGCACCGGCAACGACGAGGCCGGCGCGGCCAACGCCGACGTGGT

GAGCCTGACCTGCCCGGTCGCCGCCGGTGAATGCGCGGGCCCGGCGGACAGCGGCGACGCCCTGCTGGAG

CGCAACTATCCCACTGGCGCGGAGTTCCTCGGCGACGGCGGCGACGTCAGCTTCAGCACCCGCGGCACGC

AGAACTGGACGGTGGAGCGGCTGCTCCAGGCGCACCGCCAACTGGAGGAGCGCGGCTATGTGTTCGTCGG

CTACCACGGCACCTTCCTCGAAGCGGCGCAAAGCATCGTCTTCGGCGGGGTGCGCGCGCGCAGCCAGGAC

CTCGACGCGATCTGGCGCGGTTTCTATATCGCCGGCGATCCGGCGCTGGCCTACGGCTACGCCCAGGACC

AGGAACCCGACGCACGCGGCCGGATCCGCAACGGTGCCCTGCTGCGGGTCTATGTGCCGCGCTCGAGCCT

GCCGGGCTTCTACCGCACCAGCCTGACCCTGGCCGCGCCGGAGGCGGCGGGCGAGGTCGAACGGCTGATC

GGCCATCCGCTGCCGCTGCGCCTGGACGCCATCACCGGCCCCGAGGAGGAAGGCGGGCGCCTGGAGACCA

TTCTCGGCTGGCCGCTGGCCGAGCGCACCGTGGTGATTCCCTCGGCGATCCCCACCGACCCGCGCAACGT

CGGCGGCGACCTCGACCCGTCCAGCATCCCCGACAAGGAACAGGCGATCAGCGCCCTGCCGGACTACGCC

AGCCAGCCCGGCAAACCGCCGAAAGACGAGCTCTAA

SEQ ID NO: 21

DNA sequence of aminoacid sequence SEQ ID NO: 10
>CX3CL1(full length, mature peptide)-PE38KDEL fusion protein
CAGCACCACGGTGTGACGAAATGCAACATCACGTGCAGCAAGATGACATCAAAGATACCTGTAGCTTTGC

TCATCCACTATCAACAGAACCAGGCATCATGCGGCAAACGCGCAATCATCTTGGAGACGAGACAGCACAG

GCTGTTCTGTGCCGACCCGAAGGAGCAATGGGTCAAGGACGCGATGCAGCATCTGGACCGCCAGGCTGCT

GCCCTAACTCGAAATGGCGGCACCTTCGAGAAGCAGATCGGCGAGGTGAAGCCCAGGACCACCCCTGCCG

CCGGGGGAATGGACGAGTCTGTGGTCCTGGAGCCCGAAGCCACAGGCGAAAGCAGTAGCCTGGAGCCGAC

TCCTTCTTCCCAGGAAGCACAGAGGGCCCTGGGGACCTCCCCAGAGCTGCCGACGGGCGTGACTGGTTCC

TCAGGGACCAGGCTCCCCCCGACGCCAAAGGCTCAGGATGGAGGGCCTGTGGGCACGGAGCTTTTCCGAG

TGCCTCCCGTCTCCACTGCCGCCACGTGGCAGAGTTCTGCTCCCCACCAACCTGGGCCCAGCCTCTGGGC

TGAGGCAAAGACCTCTGAGGCCCCGTCCACCCAGGACCCCTCCACCCAGGCCTCCACTGCGTCCTCCCCA

GCCCCAGAGGAGAATGCTCCGTCTGAAGGCCAGCGTGTGTGGGGTCAGGGACAGAGCCCCAGGCCAGAGA

ACTCTCTGGAGCGGGAGGAGATGGGTCCCGTGCCAGCGCACACGGATGCCTTCCAGGACTGGGGGCCTGG

CAGCATGGCCCACGTCTCTGTGGTCCCTGTCTCCTCAGAAGGGACCCCCAGCAGGGAGCCAGTGGCTTCA

GGCAGCTGGACCCCTAAGGCTGAGGAACCCATCCATGCCACCATGGACCCCCAGAGGCTGGGCGTCCTTA

TCACTCCTGTCCCTGACGCCCAGGCTGCCACCCGGAGGCAGGCGGTGGGGCTGCTGGCCTTCCTTGGCCT

-continued

CCTCTTCTGCCTGGGGGTGGCCATGTTCACCTACCAGAGCCTCCAGGGCTGCCCTCGAAAGATGGCAGGA

GAGATGGCGGAGGGCCTTCGCTACATCCCCCGGAGCTGTGGTAGTAATTCATATGTCCTGGTGCCCGTGG

AGGGCGGCAGCCTGGCCGCGCTGACCGCGCACCAGGCTTGCCACCTGCCGCTGGAGACTTTCACCCGTCA

TCGCCAGCCGCGCGGCTGGGAACAACTGGAGCAGTGCGGCTATCCGGTGCAGCGGCTGGTCGCCCTCTAC

CTGGCGGCGCGGCTGTCGTGGAACCAGGTCGACCAGGTGATCCGCAACGCCCTGGCCAGCCCCGGCAGCG

GCGGCGACCTGGGCGAAGCGATCCGCGAGCAGCCGGAGCAGGCCCGTCTGGCCCTGACCCTGGCCGCCGC

CGAGAGCGAGCGCTTCGTCCGGCAGGGCACCGGCAACGACGAGGCCGGCGCGGCCAACGCCGACGTGGTG

AGCCTGACCTGCCCGGTCGCCGCCGGTGAATGCGCGGGCCCGGCGGACAGCGGCGACGCCCTGCTGGAGC

GCAACTATCCCACTGGCGCGGAGTTCCTCGGCGACGGCGGCGACGTCAGCTTCAGCACCCGCGGCACGCA

GAACTGGACGGTGGAGCGGCTGCTCCAGGCGCACCGCCAACTGGAGGAGCGCGGCTATGTGTTCGTCGGC

TACCACGGCACCTTCCTCGAAGCGGCGCAAAGCATCGTCTTCGGCGGGGTGCGCGCGCGCAGCCAGGACC

TCGACGCGATCTGGCGCGGTTTCTATATCGCCGGCGATCCGGCGCTGGCCTACGGCTACGCCCAGGACCA

GGAACCCGACGCACGCGGCCGGATCCGCAACGGTGCCCTGCTGCGGGTCTATGTGCCGCGCTCGAGCCTG

CCGGGCTTCTACCGCACCAGCCTGACCCTGGCCGCGCCGGAGGCGGCGGGCGAGGTCGAACGGCTGATCG

GCCATCCGCTGCCGCTGCGCCTGGACGCCATCACCGGCCCCGAGGAGGAAGGCGGGCGCCTGGAGACCAT

TCTCGGCTGGCCGCTGGCCGAGCGCACCGTGGTGATTCCCTCGGCGATCCCCACCGACCCGCGCAACGTC

GGCGGCGACCTCGACCCGTCCAGCATCCCCGACAAGGAACAGGCGATCAGCGCCCTGCCGGACTACGCCA

GCCAGCCCGGCAAACCGCCGAAAGACGAGCTCTAA

SEQ ID NO: 22
DNA sequence of aminoacid sequence SEQ ID NO: 11
>CX3CL1(chemokines domain)-PE38KDEL fusion protein
CAGCACCACGGTGTGACGAAATGCAACATCACGTGCAGCAAGATGACATCAAAGATACCTGTAGCTTTGC

TCATCCACTATCAACAGAACCAGGCATCATGCGGCAAACGCGCAATCATCTTGGAGACGAGACAGCACAG

GCTGTTCTGTGCCGACCCGAAGGAGCAATGGGTCAAGGACGCGATGCAGCATCTGGACCGCCAGGCTGCT

GCCCTAACTCGAAATGGCGAGGGCGGCAGCCTGGCCGCGCTGACCGCGCACCAGGCTTGCCACCTGCCGC

TGGAGACTTTCACCCGTCATCGCCAGCCGCGCGGCTGGGAACAACTGGAGCAGTGCGGCTATCCGGTGCA

GCGGCTGGTCGCCCTCTACCTGGCGGCGCGGCTGTCGTGGAACCAGGTCGACCAGGTGATCCGCAACGCC

CTGGCCAGCCCCGGCAGCGGCGGCGACCTGGGCGAAGCGATCCGCGAGCAGCCGGAGCAGGCCCGTCTGG

CCCTGACCCTGGCCGCCGCCGAGAGCGAGCGCTTCGTCCGGCAGGGCACCGGCAACGACGAGGCCGGCGC

GGCCAACGCCGACGTGGTGAGCCTGACCTGCCCGGTCGCCGCCGGTGAATGCGCGGGCCCGGCGGACAGC

GGCGACGCCCTGCTGGAGCGCAACTATCCCACTGGCGCGGAGTTCCTCGGCGACGGCGGCGACGTCAGCT

TCAGCACCCGCGGCACGCAGAACTGGACGGTGGAGCGGCTGCTCCAGGCGCACCGCCAACTGGAGGAGCG

CGGCTATGTGTTCGTCGGCTACCACGGCACCTTCCTCGAAGCGGCGCAAAGCATCGTCTTCGGCGGGGTG

CGCGCGCGCAGCCAGGACCTCGACGCGATCTGGCGCGGTTTCTATATCGCCGGCGATCCGGCGCTGGCCT

ACGGCTACGCCCAGGACCAGGAACCCGACGCACGCGGCCGGATCCGCAACGGTGCCCTGCTGCGGGTCTA

TGTGCCGCGCTCGAGCCTGCCGGGCTTCTACCGCACCAGCCTGACCCTGGCCGCGCCGGAGGCGGCGGGC

GAGGTCGAACGGCTGATCGGCCATCCGCTGCCGCTGCGCCTGGACGCCATCACCGGCCCCGAGGAGGAAG

GCGGGCGCCTGGAGACCATTCTCGGCTGGCCGCTGGCCGAGCGCACCGTGGTGATTCCCTCGGCGATCCC

CACCGACCCGCGCAACGTCGGCGGCGACCTCGACCCGTCCAGCATCCCCGACAAGGAACAGGCGATCAGC

GCCCTGCCGGACTACGCCAGCCAGCCCGGCAAACCGCCGAAAGACGAGCTCTAA

The invention claimed is:

1. An immunotoxin comprising (a) a ligand which is a variant of a $CX_3C$ chemokine that binds a constitutively internalizing CMV encoded chemokine receptor US28 expressed on a CMV infected cell and (b) a toxin that is cytotoxic to the CMV infected cell, wherein the ligand has increased specificity towards US28 as compared to the parental ligand and the ligand is a variant having at least 80% amino acid sequence identity to amino acids present at positions 25-100 of SEQ ID NO: 2 in the chemokine domain of human $CX_3CL1$; and (i) the ligand is a variant mutated in position 31 of SEQ ID NO: 2, a variant mutated in position 38 of SEQ ID NO: 2, a variant mutated in position 60 of SEQ ID NO: 2, a variant mutated in position 68 of SEQ ID NO: 2, a variant mutated in position 71 of SEQ ID NO: 2, or a variant mutated in position 73 of SEQ ID NO: 2; or (ii) the ligand is a variant at one or more of amino acid residues in positions 33, 34 and 35 of SEQ ID NO: 2, wherein the one or more residues have been mutated or deleted.

2. The immunotoxin according to claim 1, wherein the ligand is a chimera between the $CX_3C$ chemokine and a chemokine selected from the group consisting of CC-chemokines, XC-chemokines and CXC-chemokines.

3. The immunotoxin according to claim 1, wherein the ligand is a variant which has at least 90% amino acid sequence identity to amino acids present at positions 25-100 of SEQ ID NO: 2 in the chemokine domain of human $CX_3CL1$.

4. The immunotoxin according to claim 1, wherein the ligand is selected from the group consisting of the following variants: a variant mutated in position 31 of SEQ ID NO: 2 to an Alanine, a variant mutated in position 31 of SEQ ID NO: 2 to an Glutamate, a variant in position 38 of SEQ ID NO: 2 to an Alanine, a variant mutated in position 38 of SEQ ID NO: 2 to a Glutamate, a variant mutated in position 60 of SEQ ID NO: 2 to a Alanine, a variant mutated in position 60 of SEQ ID NO: 2 to a Glutamate, a variant mutated in position 68 of SEQ ID NO: 2 to a Alanine, a variant mutated in position 68 of SEQ ID NO: 2 to a Glutamate, a variant mutated in position 71 of SEQ ID NO: 2 to a Alanine, a variant mutated in position 71 of SEQ ID NO: 2 to a Glutamate, a variant mutated in position 71 of SEQ ID NO: 2 to a Glutamine, a variant mutated in position 73 of SEQ ID NO: 2 to a Alanine and a variant mutated in position 73 of SEQ ID NO: 2 to a Leucine.

5. The immunotoxin according to claim 1, wherein the ligand binds to US28 with a Kd of $10^{-8}$ M or less.

6. The immunotoxin according to claim 5, wherein the ligand has at least one binding effect selected from those consisting of (i) binding to the US28 receptor with a Kd of less than $10^{-9}$ M; and (ii) binding to the $CX_3CR1$ receptor with a Kd of $10^{-6}$ M or more.

7. The immunotoxin according to claim 1, wherein the toxin is selected from the group consisting of gelonin, bouganin, saporin, ricin, ricin A chain, bryodin, diphtheria, restrictocin, diphtheria toxin, Pseudomonas exotoxin A and variants thereof.

8. The immunotoxin according to claim 7, wherein the toxin is Pseudomonas exotoxin A or a variant thereof.

9. The immunotoxin according to claim 8, wherein the toxin is Pseudomonas exotoxin A variant PE38 KDEL of SEQ ID NO: 9.

10. A pharmaceutical composition comprising an immunotoxin according to claim 1, or a physiological acceptable salt thereof, and a pharmaceutical acceptable carrier.

11. The pharmaceutical composition according to claim 10, wherein the composition further comprises at least one anti-viral or immunosuppressive therapeutic agent.

12. A kit for treatment of CMV infection comprising (a) an effective amount of an immunotoxin according to claim 1 and (b) an antiviral or immuno-suppressive therapeutic, wherein (a) and (b) are for simultaneous, separate or sequential administration.

13. The immunotoxin according to claim 1, wherein the ligand binds to the US28 receptor with a Kd of less than $10^{-9}$ M.

14. The immunotoxin according to claim 1, wherein the ligand binds to the CX3CR1 receptor with a Kd of $10^{-6}$ M or more.

15. The immunotoxin according to claim 1, wherein the ligand is selected from the group consisting of the following variants: a variant mutated in position 31 of SEQ ID NO:2 to an Alanine, a variant mutated in position 31 of SEQ ID NO:2 to an Glutamate, a variant in position 38 of SEQ ID NO:2 to an Alanine, a variant mutated in position 38 of SEQ ID NO:2 to a Glutamate, a variant mutated in position 42 of SEQ ID NO:2 to an Alanine, a variant mutated in position 42 of SEQ ID NO:2 to a Glutamate, a variant mutated in position 60 of SEQ ID NO:2 to a Alanine, a variant mutated in position 60 of SEQ ID NO:2 to a Glutamate, a variant mutated in position 61 of SEQ ID NO:2 to a Alanine, a variant mutated in position 61 of SEQ ID NO:2 to a Glutamate, a variant mutated in position 68 of SEQ ID NO:2 to a Alanine, a variant mutated in position 68 of SEQ ID NO:2 to a Glutamate, a variant mutated in position 71 of SEQ ID NO:2 to a Alanine, a variant mutated in position 71 of SEQ ID NO:2 to a Glutamate, a variant mutated in position 71 of SEQ ID NO:2 to a Glutamine, a variant mutated in position 72 of SEQ ID NO:2 to a Alanine, a variant mutated in position 73 of SEQ ID NO:2 to a Alanine and a variant mutated in position 73 of SEQ ID NO:2 to a Leucine.

\* \* \* \* \*

UNITED STATES PATENT AND TRADEMARK OFFICE
CERTIFICATE OF CORRECTION

PATENT NO.       : 8,592,554 B2                                                  Page 1 of 1
APPLICATION NO. : 12/306395
DATED            : November 26, 2013
INVENTOR(S)      : Kledal et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1330 days.

Signed and Sealed this

Twenty-second Day of September, 2015

Michelle K. Lee
*Director of the United States Patent and Trademark Office*

SEQUENCE LISTING

<160> NUMBER OF SEQ ID NOS: 23

<210> SEQ ID NO 1
<211> LENGTH: 429
<212> TYPE: PRT
<213> ORGANISM: Artificial Sequence
<220> FEATURE:
<223> OTHER INFORMATION: Synthetic sequence

<400> SEQUENCE: 1

```
Ser Pro Tyr Ser Ser Asp Thr Thr Pro Cys Cys Phe Ala Tyr Ile Ala
 1               5                  10                  15

Arg Pro Leu Pro Arg Ala His Ile Lys Glu Tyr Phe Tyr Thr Ser Gly
            20                  25                  30

Lys Cys Ser Asn Pro Ala Val Val Phe Val Thr Arg Lys Asn Arg Gln
        35                  40                  45

Val Cys Ala Asn Pro Glu Lys Lys Trp Val Arg Glu Tyr Ile Asn Ser
 50                  55                  60

Leu Glu Met Ser Glu Gly Gly Ser Leu Ala Ala Leu Thr Ala His Gln
 65                  70                  75                  80

Ala Cys His Leu Pro Leu Glu Thr Phe Thr Arg His Arg Gln Pro Arg
                85                  90                  95

Gly Trp Glu Gln Leu Glu Gln Cys Gly Tyr Pro Val Gln Arg Leu Val
            100                 105                 110

Ala Leu Tyr Leu Ala Ala Arg Leu Ser Trp Asn Gln Val Asp Gln Val
        115                 120                 125

Ile Arg Asn Ala Leu Ala Ser Pro Gly Ser Gly Gly Asp Leu Gly Glu
130                 135                 140

Ala Ile Arg Glu Gln Pro Glu Gln Ala Arg Leu Ala Leu Thr Leu Ala
145                 150                 155                 160

Ala Ala Glu Ser Glu Arg Phe Val Arg Gln Thr Gly Asn Asp Glu
                165                 170                 175

Ala Gly Ala Ala Asn Ala Asp Val Val Ser Leu Thr Cys Pro Val Ala
            180                 185                 190

Ala Gly Glu Cys Ala Gly Pro Ala Asp Ser Gly Asp Ala Leu Leu Glu
        195                 200                 205

Arg Asn Tyr Pro Thr Gly Ala Glu Phe Leu Gly Asp Gly Gly Asp Val
210                 215                 220

Ser Phe Ser Thr Arg Gly Thr Gln Asn Trp Thr Val Glu Arg Leu Leu
225                 230                 235                 240

Gln Ala His Arg Gln Leu Glu Glu Arg Gly Tyr Val Phe Val Gly Tyr
                245                 250                 255

His Gly Thr Phe Leu Glu Ala Ala Gln Ser Ile Val Phe Gly Gly Val
            260                 265                 270

Arg Ala Arg Ser Gln Asp Leu Asp Ala Ile Trp Arg Gly Phe Tyr Ile
        275                 280                 285

Ala Gly Asp Pro Ala Leu Ala Tyr Gly Tyr Ala Gln Asp Gln Glu Pro
290                 295                 300

Asp Ala Arg Gly Arg Ile Arg Asn Gly Ala Leu Leu Arg Val Tyr Val
305                 310                 315                 320

Pro Arg Ser Ser Leu Pro Gly Phe Tyr Arg Thr Ser Leu Thr Leu Ala
                325                 330                 335

Ala Pro Glu Ala Ala Gly Glu Val Glu Arg Leu Ile Gly His Pro Leu
            340                 345                 350
```

```
Pro Leu Arg Leu Asp Ala Ile Thr Gly Pro Glu Glu Glu Gly Gly Arg
        355                 360                 365

Leu Glu Thr Ile Leu Gly Trp Pro Leu Ala Glu Arg Thr Val Val Ile
370                 375                 380

Pro Ser Ala Ile Pro Thr Asp Pro Arg Asn Val Gly Gly Asp Leu Asp
385                 390                 395                 400

Pro Ser Ser Ile Pro Asp Lys Glu Gln Ala Ile Ser Ala Leu Pro Asp
            405                 410                 415

Tyr Ala Ser Gln Pro Gly Lys Pro Pro Lys Asp Glu Leu
            420                 425

<210> SEQ ID NO 2
<211> LENGTH: 397
<212> TYPE: PRT
<213> ORGANISM: Homo sapiens

<400> SEQUENCE: 2

Met Ala Pro Ile Ser Leu Ser Trp Leu Leu Arg Leu Ala Thr Phe Cys
1               5                   10                  15

His Leu Thr Val Leu Leu Ala Gly Gln His His Gly Val Thr Lys Cys
            20                  25                  30

Asn Ile Thr Cys Ser Lys Met Thr Ser Lys Ile Pro Val Ala Leu Leu
        35                  40                  45

Ile His Tyr Gln Gln Asn Gln Ala Ser Cys Gly Lys Arg Ala Ile Ile
    50                  55                  60

Leu Glu Thr Arg Gln His Arg Leu Phe Cys Ala Asp Pro Lys Glu Gln
65                  70                  75                  80

Trp Val Lys Asp Ala Met Gln His Leu Asp Arg Gln Ala Ala Ala Leu
                85                  90                  95

Thr Arg Asn Gly Gly Thr Phe Glu Lys Gln Ile Gly Glu Val Lys Pro
            100                 105                 110

Arg Thr Thr Pro Ala Ala Gly Gly Met Asp Glu Ser Val Val Leu Glu
        115                 120                 125

Pro Glu Ala Thr Gly Glu Ser Ser Ser Leu Glu Pro Thr Pro Ser Ser
    130                 135                 140

Gln Glu Ala Gln Arg Ala Leu Gly Thr Ser Pro Glu Leu Pro Thr Gly
145                 150                 155                 160

Val Thr Gly Ser Ser Gly Thr Arg Leu Pro Pro Thr Pro Lys Ala Gln
                165                 170                 175

Asp Gly Gly Pro Val Gly Thr Glu Leu Phe Arg Val Pro Pro Val Ser
            180                 185                 190

Thr Ala Ala Thr Trp Gln Ser Ser Ala Pro His Gln Pro Gly Pro Ser
        195                 200                 205

Leu Trp Ala Glu Ala Lys Thr Ser Glu Ala Pro Ser Thr Gln Asp Pro
    210                 215                 220

Ser Thr Gln Ala Ser Thr Ala Ser Ser Pro Ala Pro Glu Glu Asn Ala
225                 230                 235                 240

Pro Ser Glu Gly Gln Arg Val Trp Gly Gln Gly Gln Ser Pro Arg Pro
                245                 250                 255

Glu Asn Ser Leu Glu Arg Glu Glu Met Gly Pro Val Pro Ala His Thr
            260                 265                 270

Asp Ala Phe Gln Asp Trp Gly Pro Gly Ser Met Ala His Val Ser Val
        275                 280                 285

Val Pro Val Ser Ser Glu Gly Thr Pro Ser Arg Glu Pro Val Ala Ser
    290                 295                 300
```

```
Gly Ser Trp Thr Pro Lys Ala Glu Pro Ile His Ala Thr Met Asp
305                 310                 315                 320

Pro Gln Arg Leu Gly Val Leu Ile Thr Pro Val Pro Asp Ala Gln Ala
            325                 330                 335

Ala Thr Arg Arg Gln Ala Val Gly Leu Leu Ala Phe Leu Gly Leu Leu
            340                 345                 350

Phe Cys Leu Gly Val Ala Met Phe Thr Tyr Gln Ser Leu Gln Gly Cys
        355                 360                 365

Pro Arg Lys Met Ala Gly Glu Met Ala Glu Gly Leu Arg Tyr Ile Pro
    370                 375                 380

Arg Ser Cys Gly Ser Asn Ser Tyr Val Leu Val Pro Val
385                 390                 395

<210> SEQ ID NO 3
<211> LENGTH: 354
<212> TYPE: PRT
<213> ORGANISM: Human herpesvirus 5

<400> SEQUENCE: 3

Met Thr Pro Thr Thr Thr Thr Ala Glu Leu Thr Thr Glu Phe Asp Tyr
1               5                   10                  15

Asp Glu Asp Ala Thr Pro Cys Val Phe Thr Asp Val Leu Asn Gln Ser
            20                  25                  30

Lys Pro Val Thr Leu Phe Leu Tyr Gly Val Val Phe Leu Phe Gly Ser
        35                  40                  45

Ile Gly Asn Phe Leu Val Ile Phe Thr Ile Thr Trp Arg Arg Arg Ile
    50                  55                  60

Gln Cys Ser Gly Asp Val Tyr Phe Ile Asn Leu Ala Ala Ala Asp Leu
65                  70                  75                  80

Leu Phe Val Cys Thr Leu Pro Leu Trp Met Gln Tyr Leu Leu Asp His
                85                  90                  95

Asn Ser Leu Ala Ser Val Pro Cys Thr Leu Leu Thr Ala Cys Phe Tyr
            100                 105                 110

Val Ala Met Phe Ala Ser Leu Cys Phe Ile Thr Glu Ile Ala Leu Asp
        115                 120                 125

Arg Tyr Tyr Ala Ile Val Tyr Met Arg Tyr Arg Pro Val Lys Gln Ala
    130                 135                 140

Cys Leu Phe Ser Ile Phe Trp Trp Ile Phe Ala Val Ile Ile Ala Ile
145                 150                 155                 160

Pro His Phe Met Val Val Thr Lys Lys Asp Asn Gln Cys Met Thr Asp
                165                 170                 175

Tyr Asp Tyr Leu Glu Val Ser Tyr Pro Ile Ile Leu Asn Val Glu Leu
            180                 185                 190

Met Leu Gly Ala Phe Val Ile Pro Leu Ser Val Ile Ser Tyr Cys Tyr
        195                 200                 205

Tyr Arg Ile Ser Arg Ile Val Ala Val Ser Gln Ser Arg His Lys Gly
    210                 215                 220

Arg Ile Val Arg Val Leu Ile Ala Val Val Leu Val Phe Ile Ile Phe
225                 230                 235                 240

Trp Leu Pro Tyr His Leu Thr Leu Phe Val Asp Thr Leu Lys Leu Leu
                245                 250                 255

Lys Trp Ile Ser Ser Ser Cys Glu Phe Glu Arg Ser Leu Lys Arg Ala
            260                 265                 270

Leu Ile Leu Thr Glu Ser Leu Ala Phe Cys His Cys Cys Leu Asn Pro
        275                 280                 285
```

-continued

Leu Leu Tyr Val Phe Val Gly Thr Lys Phe Arg Gln Glu Leu His Cys
290                 295                 300

Leu Leu Ala Glu Phe Arg Gln Arg Leu Phe Ser Arg Asp Val Ser Trp
305                 310                 315                 320

Tyr His Ser Met Ser Phe Ser Arg Arg Ser Ser Pro Ser Arg Arg Glu
                325                 330                 335

Thr Ser Ser Asp Thr Leu Ser Asp Glu Val Cys Arg Val Ser Gln Ile
            340                 345                 350

Ile Pro

<210> SEQ ID NO 4
<211> LENGTH: 362
<212> TYPE: PRT
<213> ORGANISM: Human herpesvirus 5

<400> SEQUENCE: 4

Met Thr Thr Ser Thr Asn Asn Gln Thr Leu Thr Gln Val Ser Asn Met
1               5                   10                  15

Thr Asn His Thr Leu Asn Ser Thr Glu Ile Tyr Gln Leu Phe Glu Tyr
                20                  25                  30

Thr Arg Leu Gly Val Trp Leu Met Cys Ile Val Gly Thr Phe Leu Asn
            35                  40                  45

Val Leu Val Ile Thr Thr Ile Leu Tyr Tyr Arg Arg Lys Lys Lys Ser
50                  55                  60

Pro Ser Asp Thr Tyr Ile Cys Asn Leu Ala Val Ala Asp Leu Leu Ile
65                  70                  75                  80

Val Val Gly Leu Pro Phe Phe Leu Glu Tyr Ala Lys His His Pro Lys
                85                  90                  95

Leu Ser Arg Glu Val Val Cys Ser Gly Leu Asn Ala Cys Phe Tyr Ile
            100                 105                 110

Cys Leu Phe Ala Gly Val Cys Phe Leu Ile Asn Leu Ser Met Asp Arg
        115                 120                 125

Tyr Cys Val Ile Val Trp Gly Val Glu Leu Asn Arg Val Arg Asn Asn
130                 135                 140

Lys Arg Ala Thr Cys Trp Val Val Ile Phe Trp Ile Leu Ala Val Leu
145                 150                 155                 160

Met Gly Met Pro His Tyr Leu Met Tyr Ser His Thr Asn Asn Glu Cys
                165                 170                 175

Val Gly Glu Phe Ala Asn Glu Thr Ser Gly Trp Phe Pro Val Phe Leu
            180                 185                 190

Asn Thr Lys Val Asn Ile Cys Gly Tyr Leu Ala Pro Ile Ala Leu Met
        195                 200                 205

Ala Tyr Thr Tyr Asn Arg Met Val Arg Phe Ile Ile Asn Tyr Val Gly
210                 215                 220

Lys Trp His Met Gln Thr Leu His Val Leu Leu Val Val Val Val Ser
225                 230                 235                 240

Phe Ala Ser Phe Trp Phe Pro Phe Asn Leu Ala Leu Phe Leu Glu Ser
                245                 250                 255

Ile Arg Leu Leu Ala Gly Val Tyr Asn Asp Thr Leu Gln Asn Val Ile
            260                 265                 270

Ile Phe Cys Leu Tyr Val Gly Gln Phe Leu Ala Tyr Val Arg Ala Cys
        275                 280                 285

Leu Asn Pro Gly Ile Tyr Ile Leu Val Gly Thr Gln Met Arg Lys Asp
290                 295                 300

Met Trp Thr Thr Leu Arg Val Phe Ala Cys Cys Cys Val Lys Gln Glu

```
                     305                 310                 315                 320
Ile Pro Tyr Gln Asp Ile Asp Ile Glu Leu Gln Lys Asp Ile Gln Arg
                325                 330                 335

Arg Ala Lys His Thr Lys Arg Thr His Tyr Asp Arg Lys Asn Ala Pro
                340                 345                 350

Met Glu Ser Gly Glu Glu Phe Leu Leu
                355                 360

<210> SEQ ID NO 5
<211> LENGTH: 412
<212> TYPE: PRT
<213> ORGANISM: Human herpesvirus 5

<400> SEQUENCE: 5

Met Asp Thr Ile Ile His Asn Ser Thr Arg Asn Asn Thr Pro Pro His
1               5                   10                  15

Ile Asn Asp Thr Cys Asn Met Thr Gly Pro Leu Phe Ala Ile Arg Thr
                20                  25                  30

Thr Glu Ala Val Leu Asn Thr Phe Ile Ile Phe Val Gly Gly Pro Leu
            35                  40                  45

Asn Ala Ile Val Leu Ile Thr Gln Leu Leu Thr Asn Arg Val Leu Gly
        50                  55                  60

Tyr Ser Thr Pro Thr Ile Tyr Met Thr Asn Leu Tyr Ser Thr Asn Phe
65                  70                  75                  80

Leu Thr Leu Thr Val Leu Pro Phe Ile Val Leu Ser Asn Gln Trp Leu
                85                  90                  95

Leu Pro Ala Gly Val Ala Ser Cys Lys Phe Leu Ser Val Ile Tyr Tyr
                100                 105                 110

Ser Ser Cys Thr Val Gly Phe Ala Thr Val Ala Leu Ile Ala Ala Asp
            115                 120                 125

Arg Tyr Arg Val Leu His Lys Arg Thr Tyr Ala Arg Gln Ser Tyr Arg
        130                 135                 140

Ser Thr Tyr Met Ile Leu Leu Leu Thr Trp Leu Ala Gly Leu Ile Phe
145                 150                 155                 160

Ser Val Pro Ala Ala Val Tyr Thr Thr Val Val Met His His Asp Ala
                165                 170                 175

Asn Asp Thr Asn Asn Thr Asn Gly His Ala Thr Cys Val Leu Tyr Phe
                180                 185                 190

Val Ala Glu Glu Val His Thr Val Leu Leu Ser Trp Lys Val Leu Leu
            195                 200                 205

Thr Met Val Trp Gly Ala Ala Pro Val Ile Met Met Thr Trp Phe Tyr
        210                 215                 220

Ala Phe Phe Tyr Ser Thr Val Gln Arg Thr Ser Gln Lys Gln Arg Ser
225                 230                 235                 240

Arg Thr Leu Thr Phe Val Ser Val Leu Leu Ile Ser Phe Val Ala Leu
                245                 250                 255

Gln Thr Pro Tyr Val Ser Leu Met Ile Phe Asn Ser Tyr Ala Thr Thr
                260                 265                 270

Ala Trp Pro Met Gln Cys Glu His Leu Thr Leu Arg Arg Thr Ile Gly
            275                 280                 285

Thr Leu Ala Arg Val Val Pro His Leu His Cys Leu Ile Asn Pro Ile
        290                 295                 300

Leu Tyr Ala Leu Leu Gly His Asp Phe Leu Gln Arg Met Arg Gln Cys
305                 310                 315                 320

Phe Arg Gly Gln Leu Leu Asp Arg Arg Ala Phe Leu Arg Ser Gln Gln
```

```
                    325                 330                 335
Asn Gln Arg Ala Thr Ala Glu Thr Asn Leu Ala Ala Gly Asn Asn Ser
                340                 345                 350
Gln Ser Val Ala Thr Ser Leu Asp Thr Asn Ser Lys Asn Tyr Asn Gln
                355                 360                 365
His Ala Lys Arg Ser Val Ser Phe Asn Phe Pro Ser Gly Thr Trp Lys
                370                 375                 380
Gly Gly Gln Lys Thr Ala Ser Asn Asp Thr Ser Thr Lys Ile Pro His
385                 390                 395                 400
Arg Leu Ser Gln Ser His His Asn Leu Ser Gly Val
                405                 410

<210> SEQ ID NO 6
<211> LENGTH: 431
<212> TYPE: PRT
<213> ORGANISM: Human herpesvirus 5

<400> SEQUENCE: 6

Met Ser Pro Ser Val Glu Glu Thr Thr Ser Val Thr Glu Ser Ile Met
  1               5                  10                  15
Phe Ala Ile Val Ser Phe Lys His Met Gly Pro Phe Glu Gly Tyr Ser
                 20                  25                  30
Met Ser Ala Asp Arg Ala Ala Ser Asp Leu Leu Ile Gly Met Phe Gly
             35                  40                  45
Ser Val Ser Leu Val Asn Leu Leu Thr Ile Ile Gly Cys Leu Trp Val
         50                  55                  60
Leu Arg Val Thr Arg Pro Pro Val Ser Val Met Ile Phe Thr Trp Asn
 65                  70                  75                  80
Leu Val Leu Ser Gln Phe Phe Ser Ile Leu Ala Thr Met Leu Ser Lys
                 85                  90                  95
Gly Ile Met Leu Arg Gly Ala Leu Asn Leu Ser Leu Cys Arg Leu Val
                100                 105                 110
Leu Phe Val Asp Asp Val Gly Leu Tyr Ser Thr Ala Leu Phe Phe Leu
            115                 120                 125
Phe Leu Ile Leu Asp Arg Leu Ser Ala Ile Ser Tyr Gly Arg Asp Leu
        130                 135                 140
Trp His His Glu Thr Arg Glu Asn Ala Gly Val Ala Leu Tyr Ala Val
145                 150                 155                 160
Ala Phe Ala Trp Val Leu Ser Ile Val Ala Val Pro Thr Ala Ala
                165                 170                 175
Thr Gly Ser Leu Asp Tyr Arg Trp Leu Gly Cys Gln Ile Pro Ile Gln
            180                 185                 190
Tyr Ala Ala Val Asp Leu Thr Ile Lys Met Trp Phe Leu Leu Gly Ala
        195                 200                 205
Pro Met Ile Ala Val Leu Ala Asn Val Val Glu Leu Ala Tyr Ser Asp
    210                 215                 220
Arg Arg Asp His Val Trp Ser Tyr Val Gly Arg Val Cys Thr Phe Tyr
225                 230                 235                 240
Val Thr Cys Leu Met Leu Phe Val Pro Tyr Tyr Cys Phe Arg Val Leu
                245                 250                 255
Arg Gly Val Leu Gln Pro Ala Ser Ala Ala Gly Thr Gly Phe Gly Ile
            260                 265                 270
Met Asp Tyr Val Glu Leu Ala Thr Arg Thr Leu Leu Thr Met Arg Leu
        275                 280                 285
Gly Ile Leu Pro Leu Phe Ile Ile Ala Phe Phe Ser Arg Glu Pro Thr
```

```
                290                 295                 300
Lys Asp Leu Asp Asp Ser Phe Asp Tyr Leu Val Glu Arg Cys Gln Gln
305                 310                 315                 320

Ser Cys His Gly His Phe Val Arg Arg Leu Val Gln Ala Leu Lys Arg
                325                 330                 335

Ala Met Tyr Ser Val Glu Leu Ala Val Cys Tyr Phe Ser Thr Ser Val
                340                 345                 350

Arg Asp Val Ala Glu Ala Val Lys Lys Ser Ser Arg Cys Tyr Ala
                355                 360                 365

Asp Ala Thr Ser Ala Ala Val Val Thr Thr Thr Ser Glu Lys
                370                 375                 380

Ala Thr Leu Val Glu His Ala Glu Gly Met Ala Ser Glu Met Cys Pro
385                 390                 395                 400

Gly Thr Thr Ile Asp Val Ser Ala Glu Ser Ser Val Leu Cys Thr
                405                 410                 415

Asp Gly Glu Asn Thr Val Ala Ser Asp Ala Thr Val Thr Ala Leu
                420                 425                 430

<210> SEQ ID NO 7
<211> LENGTH: 71
<212> TYPE: PRT
<213> ORGANISM: Huma herpesvirus 8

<400> SEQUENCE: 7

Leu Gly Ala Ser Trp His Arg Pro Asp Lys Cys Cys Leu Gly Tyr Gln
1               5                   10                  15

Lys Arg Pro Leu Pro Gln Val Leu Leu Ser Ser Trp Tyr Pro Thr Ser
                20                  25                  30

Gln Leu Cys Ser Lys Pro Gly Val Ile Phe Leu Thr Lys Arg Gly Arg
            35                  40                  45

Gln Val Cys Ala Asp Lys Ser Lys Asp Trp Val Lys Lys Leu Met Gln
        50                  55                  60

Gln Leu Pro Val Thr Ala Arg
65                  70

<210> SEQ ID NO 8
<211> LENGTH: 638
<212> TYPE: PRT
<213> ORGANISM: Pseudomonas aeruginosa

<400> SEQUENCE: 8

Met His Leu Ile Pro His Trp Ile Pro Leu Val Ala Ser Leu Gly Leu
1               5                   10                  15

Leu Ala Gly Gly Ser Ser Ala Ser Ala Ala Glu Glu Ala Phe Asp Leu
                20                  25                  30

Trp Asn Glu Cys Ala Lys Ala Cys Val Leu Asp Leu Lys Asp Gly Val
            35                  40                  45

Arg Ser Ser Arg Met Ser Val Asp Pro Ala Ile Ala Asp Thr Asn Gly
        50                  55                  60

Gln Gly Val Leu His Tyr Ser Met Val Leu Glu Gly Gly Asn Asp Ala
65                  70                  75                  80

Leu Lys Leu Ala Ile Asp Asn Ala Leu Ser Ile Thr Ser Asp Gly Leu
                85                  90                  95

Thr Ile Arg Leu Glu Gly Gly Val Glu Pro Asn Lys Pro Val Arg Tyr
                100                 105                 110

Ser Tyr Thr Arg Gln Ala Arg Gly Ser Trp Ser Leu Asn Trp Leu Val
            115                 120                 125
```

```
Pro Ile Gly His Glu Lys Pro Ser Asn Ile Lys Val Phe Ile His Glu
        130                 135                 140

Leu Asn Ala Gly Asn Gln Leu Ser His Met Ser Pro Ile Tyr Thr Ile
145                 150                 155                 160

Glu Met Gly Asp Glu Leu Leu Ala Lys Leu Ala Arg Asp Ala Thr Phe
                165                 170                 175

Phe Val Arg Ala His Glu Ser Asn Glu Met Gln Pro Thr Leu Ala Ile
                180                 185                 190

Ser His Ala Gly Val Ser Val Met Ala Gln Thr Gln Pro Arg Arg
        195                 200                 205

Glu Lys Arg Trp Ser Glu Trp Ala Ser Gly Lys Val Leu Cys Leu Leu
        210                 215                 220

Asp Pro Leu Asp Gly Val Tyr Asn Tyr Leu Ala Gln Gln Arg Cys Asn
225                 230                 235                 240

Leu Asp Asp Thr Trp Glu Gly Lys Ile Tyr Arg Val Leu Ala Gly Asn
                245                 250                 255

Pro Ala Lys His Asp Leu Asp Ile Lys Pro Thr Val Ile Ser His Arg
                260                 265                 270

Leu His Phe Pro Glu Gly Gly Ser Leu Ala Ala Leu Thr Ala His Gln
        275                 280                 285

Ala Cys His Leu Pro Leu Glu Thr Phe Thr Arg His Arg Gln Pro Arg
        290                 295                 300

Gly Trp Glu Gln Leu Glu Gln Cys Gly Tyr Pro Val Gln Arg Leu Val
305                 310                 315                 320

Ala Leu Tyr Leu Ala Ala Arg Leu Ser Trp Asn Gln Val Asp Gln Val
                325                 330                 335

Ile Arg Asn Ala Leu Ala Ser Pro Gly Ser Gly Gly Asp Leu Gly Glu
                340                 345                 350

Ala Ile Arg Glu Gln Pro Glu Gln Ala Arg Leu Ala Leu Thr Leu Ala
        355                 360                 365

Ala Ala Glu Ser Glu Arg Phe Val Arg Gln Gly Thr Gly Asn Asp Glu
        370                 375                 380

Ala Gly Ala Ala Asn Ala Asp Val Val Ser Leu Thr Cys Pro Val Ala
385                 390                 395                 400

Ala Gly Glu Cys Ala Gly Pro Ala Asp Ser Gly Asp Ala Leu Leu Glu
                405                 410                 415

Arg Asn Tyr Pro Thr Gly Ala Glu Phe Leu Gly Asp Gly Asp Val
                420                 425                 430

Ser Phe Ser Thr Arg Gly Thr Gln Asn Trp Thr Val Glu Arg Leu Leu
        435                 440                 445

Gln Ala His Arg Gln Leu Glu Glu Arg Gly Tyr Val Phe Val Gly Tyr
        450                 455                 460

His Gly Thr Phe Leu Glu Ala Ala Gln Ser Ile Val Phe Gly Gly Val
465                 470                 475                 480

Arg Ala Arg Ser Gln Asp Leu Asp Ala Ile Trp Arg Gly Phe Tyr Ile
                485                 490                 495

Ala Gly Asp Pro Ala Leu Ala Tyr Gly Tyr Ala Gln Asp Gln Glu Pro
                500                 505                 510

Asp Ala Arg Gly Arg Ile Arg Asn Gly Ala Leu Leu Arg Val Tyr Val
                515                 520                 525

Pro Arg Ser Ser Leu Pro Gly Phe Tyr Arg Thr Ser Leu Thr Leu Ala
        530                 535                 540

Ala Pro Glu Ala Ala Gly Glu Val Glu Arg Leu Ile Gly His Pro Leu
```

```
                                545                 550                 555                 560

Pro Leu Arg Leu Asp Ala Ile Thr Gly Pro Glu Glu Gly Gly Arg
                565                 570                 575

Leu Glu Thr Ile Leu Gly Trp Pro Leu Ala Glu Arg Thr Val Val Ile
                580                 585                 590

Pro Ser Ala Ile Pro Thr Asp Pro Arg Asn Val Gly Gly Asp Leu Asp
                595                 600                 605

Pro Ser Ser Ile Pro Asp Lys Glu Gln Ala Ile Ser Ala Leu Pro Asp
                610                 615                 620

Tyr Ala Ser Gln Pro Gly Lys Pro Pro Arg Glu Asp Leu Lys
625                 630                 635

<210> SEQ ID NO 9
<211> LENGTH: 361
<212> TYPE: PRT
<213> ORGANISM: Artificial Sequence
<220> FEATURE:
<223> OTHER INFORMATION: Synthetic sequence

<400> SEQUENCE: 9

Glu Gly Gly Ser Leu Ala Ala Leu Thr Ala His Gln Ala Cys His Leu
1               5                   10                  15

Pro Leu Glu Thr Phe Thr Arg His Arg Gln Pro Arg Gly Trp Glu Gln
                20                  25                  30

Leu Glu Gln Cys Gly Tyr Pro Val Gln Arg Leu Val Ala Leu Tyr Leu
            35                  40                  45

Ala Ala Arg Leu Ser Trp Asn Gln Val Asp Gln Val Ile Arg Asn Ala
        50                  55                  60

Leu Ala Ser Pro Gly Ser Gly Gly Asp Leu Gly Glu Ala Ile Arg Glu
65                  70                  75                  80

Gln Pro Glu Gln Ala Arg Leu Ala Leu Thr Leu Ala Ala Ala Glu Ser
                85                  90                  95

Glu Arg Phe Val Arg Gln Gly Thr Gly Asn Asp Glu Ala Gly Ala Ala
                100                 105                 110

Asn Ala Asp Val Val Ser Leu Thr Cys Pro Val Ala Ala Gly Glu Cys
                115                 120                 125

Ala Gly Pro Ala Asp Ser Gly Asp Ala Leu Leu Glu Arg Asn Tyr Pro
            130                 135                 140

Thr Gly Ala Glu Phe Leu Gly Asp Gly Gly Asp Val Ser Phe Ser Thr
145                 150                 155                 160

Arg Gly Thr Gln Asn Trp Thr Val Glu Arg Leu Leu Gln Ala His Arg
                165                 170                 175

Gln Leu Glu Glu Arg Gly Tyr Val Phe Val Gly Tyr His Gly Thr Phe
                180                 185                 190

Leu Glu Ala Ala Gln Ser Ile Val Phe Gly Gly Val Arg Ala Arg Ser
            195                 200                 205

Gln Asp Leu Asp Ala Ile Trp Arg Gly Phe Tyr Ile Ala Gly Asp Pro
        210                 215                 220

Ala Leu Ala Tyr Gly Tyr Ala Gln Asp Gln Glu Pro Asp Ala Arg Gly
225                 230                 235                 240

Arg Ile Arg Asn Gly Ala Leu Leu Arg Val Tyr Val Pro Arg Ser Ser
                245                 250                 255

Leu Pro Gly Phe Tyr Arg Thr Ser Leu Thr Leu Ala Ala Pro Glu Ala
                260                 265                 270

Ala Gly Glu Val Glu Arg Leu Ile Gly His Pro Leu Pro Leu Arg Leu
            275                 280                 285
```

```
Asp Ala Ile Thr Gly Pro Glu Glu Gly Gly Arg Leu Glu Thr Ile
        290                 295                 300

Leu Gly Trp Pro Leu Ala Glu Arg Thr Val Val Ile Pro Ser Ala Ile
305                 310                 315                 320

Pro Thr Asp Pro Arg Asn Val Gly Gly Asp Leu Asp Pro Ser Ser Ile
                325                 330                 335

Pro Asp Lys Glu Gln Ala Ile Ser Ala Leu Pro Asp Tyr Ala Ser Gln
            340                 345                 350

Pro Gly Lys Pro Pro Lys Asp Glu Leu
        355                 360

<210> SEQ ID NO 10
<211> LENGTH: 734
<212> TYPE: PRT
<213> ORGANISM: Artificial Sequence
<220> FEATURE:
<223> OTHER INFORMATION: Synthetic sequence

<400> SEQUENCE: 10

Gln His His Gly Val Thr Lys Cys Asn Ile Thr Cys Ser Lys Met Thr
1               5                   10                  15

Ser Lys Ile Pro Val Ala Leu Leu Ile His Tyr Gln Gln Asn Gln Ala
            20                  25                  30

Ser Cys Gly Lys Arg Ala Ile Ile Leu Glu Thr Arg Gln His Arg Leu
        35                  40                  45

Phe Cys Ala Asp Pro Lys Glu Gln Trp Val Lys Asp Ala Met Gln His
    50                  55                  60

Leu Asp Arg Gln Ala Ala Ala Leu Thr Arg Asn Gly Gly Thr Phe Glu
65                  70                  75                  80

Lys Gln Ile Gly Glu Val Lys Pro Arg Thr Thr Pro Ala Ala Gly Gly
                85                  90                  95

Met Asp Glu Ser Val Val Leu Glu Pro Glu Ala Thr Gly Glu Ser Ser
            100                 105                 110

Ser Leu Glu Pro Thr Pro Ser Ser Gln Glu Ala Gln Arg Ala Leu Gly
        115                 120                 125

Thr Ser Pro Glu Leu Pro Thr Gly Val Thr Gly Ser Ser Gly Thr Arg
130                 135                 140

Leu Pro Pro Thr Pro Lys Ala Gln Asp Gly Gly Pro Val Gly Thr Glu
145                 150                 155                 160

Leu Phe Arg Val Pro Pro Val Ser Thr Ala Ala Thr Trp Gln Ser Ser
                165                 170                 175

Ala Pro His Gln Pro Gly Pro Ser Leu Trp Ala Glu Ala Lys Thr Ser
            180                 185                 190

Glu Ala Pro Ser Thr Gln Asp Pro Ser Thr Gln Ala Ser Thr Ala Ser
        195                 200                 205

Ser Pro Ala Pro Glu Glu Asn Ala Pro Ser Glu Gly Gln Arg Val Trp
    210                 215                 220

Gly Gln Gly Gln Ser Pro Arg Pro Glu Asn Ser Leu Glu Arg Glu Glu
225                 230                 235                 240

Met Gly Pro Val Pro Ala His Thr Asp Ala Phe Gln Asp Trp Gly Pro
                245                 250                 255

Gly Ser Met Ala His Val Ser Val Val Pro Val Ser Ser Glu Gly Thr
            260                 265                 270

Pro Ser Arg Glu Pro Val Ala Ser Gly Ser Trp Thr Pro Lys Ala Glu
        275                 280                 285
```

-continued

```
Glu Pro Ile His Ala Thr Met Asp Pro Gln Arg Leu Gly Val Leu Ile
    290                 295                 300

Thr Pro Val Pro Asp Ala Gln Ala Ala Thr Arg Arg Gln Ala Val Gly
305                 310                 315                 320

Leu Leu Ala Phe Leu Gly Leu Leu Phe Cys Leu Gly Val Ala Met Phe
                325                 330                 335

Thr Tyr Gln Ser Leu Gln Gly Cys Pro Arg Lys Met Ala Gly Glu Met
                340                 345                 350

Ala Glu Gly Leu Arg Tyr Ile Pro Arg Ser Cys Gly Ser Asn Ser Tyr
            355                 360                 365

Val Leu Val Pro Val Gly Gly Ser Leu Ala Leu Thr Ala His
    370                 375                 380

Gln Ala Cys His Leu Pro Leu Glu Thr Phe Thr Arg His Arg Gln Pro
385                 390                 395                 400

Arg Gly Trp Glu Gln Leu Glu Gln Cys Gly Tyr Pro Val Gln Arg Leu
                405                 410                 415

Val Ala Leu Tyr Leu Ala Ala Arg Leu Ser Trp Asn Gln Val Asp Gln
                420                 425                 430

Val Ile Arg Asn Ala Leu Ala Ser Pro Gly Ser Gly Gly Asp Leu Gly
            435                 440                 445

Glu Ala Ile Arg Glu Gln Pro Glu Gln Ala Arg Leu Ala Leu Thr Leu
    450                 455                 460

Ala Ala Ala Glu Ser Glu Arg Phe Val Arg Gln Gly Thr Gly Asn Asp
465                 470                 475                 480

Glu Ala Gly Ala Ala Asn Ala Asp Val Val Ser Leu Thr Cys Pro Val
                485                 490                 495

Ala Ala Gly Glu Cys Ala Gly Pro Ala Asp Ser Gly Asp Ala Leu Leu
                500                 505                 510

Glu Arg Asn Tyr Pro Thr Gly Ala Glu Phe Leu Gly Asp Gly Asp
    515                 520                 525

Val Ser Phe Ser Thr Arg Gly Thr Gln Asn Trp Thr Val Glu Arg Leu
530                 535                 540

Leu Gln Ala His Arg Gln Leu Glu Glu Arg Gly Tyr Val Phe Val Gly
545                 550                 555                 560

Tyr His Gly Thr Phe Leu Glu Ala Ala Gln Ser Ile Val Phe Gly Gly
                565                 570                 575

Val Arg Ala Arg Ser Gln Asp Leu Asp Ala Ile Trp Arg Gly Phe Tyr
                580                 585                 590

Ile Ala Gly Asp Pro Ala Leu Ala Tyr Gly Tyr Ala Gln Asp Gln Glu
            595                 600                 605

Pro Asp Ala Arg Gly Arg Ile Arg Asn Gly Ala Leu Leu Arg Val Tyr
    610                 615                 620

Val Pro Arg Ser Ser Leu Pro Gly Phe Tyr Arg Thr Ser Leu Thr Leu
625                 630                 635                 640

Ala Ala Pro Glu Ala Ala Gly Glu Val Glu Arg Leu Ile Gly His Pro
                645                 650                 655

Leu Pro Leu Arg Leu Asp Ala Ile Thr Gly Pro Glu Glu Gly Gly
                660                 665                 670

Arg Leu Glu Thr Ile Leu Gly Trp Pro Leu Ala Glu Arg Thr Val Val
            675                 680                 685

Ile Pro Ser Ala Ile Pro Thr Asp Pro Arg Asn Val Gly Gly Asp Leu
    690                 695                 700

Asp Pro Ser Ser Ile Pro Asp Lys Glu Gln Ala Ile Ser Ala Leu Pro
705                 710                 715                 720
```

```
Asp Tyr Ala Ser Gln Pro Gly Lys Pro Pro Lys Asp Glu Leu
                725                 730

<210> SEQ ID NO 11
<211> LENGTH: 437
<212> TYPE: PRT
<213> ORGANISM: Artificial Sequence
<220> FEATURE:
<223> OTHER INFORMATION: Synthetic sequence

<400> SEQUENCE: 11

Gln His His Gly Val Thr Lys Cys Asn Ile Thr Cys Ser Lys Met Thr
  1               5                  10                  15

Ser Lys Ile Pro Val Ala Leu Leu Ile His Tyr Gln Gln Asn Gln Ala
             20                  25                  30

Ser Cys Gly Lys Arg Ala Ile Ile Leu Glu Thr Arg Gln His Arg Leu
         35                  40                  45

Phe Cys Ala Asp Pro Lys Glu Gln Trp Val Lys Asp Ala Met Gln His
     50                  55                  60

Leu Asp Arg Gln Ala Ala Ala Leu Thr Arg Asn Gly Glu Gly Gly Ser
 65                  70                  75                  80

Leu Ala Ala Leu Thr Ala His Gln Ala Cys His Leu Pro Leu Glu Thr
                 85                  90                  95

Phe Thr Arg His Arg Gln Pro Arg Gly Trp Glu Gln Leu Glu Gln Cys
            100                 105                 110

Gly Tyr Pro Val Gln Arg Leu Val Ala Leu Tyr Leu Ala Ala Arg Leu
        115                 120                 125

Ser Trp Asn Gln Val Asp Gln Val Ile Arg Asn Ala Leu Ala Ser Pro
    130                 135                 140

Gly Ser Gly Gly Asp Leu Gly Glu Ala Ile Arg Glu Gln Pro Glu Gln
145                 150                 155                 160

Ala Arg Leu Ala Leu Thr Leu Ala Ala Glu Ser Glu Arg Phe Val
                165                 170                 175

Arg Gln Gly Thr Gly Asn Asp Glu Ala Gly Ala Ala Asn Ala Asp Val
            180                 185                 190

Val Ser Leu Thr Cys Pro Val Ala Gly Glu Cys Ala Gly Pro Ala
        195                 200                 205

Asp Ser Gly Asp Ala Leu Leu Glu Arg Asn Tyr Pro Thr Gly Ala Glu
    210                 215                 220

Phe Leu Gly Asp Gly Asp Val Ser Phe Ser Thr Arg Gly Thr Gln
225                 230                 235                 240

Asn Trp Thr Val Glu Arg Leu Leu Gln Ala His Arg Gln Leu Glu Glu
                245                 250                 255

Arg Gly Tyr Val Phe Val Gly Tyr His Gly Thr Phe Leu Glu Ala Ala
            260                 265                 270

Gln Ser Ile Val Phe Gly Gly Val Arg Ala Arg Ser Gln Asp Leu Asp
        275                 280                 285

Ala Ile Trp Arg Gly Phe Tyr Ile Ala Gly Asp Pro Ala Leu Ala Tyr
    290                 295                 300

Gly Tyr Ala Gln Asp Gln Glu Pro Asp Ala Arg Gly Arg Ile Arg Asn
305                 310                 315                 320

Gly Ala Leu Leu Arg Val Tyr Val Pro Arg Ser Ser Leu Pro Gly Phe
                325                 330                 335

Tyr Arg Thr Ser Leu Thr Leu Ala Ala Pro Glu Ala Ala Gly Glu Val
            340                 345                 350
```

```
Glu Arg Leu Ile Gly His Pro Leu Pro Leu Arg Leu Asp Ala Ile Thr
        355                 360                 365

Gly Pro Glu Glu Gly Gly Arg Leu Glu Thr Ile Leu Gly Trp Pro
    370                 375                 380

Leu Ala Glu Arg Thr Val Val Ile Pro Ser Ala Ile Pro Thr Asp Pro
385                 390                 395                 400

Arg Asn Val Gly Gly Asp Leu Asp Pro Ser Ser Ile Pro Lys Glu
                405                 410                 415

Gln Ala Ile Ser Ala Leu Pro Asp Tyr Ala Ser Gln Pro Gly Lys Pro
                420                 425                 430

Pro Lys Asp Glu Leu
        435

<210> SEQ ID NO 12
<211> LENGTH: 1290
<212> TYPE: DNA
<213> ORGANISM: Artificial Sequence
<220> FEATURE:
<223> OTHER INFORMATION: Synthetic sequence

<400> SEQUENCE: 12
tccccatatt cctcggacac cacaccctgc tgctttgcct acattgcccg cccactgccc      60
cgtgcccaca tcaaggagta tttctacacc agtggcaagt gctccaaccc agcagtcgtc     120
tttgtcaccc gaaagaaccg ccaagtgtgt gccaacccag agaagaaatg ggttcgggag     180
tacatcaact ctttggagat gagcgagggc ggcagcctgg ccgcgctgac cgcgcaccag     240
gcttgccacc tgccgctgga ctttcacc cgtcatcgcc agccgcgcgg ctgggaacaa      300
ctggagcagt gcggctatcc ggtgcagcgg ctggtcgccc tctacctggc ggcgcggctg     360
tcgtggaacc aggtcgacca ggtgatccgc aacgccctgg ccagccccgg cagcggcggc     420
gacctgggcg aagcgatccg cgagcagccg gagcaggccc gtctggccct gaccctggcc     480
gccgccgaga gcgagcgctt cgtccggcag ggcaccggca acgacgaggc cggcgcggcc     540
aacgccgacg tggtgagcct gacctgcccg gtcgccgccg gtgaatgcgc gggcccggcg     600
gacagcggcg acgccctgct ggagcgcaac tatcccactg cgcgcgagtt cctcggcgac     660
ggcggcgacg tcagcttcag caccgcggc acgcagaact ggacggtgga gcggctgctc     720
caggcgcacc gccaactgga ggagcgcggc tatgtgttcg tcggctacca cggcaccttc     780
ctcgaagcgg cgcaaagcat cgtcttcggc ggggtgcgcg cgcgcagcca ggacctcgac     840
gcgatctggc gcggttttcta tatcgccggc gatccggcgc tggcctacgg ctacgcccag     900
gaccaggaac ccgacgcacg cggccggatc cgcaacggtg ccctgctgcg ggtctatgtg     960
ccgcgctcga gctgccggg cttctaccgc accagcctga ccctggccgc gccggaggcg    1020
gcgggcgagg tcgaacggct gatcggccat ccgctgccgc tgcgcctgga cgccatcacc    1080 ggcccccgagg aggaaggcgg gcgcctggag accattctcg gctggccgct ggccgagcgc    1140
accgtggtga ttccctcggc gatccccacc gacccgcgca acgtcggcgg cgacctcgac    1200
ccgtccagca tccccgacaa ggaacaggcg atcagcgccc tgccggacta cgccagccag    1260
cccggcaaac cgccgaaaga cgagctctaa                                      1290

<210> SEQ ID NO 13
<211> LENGTH: 1194
<212> TYPE: DNA
<213> ORGANISM: Homo sapiens

<400> SEQUENCE: 13
```

```
atggctccga tatctctgtc gtggctgctc cgcttggcca ccttctgcca tctgactgtc      60
ctgctggctg acagcacca cggtgtgacg aaatgcaaca tcacgtgcag caagatgaca     120
tcaaagatac ctgtagcttt gctcatccac tatcaacaga accaggcatc atgcggcaaa     180
cgcgcaatca tcttggagac gagacagcac aggctgttct gtgccgaccc gaaggagcaa     240
tgggtcaagg acgcgatgca gcatctggac cgccaggctg ctgccctaac tcgaaatggc     300
ggcaccttcg agaagcagat cggcgaggtg aagcccagga ccaccctgc cgccggggga     360 atggacgagt ctgtggtcct ggagcccgaa gccacaggcg aaagcagtag cctggagccg     420
actccttctt cccaggaagc acagagggcc ctggggacct ccccagagct gccgacgggc     480
gtgactggtt cctcagggac caggctcccc ccgacgccaa aggctcagga tggagggcct     540
gtgggcacgg agcttttccg agtgcctccc gtctccactg ccgccacgtg cagagttct      600 gctccccacc aacctgggcc cagcctctgg gctgaggcaa agacctctga ggccccgtcc     660
acccaggacc cctccaccca ggcctccact cgtcctcccc cagccccaga ggagaatgct     720
ccgtctgaag ccagcgtgt gtggggtcag ggacagagcc ccaggccaga gaactctctg     780
gagcgggagg agatgggtcc cgtgccagcg cacacggatg ccttccagga ctgggggcct     840
ggcagcatgg cccacgtctc tgtggtccct gtctcctcag aagggacccc cagcagggag     900
ccagtggctt caggcagctg gacccctaag gctgaggaac ccatccatgc caccatggac     960
ccccagaggc tgggcgtcct tatcactcct gtccctgacg cccaggctgc cacccggagg    1020
caggcggtgg ggctgctggc cttccttggc ctcctcttct gcctgggggt ggccatgttc    1080
acctaccaga gctccagggg ctgccctcga aagatggcag agagatggc ggagggcctt    1140 cgctacatcc cccggagctg tggtagtaat tcatatgtcc tggtgcccgt gtga          1194

<210> SEQ ID NO 14
<211> LENGTH: 1065
<212> TYPE: DNA
<213> ORGANISM: Human herpesvirus 5

<400> SEQUENCE: 14
atgacaccga cgacgacgac cgcggaactc acgacggagt ttgactacga tgaagacgcg      60
actccttgtg ttttcaccga cgtgcttaat cagtcaaagc cagttacgtt gtttctgtac     120
ggcgttgtct ttctcttcgg ttccatcggc aacttcttgg tgatcttcac catcacctgg     180
cgacgtcgga ttcaatgctc cggcgatgtt tactttatca acctcgcggc cgccgatttg     240
cttttcgttt gtacactacc tctgtggatg caatacctcc tagatcacaa ctccctagcc     300
agcgtgccgt gtacgttact cactgcctgt ttctacgtgg ctatgtttgc cagtttgtgt     360
tttatcacgg agattgcact cgatcgctac tacgctattg tttacatgag atatcggcct     420
gtaaaacagg cctgccttt cagtattttt tggtggatct tgccgtgat catcgccatt     480 ccacacttta tggtggtgac caaaaaagac aatcaatgta tgaccgacta cgactactta     540
gaggtcagtt acccgatcat cctcaacgta gaactcatgc ttggtgcttt cgtgatcccg     600
ctcagtgtta tcagctactg ctactaccgc atttccagaa tcgttgcggt gtctcagtcg     660
cgccacaaag gtcgcattgt acgggtactt atagcggtcg tgcttgtctt tatcatcttt     720
tggctgccgt accacctaac gctgtttgtg gacacgttaa aactcctcaa atggatctcc     780
agcagctgcg agttcgaaag atcgctcaaa cgtgcgctca tcttgaccga gtcgctcgcc     840
ttttgtcact gttgtctcaa tccgctgctg tacgtcttcg tgggcaccaa gtttcggcaa     900
gaactacact gtctgctggc cgagtttcgc cagcgactct tttcccgcga tgtatcctgg     960
```

| | |
|---|---|
| taccacagca tgagcttttc gcgtcggagc tcgccgagtc gaagagagac atcttccgac | 1020 |
| acgctgtccg acgaggtgtg tcgcgtctca caaattatac cgtaa | 1065 |

<210> SEQ ID NO 15
<211> LENGTH: 1089
<212> TYPE: DNA
<213> ORGANISM: Human herpesvirus 5

<400> SEQUENCE: 15

| | |
|---|---|
| atgaccacct ctacaaataa tcaaacctta acgcaggtga gcaacatgac aaaccacacc | 60 |
| ttaaacagca ccgaaattta tcagttgttc gagtacactc ggttgggggt atggttgatg | 120 |
| tgcatcgtgg gcacgtttct gaacgtgctg gtgattacca ccatcctgta ctaccgtcgt | 180 |
| aagaaaaaat ctccgagcga tacctacatc tgcaacctgg ctgtagccga tctgttgatt | 240 |
| gtcgtcggcc tgccgttttt tctagaatat gccaagcatc accctaaact cagccgagag | 300 |
| gtggtttgtt cgggactcaa cgcttgtttc tacatctgtc tttttgccgg cgtttgtttt | 360 |
| ctcatcaacc tgtcgatgga tcgctactgc gtcatcgttt ggggtgtaga attgaaccgc | 420 |
| gtgcgaaata caagcgggc cacctgttgg gtggtgattt tttggatact agccgtgctc | 480 |
| atggggatgc cacattacct gatgtacagc cataccaaca acgagtgtgt tggtgaattc | 540 |
| gctaacgaga cgtcgggttg gttccccgtg ttttgaaca ccaaagttaa catttgcggc | 600 |
| tacctggcgc ccatcgcgct gatggcgtac acgtacaacc gtatggtgcg gtttatcatt | 660 |
| aactacgttg gtaaatggca catgcagacg ctccacgttc ttttggttgt ggttgtgtct | 720 |
| tttgccagct tttggtttcc tttcaacctg gcgctatttt tagaatccat ccgtcttctg | 780 |
| gcgggagtgt acaatgacac acttcaaaac gttattatct tctgtctata cgtcggtcag | 840 |
| tttttggcct acgttcgcgc ttgtctgaat cctgggatct acatcctagt aggcactcaa | 900 |
| atgaggaagg acatgtggac aaccctaagg gtattcgcct gttgctgcgt gaagcaggag | 960 |
| ataccttacc aggacattga tattgagcta caaaaggaca tacaagaag ggccaaacac | 1020 |
| accaaacgta cccattatga cagaaaaaat gcacctatgg agtccgggga ggaggaattt | 1080 |
| ctgttgtaa | 1089 |

<210> SEQ ID NO 16
<211> LENGTH: 1360
<212> TYPE: DNA
<213> ORGANISM: Human herpesvirus 5

<400> SEQUENCE: 16

| | |
|---|---|
| atggacacca tcatccacaa ctcggtgagc gccccaccta gagggagggg gggtagttta | 60 |
| atagcggagg cggatacgcg gttttctttt aagcgccgct gacttgtttc ttctgttttt | 120 |
| tcgccccgtg tgctgttccg cccagacccg caacaacact cctccgcaca tcaatgacac | 180 |
| ttgcaacatg acagggccgc tattcgccat tcgaaccacc gaagccgtac tcaacacatt | 240 |
| catcatcttc gtgggcggtc cacttaacgc catagtgttg atcacgcagc tgctcacgaa | 300 |
| tcgcgtgctt ggctattcga cgcccaccat ttacatgacc aacctctact ctactaattt | 360 |
| tctcacgctt actgtgctac cctttatcgt actcagcaac cagtggctgt gccggccgg | 420 |
| cgtggcctcg tgtaaatttc tatcggtgat ctactactca agctgcacag tgggcttttgc | 480 |
| caccgtagct ctgatcgccg ccgatcgtta tcgcgtcctt cataaacgaa catacgcacg | 540 |
| ccaatcatac cgttcaacct atatgatttt gctattgaca tggctcgctg gactaatttt | 600 |
| ttccgtgccc gcagctgttt acaccacggt ggtgatgcat cacgatgcca acgataccaa | 660 |

| | | |
|---|---|---|
| taatactaat gggcacgcca cctgtgtact gtacttcgta gctgaagaag tgcacacagt | 720 | |
| gctgctttcg tggaaagtgc tgctgacgat ggtatggggt gccgcacccg tgataatgat | 780 | |
| gacgtggttc tacgcattct tctactcaac cgtacagcgc acgtcacaga aacaaaggag | 840 | |
| tcgtacctta acctttgtta gcgtgctact catctccttc gtggcgctac aaactcccta | 900 | |
| cgtctctctc atgatcttca acagttatgc cacaaccgcc tggcccatgc agtgtgaaca | 960 | |
| cctcacactg cgacgcacca ttggcacgct ggcgcgtgtg gtgccccacc tacactgcct | 1020 | |
| cattaatccc atcctgtacg cgctgctggg tcatgatttt ctgcaacgca tgcggcagtg | 1080 | |
| tttccgcggt cagttgctgg accgccgcgc tttcctgaga tcgcagcaga atcagcgagc | 1140 | |
| tacagcggag acaaatctag cggctggcaa caattcacaa tcagtggcta cgtcattaga | 1200 | |
| caccaatagc aaaaactaca atcagcacgc caaacgcagc gtgtctttca attttcccag | 1260 | |
| cggtacgtgg aaaggcggcc agaaaaccgc gtccaacgac acatccacaa aaatccccca | 1320 | |
| tcgactctca caatcgcatc ataacctcag cggggtatga | 1360 | |

<210> SEQ ID NO 17
<211> LENGTH: 1296
<212> TYPE: DNA
<213> ORGANISM: Human herpesvirus

<400> SEQUENCE: 17

| | | |
|---|---|---|
| atgtcccctt ctgtggagga gactacctca gtcaccgagt ccatcatgtt cgctattgtg | 60 | |
| agtttcaaac acatgggccc gttcgaaggc tactctatgt cggccgatcg cgccgcctcg | 120 | |
| gatctactca tcggcatgtt cggctccgtt agcctggtca acctgctgac tatcatcggt | 180 | |
| tgcctctggg tgttgcgtgt tacgcggccg cccgtgtccg tgatgatttt tacttggaat | 240 | |
| ctggtactta gtcagttttt ttccatcctg gccaccatgt tgtccaaggg tatcatgctg | 300 | |
| cgtggcgctc taaatctcag cctctgtcgc ttagtgctct ttgtcgacga cgtgggccta | 360 | |
| tattcgacgg cgttgttttt cctctttctg atactggatc gtctgtcggc catatcttac | 420 | |
| ggccgtgatc tctggcatca tgagacgcgc gaaaacgccg gcgtggcgct ctacgcggtc | 480 | |
| gccttgcct gggttctttc catcgtagcc gctgtgccca ccgccgctac gggttcactg | 540 | |
| gactaccgtt ggctaggctg tcagatccct atacagtatg ccgcggtgga cctcaccatc | 600 | |
| aagatgtggt ttttgctggg ggcgcccatg atcgccgtac tggctaacgt ggtagagttg | 660 | |
| gcctacagcg atcggcgcga ccacgtctgg tcctacgtgg gtcgtgtctg caccttctac | 720 | |
| gtgacgtgtc tcatgctgtt tgtgcccta ctactgcttca gagtcctacg cggtgtactg | 780 | |
| cagcccgcta gcgcggccgg caccggtttc ggcattatgg attacgtgga attggctacg | 840 | |
| cgtacccttc tcaccatgcg tcttggcatt ctgccgctct ttatcattgc gttcttctcc | 900 | |
| cgcgagccca ccaaggatct ggatgactcc tttgattatc tggtcgagag atgtcagcaa | 960 | |
| agctgccacg tcatttcgt acgtcggttg gtgcaggcgt tgaagcgggc tatgtatagc | 1020 | |
| gtggagctgg ccgtgtgtta cttttctacg tccgtccgag acgtcgccga ggcggtgaaa | 1080 | |
| aagtcctcca gccgttgtta cgccgacgcg acgtcggcgg ccgttgtggt aacgacaacc | 1140 | |
| acgtcggaga aagccacgtt ggtggagcac gcggaaggca tggcttccga aatgtgtcct | 1200 | |
| gggactacga tcgatgtttc ggccgaaagt tcctccgtcc tctgcaccga cggcgaaaac | 1260 | |
| accgtcgcgt cggacgcgac ggtgacggca ttatga | 1296 | |

<210> SEQ ID NO 18
<211> LENGTH: 285
<212> TYPE: DNA

<213> ORGANISM: Human herpesvirus 8

<400> SEQUENCE: 18

| | |
|---|---|
| atggacacca agggcatcct gctcgtcgct gtgctgactg ccttgctttg tttgcaatct | 60 |
| ggggacacgc tggagcgtc ctggcataga ccggacaagt gctgtctcgg ttaccagaaa | 120 |
| agaccattac cacaggtgct tctgtccagc tggtacccca cctcccaact gtgcagcaag | 180 |
| ccgggtgtga tattttttgac aaagcgtggt cgccaggtgt gtgccgacaa atcgaaagac | 240 |
| tgggtgaaga agctgatgca gcaattacca gtcactgctc gctga | 285 |

<210> SEQ ID NO 19
<211> LENGTH: 1917
<212> TYPE: DNA
<213> ORGANISM: Pseudomonas aeruginosa

<400> SEQUENCE: 19

| | |
|---|---|
| atgcacctga tacccccattg gatcccctg gtcgccagcc tcggcctgct cgccggcggc | 60 |
| tcgtccgcgt ccgccgccga ggaagccttc gacctctgga cgaatgcgc caaagcctgc | 120 |
| gtgctcgacc tcaaggacgg cgtgcgttcc agccgcatga gcgtcgaccc ggccatcgcc | 180 |
| gacaccaacg gccagggcgt gctgcactac tccatggtcc tggagggcgg caacgacgcg | 240 |
| ctcaagctgg ccatcgacaa cgccctcagc atcaccagcg acggcctgac catccgcctc | 300 |
| gaaggcggcg tcgagccgaa caagccggtg cgctacagct acacgcgcca ggcgcgcggc | 360 |
| agttggtcgc tgaactggct ggtaccgatc ggccacgaga gccctcgaa catcaaggtg | 420 |
| ttcatccacg aactgaacgc cggcaaccag ctcagccaca tgtcgccgat ctacaccatc | 480 |
| gagatgggcg acgagttgct ggcgaagctg gcgcgcgatg ccaccttctt cgtcagggcg | 540 |
| cacgagagca acgagatgca accgacgctc gccatcagcc atgccggggt cagcgtggtc | 600 |
| atggcccaga cccagccgcg ccgggaaaag cgctggagcg aatgggccag cggcaaggtg | 660 |
| ttgtgcctgc tcgacccgct ggacggggtc tacaactacc tcgcccagca acgctgcaac | 720 |
| ctcgacgata cctgggaagg caagatctac cgggtgctcg ccggcaaccc ggcgaagcat | 780 |
| gacctggaca tcaaacccac ggtcatcagt catcgcctgc actttcccga gggcggcagc | 840 |
| ctggccgcgc tgaccgcgca ccaggcttgc cacctgccgc tggagacttt cacccgtcat | 900 |
| cgccagccgc gcggctggga acaactggag cagtgcggct atccggtgca gcggctggtc | 960 |
| gccctctacc tggcggcgcg gctgtcgtgg aaccaggtcg accaggtgat ccgcaacgcc | 1020 |
| ctggccagcc ccggcagcgg cggcgacctg ggcgaagcga tccgcgagca gccggagcag | 1080 |
| gcccgtctgg ccctgaccct ggccgccgcc gagagcgagc gcttcgtccg gcagggcacc | 1140 |
| ggcaacgacg aggccggcgc ggccaacgcc gacgtggtga gctgacctg cccggtcgcc | 1200 |
| gccggtgaat gcgcgggccc ggcggacagc ggcgacgccc tgctggagcg caactatccc | 1260 |
| actggcgcgc agttcctcgg cgacggcgg gacgtcagct tcagcacccg cggcacgcag | 1320 |
| aactggacgg tggagcggct gctccaggcg caccgccaac tggaggagcg cggctatgtg | 1380 |
| ttcgtcggct accacggcac cttcctcgaa gcggcgcaaa gcatcgtctt cggcggggtg | 1440 |
| cgcgcgcgca gccaggacct cgacgcgatc tggcgcggtt tctatatcgc cggcgatccg | 1500 |
| gcgctggcct acggctacgc ccaggaccag gaacccgacg cacgcggccg gatccgcaac | 1560 |
| ggtgccctgc tgcgggtcta tgtgccgcgc tcgagcctgc cgggcttcta ccgcaccagc | 1620 |
| ctgaccctgg ccgcgccgga ggcggcgggc gaggtcgaac ggctgatcgg ccatccgctg | 1680 |
| ccgctgcgcc tggacgccat caccggcccc gaggaggaag cgggcgcct ggagaccatt | 1740 |

```
ctcggctggc cgctggccga gcgcaccgtg gtgattccct cggcgatccc caccgacccg    1800
cgcaacgtcg gcggcgacct cgacccgtcc agcatcccg  acaaggaaca ggcgatcagc    1860
gccctgccgg actacgccag ccagcccggc aaaccgccgc gcgaggacct gaagtaa      1917
```

<210> SEQ ID NO 20
<211> LENGTH: 1086
<212> TYPE: DNA
<213> ORGANISM: Artificial Sequence
<220> FEATURE:
<223> OTHER INFORMATION: Synthetic sequence

<400> SEQUENCE: 20

```
gagggcggca gcctggccgc gctgaccgcg caccaggctt gccacctgcc gctggagact     60
ttcacccgtc atcgccagcc gcgcggctgg gaacaactgg agcagtgcgg ctatccggtg    120
cagcggctgg tcgccctcta cctggcggcg cggctgtcgt ggaaccaggt cgaccaggtg    180
atccgcaacg ccctggccag ccccggcagc ggcggcgacc tgggcgaagc gatccgcgag    240
cagccggagc aggcccgtct ggccctgacc ctggccgccg ccgagagcga gcgcttcgtc    300
cggcagggca ccggcaacga cgaggccggc gcggccaacg ccgacgtggt gagcctgacc    360
tgcccggtcg ccgccggtga atgcgcgggc ccggcggaca gcgcgacgc  cctgctggag    420 cgcaactatc ccactggcgc ggagttcctc ggcgacggcg gcgacgtcag cttcagcacc    480
cgcggcacgc agaactggac ggtggagcgg ctgctccagg cgcaccgcca actggaggag    540
cgcggctatg tgttcgtcgg ctaccacggc accttcctcg aagcggcgca agcatcgtc    600 ttcggcgggg tgcgcgcgcg cagccaggac ctcgacgcga tctggcgcgg tttctatatc    660
gccggcgatc cggcgctggc ctacggctac gcccaggacc aggaacccga cgcacgcggc    720
cggatccgca acggtgccct gctgcgggtc tatgtgccgc gctcgagcct gccgggcttc    780
taccgcacca gcctgaccct ggccgcgccg gaggcggcgg gcgaggtcga acggctgatc    840
ggccatccgc tgccgctgcg cctggacgcc atcaccggcc ccgaggagga aggcgggcgc    900
ctggagacca ttctcggctg gccgctggcc gagcgcaccg tggtgattcc ctcggcgatc    960
cccaccgacc cgcgcaacgt cggcggcgac ctcgacccgt ccagcatccc cgacaaggaa   1020
caggcgatca gcgccctgcc ggactacgcc agccagcccg gcaaaccgcc gaaagacgag   1080
ctctaa                                                              1086
```

<210> SEQ ID NO 21
<211> LENGTH: 2205
<212> TYPE: DNA
<213> ORGANISM: Artificial Sequence
<220> FEATURE:
<223> OTHER INFORMATION: Synthetic sequence

<400> SEQUENCE: 21

```
cagcaccacg gtgtgacgaa atgcaacatc acgtgcagca agatgacatc aaagatacct     60
gtagctttgc tcatccacta tcaacagaac caggcatcat gcggcaaacg cgcaatcatc    120
ttggagacga gacagcacag gctgttctgt gccgacccga aggagcaatg ggtcaaggac    180
gcgatgcagc atctggaccg ccaggctgct gccctaactc gaaatggcgg caccttcgag    240
aagcagatcg cgcaggtgaa gcccaggacc accctgccg  ccgggggaat ggacgagtct    300
gtggtcctgg agcccgaagc cacaggcgaa agcagtagcc tggagccgac tccttcttcc    360
caggaagcac agagggccct ggggacctcc ccagagctgc cgacgggcgt gactggttcc    420
tcagggacca ggctccccc  gacgccaaag gctcaggatg gagggcctgt gggcacggag    480
```

```
cttttccgag tgcctcccgt ctccactgcc gccacgtggc agagttctgc tccccaccaa    540
cctgggccca gcctctgggc tgaggcaaag acctctgagg ccccgtccac ccaggacccc    600
tccacccagg cctccactgc gtcctcccca gccccagagg agaatgctcc gtctgaaggc    660
cagcgtgtgt ggggtcaggg acagagcccc aggccagaga actctctgga gcggaggag     720
atgggtcccg tgccagcgca cacggatgcc ttccaggact gggggcctgg cagcatggcc    780
cacgtctctg tggtccctgt ctcctcagaa gggaccccca gcaggagcc agtggcttca     840
ggcagctgga cccctaaggc tgaggaaccc atccatgcca ccatggaccc cagaggctg     900
ggcgtcctta tcactcctgt ccctgacgcc caggctgcca cccggaggca ggcggtgggg    960
ctgctggcct tccttggcct cctcttctgc ctggggtgg ccatgttcac ctaccagagc    1020
ctccagggct gccctcgaaa gatggcagga gagatggcgg agggccttcg ctacatcccc    1080
cggagctgtg gtagtaattc atatgtcctg gtgcccgtgg agggcggcag cctggccgcg    1140
ctgaccgcgc accaggcttg ccacctgccg ctggagactt tcacccgtca tcgccagccg    1200
cgcggctggg aacaactgga gcagtgcggc tatccggtgc agcggctggt cgccctctac    1260
ctggcggcg gctgtcgtg gaaccaggtc gaccaggtga tccgcaacgc cctgccagc     1320
cccggcagcg gcggcgacct gggcgaagcg atccgcgagc agccggagca ggcccgtctg    1380
gccctgaccc tggccgccgc cgagagcgag cgcttcgtcc ggcagggcac cggcaacgac    1440
gaggccggcg cggccaacgc cgacgtggtg agcctgacct gcccggtcgc cgccggtgaa    1500
tgcgcgggcc cggcggacag cggcgacgcc ctgctggagc gcaactatcc cactggcgcg    1560
gagttcctcg gcgacggcgg cgacgtcagc ttcagcaccc gcggcacgca gaactggacg    1620
gtggagcggc tgctccaggc gcaccgccaa ctggaggagc gcggctatgt gttcgtcggc    1680
taccacggca ccttcctcga agcggcgcaa agcatcgtct cggcggggt gcgcgcgcgc    1740
agccaggacc tcgacgcgat ctggcgcggt ttctatatcg ccggcgatcc ggcgctggcc    1800
tacggctacg cccaggacca ggaacccgac gcacgcggcc ggatccgcaa cggtgccctg    1860
ctgcgggtct atgtgccgcg ctcgagcctg ccgggcttct accgcaccag cctgaccctg    1920
gccgcgccg aggcggcggg cgaggtcgaa cggctgatcg ccatccgct gccgctgcgc    1980
ctggacgcca tcaccggccc cgaggaggaa ggcgggcgcc tggagaccat tctcggctgg    2040
ccgctggccg agcgcaccgt ggtgattccc tcggcgatcc ccaccgaccc cgcaacgtc    2100
ggcggcgacc tcgacccgtc cagcatcccc gacaaggaac aggcgatcag cgccctgccg    2160
gactacgcca gccagcccgg caaaccgccg aaagacgagc tctaa                    2205

<210> SEQ ID NO 22
<211> LENGTH: 1314
<212> TYPE: DNA
<213> ORGANISM: Artificial Sequence
<220> FEATURE:
<223> OTHER INFORMATION: Synthetic sequence

<400> SEQUENCE: 22
cagcaccacg gtgtgacgaa atgcaacatc acgtgcagca agatgacatc aaagataccl    60
gtagctttgc tcatccacta tcaacagaac caggcatcat gcggcaaacg cgcaatcatc    120
ttggagacga gacagcacag gctgttctgt gccgacccga aggagcaatg ggtcaaggac    180
gcgatgcagc atctggaccg ccaggctgct gccctaactc gaaatggcga gggcggcagc    240
ctggccgcgc tgaccgcgca ccaggcttgc cacctgccgc tggagacttt cacccgtcat    300
cgccagccgc gcggctggga acaactggag cagtgcggct atccggtgca gcggctggtc    360
```

```
gccctctacc tggcggcgcg gctgtcgtgg aaccaggtcg accaggtgat ccgcaacgcc      420
ctggccagcc ccggcagcgg cggcgacctg ggcgaagcga tccgcgagca gccggagcag      480
gcccgtctgg ccctgaccct ggccgccgcc gagagcgagc gcttcgtccg gcagggcacc      540
ggcaacgacg aggccggcgc ggccaacgcc gacgtggtga gcctgacctg cccggtcgcc      600
gccggtgaat gcgcgggccc ggcggacagc ggcgacgccc tgctggagcg caactatccc      660
actggcgcgg agttcctcgg cgacggcggc gacgtcagct tcagcacccg cggcacgcag      720
aactggacgg tggagcggct gctccaggcg caccgccaac tggaggagcg cggctatgtg      780
ttcgtcggct accacggcac cttcctcgaa gcggcgcaaa gcatcgtctt cggcggggtg      840
cgcgcgcgca gccaggacct cgacgcgatc tggcgcggtt tctatatcgc cggcgatccg      900
gcgctggcct acggctacgc ccaggaccag gaacccgacg cacgcggccg gatccgcaac      960
ggtgccctgc tgcgggtcta tgtgccgcgc tcgagcctgc cgggcttcta ccgcaccagc     1020
ctgaccctgg ccgcgccgga ggcggcgggc gaggtcgaac ggctgatcgg ccatccgctg     1080
ccgctgcgcc tggacgccat caccggcccc gaggaggaag gcgggcgcct ggagaccatt     1140
ctcggctggc cgctggccga gcgcaccgtg gtgattccct cggcgatccc caccgacccg     1200
cgcaacgtcg gcggcgacct cgacccgtcc agcatccccg acaaggaaca ggcgatcagc     1260
gccctgccgg actacgccag ccagcccggc aaaccgccga agacgagct ctaa            1314

<210> SEQ ID NO 23
<211> LENGTH: 76
<212> TYPE: PRT
<213> ORGANISM: Artificial Sequence
<220> FEATURE:
<223> OTHER INFORMATION: Synthetic sequence

<400> SEQUENCE: 23

Gln His His Gly Val Thr Lys Cys Asn Ile Thr Cys Ser Lys Met Thr
1               5                   10                  15

Ser Lys Ile Pro Val Ala Leu Leu Ile His Tyr Gln Gln Asn Gln Ala
            20                  25                  30

Ser Cys Gly Lys Arg Ala Ile Ile Leu Glu Thr Arg Gln His Arg Leu
        35                  40                  45

Phe Cys Ala Asp Pro Lys Glu Gln Trp Val Lys Asp Ala Met Gln His
    50                  55                  60

Leu Asp Arg Gln Ala Ala Ala Leu Thr Arg Asn Gly
65                  70                  75
```